United States Patent
Fung et al.

(10) Patent No.: US 10,959,752 B2
(45) Date of Patent: Mar. 30, 2021

(54) PERICARDIAL ACCESS DEVICES AND METHODS

(71) Applicant: SentreHEART, Inc., Redwood City, CA (US)

(72) Inventors: Gregory W. Fung, Redwood Shores, CA (US); Arnold M. Escano, San Jose, CA (US)

(73) Assignee: SentreHEART LLC, Redwood City, CA (US)

( * ) Notice: Subject to any disclaimer, the term of this patent is extended or adjusted under 35 U.S.C. 154(b) by 102 days.

(21) Appl. No.: 14/633,068

(22) Filed: Feb. 26, 2015

(65) Prior Publication Data

US 2015/0272618 A1  Oct. 1, 2015

Related U.S. Application Data

(60) Provisional application No. 61/946,663, filed on Feb. 28, 2014.

(51) Int. Cl.
*A61B 17/34* (2006.01)
*A61B 17/00* (2006.01)

(52) U.S. Cl.
CPC .... *A61B 17/3417* (2013.01); *A61B 17/00234* (2013.01); *A61B 17/3478* (2013.01); *A61B 2017/00243* (2013.01); *A61B 2017/00247* (2013.01); *A61B 2017/00469* (2013.01); *A61B 2017/3405* (2013.01); *A61B 2017/347* (2013.01)

(58) Field of Classification Search
CPC ................ A61M 25/06; A61M 25/065; A61M 25/0084; A61B 17/3401; A61B 17/3478; A61N 1/0587
See application file for complete search history.

(56) References Cited

U.S. PATENT DOCUMENTS

| 3,685,509 A | 8/1972 | Bentall |
| 4,164,943 A | 8/1979 | Hill et al. |
| 4,222,380 A | 9/1980 | Terayama |

(Continued)

FOREIGN PATENT DOCUMENTS

| CN | 201664344 U | 12/2010 |
| CN | 102065781 A | 5/2011 |

(Continued)

OTHER PUBLICATIONS

International Search Report dated Jan. 14, 2014 for PCT Patent Application No. PCT/US2013/66104, filed on Oct. 22, 2013, two pages.

(Continued)

*Primary Examiner* — Martin T Ton
(74) *Attorney, Agent, or Firm* — Cooley LLP

(57) ABSTRACT

Described here are devices, systems, and methods for accessing the pericardial space through the pericardium. The access devices may include a plurality of elongate members having lumens that may be advanced together through the body to the pericardium. The elongate members may have different lengths and may be slideably positioned one within the lumen of another. At least one of the elongate members may comprise a distal tip configured to pierce tissue. In some instances, the access devices may also comprise a locking member to constrain the position of one elongate member relative to another.

15 Claims, 32 Drawing Sheets

(56) References Cited

U.S. PATENT DOCUMENTS

| | | | |
|---|---|---|---|
| 4,222,382 A | 9/1980 | Antonsson et al. | |
| 4,281,659 A | 8/1981 | Farrar et al. | |
| 4,991,578 A | 2/1991 | Cohen | |
| 4,995,866 A | 2/1991 | Amplatz et al. | |
| 5,071,428 A | 12/1991 | Chin et al. | |
| 5,226,890 A | 7/1993 | Ianniruberto et al. | |
| 5,332,398 A | 7/1994 | Miller et al. | |
| 5,336,252 A | 8/1994 | Cohen | |
| 5,407,427 A | 4/1995 | Zhu et al. | |
| 5,695,504 A | 12/1997 | Gifford, III et al. | |
| 5,827,216 A | 10/1998 | Igo et al. | |
| 5,972,013 A | 10/1999 | Schmidt | |
| 6,231,518 B1 | 5/2001 | Grabek et al. | |
| 6,423,051 B1 | 7/2002 | Kaplan et al. | |
| 6,488,689 B1 | 12/2002 | Kaplan et al. | |
| 6,890,295 B2 | 5/2005 | Michels et al. | |
| 6,918,890 B2 | 7/2005 | Schmidt | |
| 6,918,908 B2 | 7/2005 | Bonner et al. | |
| 7,226,458 B2 | 6/2007 | Kaplan et al. | |
| 7,309,328 B2 | 12/2007 | Kaplan et al. | |
| 7,318,829 B2 | 1/2008 | Kaplan et al. | |
| 7,610,104 B2 * | 10/2009 | Kaplan | A61N 1/0587 607/115 |
| 7,736,347 B2 | 6/2010 | Kaplan et al. | |
| 7,828,810 B2 | 11/2010 | Liddicoat et al. | |
| 7,846,168 B2 | 12/2010 | Liddicoat et al. | |
| 7,857,822 B2 | 12/2010 | Fleischman et al. | |
| 7,918,865 B2 | 4/2011 | Liddicoat et al. | |
| 8,273,072 B2 | 9/2012 | Jahns et al. | |
| 8,282,565 B2 | 10/2012 | Mahapatra et al. | |
| 8,308,720 B2 * | 11/2012 | Davies | A61B 18/1492 606/34 |
| 8,469,983 B2 | 6/2013 | Fung et al. | |
| 8,603,031 B2 | 12/2013 | Callas et al. | |
| 8,628,552 B2 | 1/2014 | Toy et al. | |
| 8,721,663 B2 | 5/2014 | Kaplan et al. | |
| 8,771,297 B2 | 7/2014 | Miller et al. | |
| 8,795,297 B2 | 8/2014 | Liddicoat et al. | |
| 8,795,310 B2 | 8/2014 | Fung et al. | |
| 8,974,473 B2 | 3/2015 | Kaplan et al. | |
| 8,986,278 B2 | 3/2015 | Fung et al. | |
| 8,986,325 B2 | 3/2015 | Miller et al. | |
| 8,996,133 B2 | 3/2015 | Kaplan et al. | |
| 9,198,664 B2 | 12/2015 | Fung et al. | |
| 9,271,819 B2 | 3/2016 | Liddicoat et al. | |
| 9,339,295 B2 | 5/2016 | Fung et al. | |
| 9,408,608 B2 | 8/2016 | Clark, III et al. | |
| 9,486,281 B2 | 11/2016 | Fung et al. | |
| 9,498,206 B2 | 11/2016 | Fung et al. | |
| 9,498,223 B2 | 11/2016 | Miller et al. | |
| 9,522,006 B2 | 12/2016 | Liddicoat et al. | |
| 9,724,105 B2 | 8/2017 | Kaplan et al. | |
| 2002/0045843 A1 | 4/2002 | Barker et al. | |
| 2002/0058925 A1 | 5/2002 | Kaplan et al. | |
| 2002/0103492 A1 | 8/2002 | Kaplan et al. | |
| 2002/0111637 A1 | 8/2002 | Kaplan et al. | |
| 2004/0092879 A1 * | 5/2004 | Kraus | A61B 17/3415 604/158 |
| 2004/0127854 A1 | 7/2004 | Leinsing et al. | |
| 2004/0167558 A1 | 8/2004 | Igo et al. | |
| 2004/0215168 A1 | 10/2004 | Verrier et al. | |
| 2005/0033321 A1 | 2/2005 | Fleischman | |
| 2005/0065561 A1 * | 3/2005 | Manning | A61M 25/0668 607/6 |
| 2005/0165466 A1 | 7/2005 | Morris et al. | |
| 2005/0187545 A1 | 8/2005 | Hooven et al. | |
| 2006/0106442 A1 | 5/2006 | Richardson et al. | |
| 2006/0149293 A1 | 7/2006 | King et al. | |
| 2006/0247672 A1 * | 11/2006 | Vidlund | A61B 17/3421 606/190 |
| 2007/0010708 A1 | 1/2007 | Ness | |
| 2007/0083194 A1 | 4/2007 | Kunis et al. | |
| 2007/0156217 A1 | 7/2007 | Kaplan et al. | |
| 2007/0156220 A1 | 7/2007 | Kaplan et al. | |
| 2007/0219546 A1 | 9/2007 | Mody et al. | |
| 2008/0221593 A1 | 9/2008 | Liddicoat et al. | |
| 2008/0294174 A1 | 11/2008 | Bardsley et al. | |
| 2009/0030380 A1 * | 1/2009 | Binmoeller | A61B 1/018 604/264 |
| 2009/0157118 A1 | 6/2009 | Miller et al. | |
| 2009/0187074 A1 | 7/2009 | Saadat et al. | |
| 2010/0106177 A1 | 4/2010 | Chanduszko et al. | |
| 2010/0191189 A1 | 7/2010 | Harding et al. | |
| 2010/0312256 A1 | 12/2010 | Kassab et al. | |
| 2010/0331854 A1 | 12/2010 | Greenberg et al. | |
| 2011/0054487 A1 | 3/2011 | Farnan | |
| 2011/0060182 A1 * | 3/2011 | Kassab | A61B 17/0057 600/37 |
| 2011/0077672 A1 | 3/2011 | Fleischman et al. | |
| 2011/0087247 A1 | 4/2011 | Fung et al. | |
| 2011/0144660 A1 | 6/2011 | Liddicoat et al. | |
| 2011/0282250 A1 | 11/2011 | Fung et al. | |
| 2012/0330184 A1 * | 12/2012 | Mahapatra | A61B 5/4887 600/561 |
| 2013/0027531 A1 | 1/2013 | Miyoshi et al. | |
| 2013/0144311 A1 | 6/2013 | Fung et al. | |
| 2013/0226026 A1 * | 8/2013 | Dillard | A61B 17/3421 600/562 |
| 2013/0274782 A1 | 10/2013 | Morgan | |
| 2014/0046343 A1 | 2/2014 | Okazaki et al. | |
| 2014/0114337 A1 | 4/2014 | Fung et al. | |
| 2014/0276985 A1 | 9/2014 | Clark et al. | |
| 2014/0303721 A1 | 10/2014 | Fung et al. | |
| 2014/0336676 A1 | 11/2014 | Pong et al. | |
| 2014/0350417 A1 | 11/2014 | Van Bladel et al. | |
| 2015/0119884 A1 | 4/2015 | Fung et al. | |
| 2015/0157328 A1 | 6/2015 | Miller et al. | |
| 2015/0173794 A1 | 6/2015 | Kurth et al. | |
| 2016/0008061 A1 | 1/2016 | Fung et al. | |
| 2016/0120549 A1 | 5/2016 | Fung et al. | |
| 2016/0235412 A1 | 8/2016 | Liddicoat et al. | |
| 2016/0242813 A1 * | 8/2016 | Cannon | A61B 17/3478 |
| 2016/0310145 A1 | 10/2016 | Clark, III et al. | |
| 2017/0209141 A1 | 7/2017 | Fung et al. | |
| 2017/0290591 A1 | 10/2017 | Miller et al. | |
| 2017/0290592 A1 | 10/2017 | Miller et al. | |
| 2017/0325819 A1 | 11/2017 | Kaplan et al. | |
| 2018/0064915 A1 | 3/2018 | Kurth et al. | |

FOREIGN PATENT DOCUMENTS

| | | |
|---|---|---|
| JP | 7-184912 A | 7/1995 |
| JP | 2002-523126 A | 7/2002 |
| JP | 2009-542338 A | 12/2009 |
| WO | WO-00/10471 A1 | 3/2000 |
| WO | WO-2003/066147 A1 | 8/2003 |
| WO | WO-2006/116310 A2 | 11/2006 |
| WO | WO-2006/116310 A3 | 11/2006 |
| WO | WO-2008/010905 A2 | 1/2008 |
| WO | WO-2008/010905 A3 | 1/2008 |
| WO | WO-2009/087592 A2 | 7/2009 |
| WO | WO-2009/120953 A2 | 10/2009 |
| WO | WO-2009/120953 A3 | 10/2009 |
| WO | WO-2009/139764 A1 | 11/2009 |
| WO | WO-2011/130456 A1 | 10/2011 |

OTHER PUBLICATIONS

International Search Report dated Jul. 1, 2011, for PCT Patent Application No. PCT/US2011/032382, filed on Apr. 13, 2011, 2 pages.

Ling, L.H. et al. (May 1997). "Pericardial Thickness Measured with Transesophageal Echocardiography: Feasibility and Potential Clinical Usefulness," *J. Am. Coll. Cardiol.* 29(6): 1317-1323.

Non-Final Office Action dated Nov. 22, 2000 for U.S. Appl. No. 09/397,392, filed Sep. 16, 1999, 3 pages.

Non-Final Office Action dated Jul. 9, 2003 for U.S. Appl. No. 10/002,329, filed Nov. 1, 2001, 7 pages.

Non-Final Office Action dated Mar. 22, 2005 for U.S. Appl. No. 10/002,329, filed Nov. 1, 2001, 7 pages.

(56) References Cited

OTHER PUBLICATIONS

Non-Final Office Action dated Jun. 29, 2005 for U.S. Appl. No. 10/002,329, filed Nov. 1, 2001, 7 pages.
Non-Final Office Action dated Oct. 3, 2005 for U.S. Appl. No. 10/002,329, filed Nov. 1, 2001, 8 pages.
Non-Final Office Action dated Mar. 26, 2014 for U.S. Appl. No. 13/086,328, filed Apr. 13, 2011, 8 pages.
Notice of Allowance dated Jul. 16, 2001 for U.S. Appl. No. 09/397,392, filed Sep. 16, 1999, 2 pages.
Notice of Allowance dated Jan. 28, 2004 for U.S. Appl. No. 10/002,329, filed Nov. 1, 2001, 4 pages.
Notice of Allowance dated Jul. 16, 2007 for U.S. Appl. No. 10/002,329, filed Nov. 1, 2001, 4 pages.
Restriction Requirement dated Aug. 11, 2000 for U.S. Appl. No. 09/397,392, filed Sep. 16, 1999, 6 pages.
Written Opinion of the International Searching Authority dated Jan. 14, 2014 for PCT Patent Application No. PCT/US2013/66104, filed on Oct. 22, 2013, six pages.
Written Opinion of the International Searching Authority dated Jul. 1, 2011, for PCT Patent Application No. PCT/US2011/032382, filed on Apr. 13, 2011, 5 pages.
U.S. Appl. No. 14/625,540, filed Feb. 18, 2015, for Miller et al.
U.S. Appl. No. 14/604,632, filed Jan. 23, 2015, for Kaplan et al.
Extended European Search Report dated Sep. 13, 2017, for EP Application No. 15 755 333.0, filed on Feb. 26, 2015, 6 pages.
Extended European Search Report dated May 13, 2016, for EP Application No. 13 848 264.1, filed on Oct. 22, 2013, seven pages.
International Search Report dated Jul. 28, 2015, for PCT Patent Application No. PCT/US2015/017849, filed on Feb. 26, 2015, 4 pages.
Non-Final Office Action dated Aug. 25, 2015 for U.S. Appl. No. 14/060,482, filed Oct. 22, 2013, 9 pages.
Notice of Allowance dated Jan. 20, 2016, for U.S. Appl. No. 14/060,482, filed Oct. 22, 2013, 8 pages.
Written Opinion of the International Searching Authority dated Jul. 28, 2015, for PCT Patent Application No. PCT/US2015/017849, filed on Feb. 26, 2015, 8 pages.
U.S. Appl. No. 15/634,982, filed Jun. 27, 2017, for Miller et al.
Extended European Search Report dated Dec. 8, 2017, for EP Application No. 11769550.2, 12 pages.
Final Office Action dated Aug. 27, 2014 for U.S. Appl. No. 13/086,328, filed Apr. 13, 2011, 9 pages.
International Search Report dated Sep. 12, 2002, for PCT Patent Application No. PCT/US2002/003084, filed on Feb. 4, 2002, 1 page.
International Search Report dated Jan. 14, 2014, for PCT Patent Application No. PCT/US2013/066104, filed on Oct. 22, 2013, 2 pages.
Non-Final Office Action dated Dec. 10, 2013 for U.S. Appl. No. 13/086,328, filed Apr. 13, 2011, 7 pages.
Non-Final Office Action dated Sep. 21, 2009, for U.S. Appl. No. 11/873,228, filed Oct. 16, 2007, 8 pages.
Notice of Allowance dated Nov. 17, 2014, for U.S. Appl. No. 13/086,328, filed Apr. 13, 2011, 9 pages.
Notice of Allowance dated Jan. 29, 2010, for U.S. Appl. No. 11/873,228, filed Oct. 16, 2007, 4 pages.
Partial European Search Report dated Aug. 16, 2017, for EP Application No. 11 769 550.2, filed on Apr. 13, 2011, 14 pages.
Written Opinion dated Jan. 14, 2014, for PCT Patent Application No. PCT/US2013/066104, filed on Oct. 22, 2013, 6 pages.

* cited by examiner

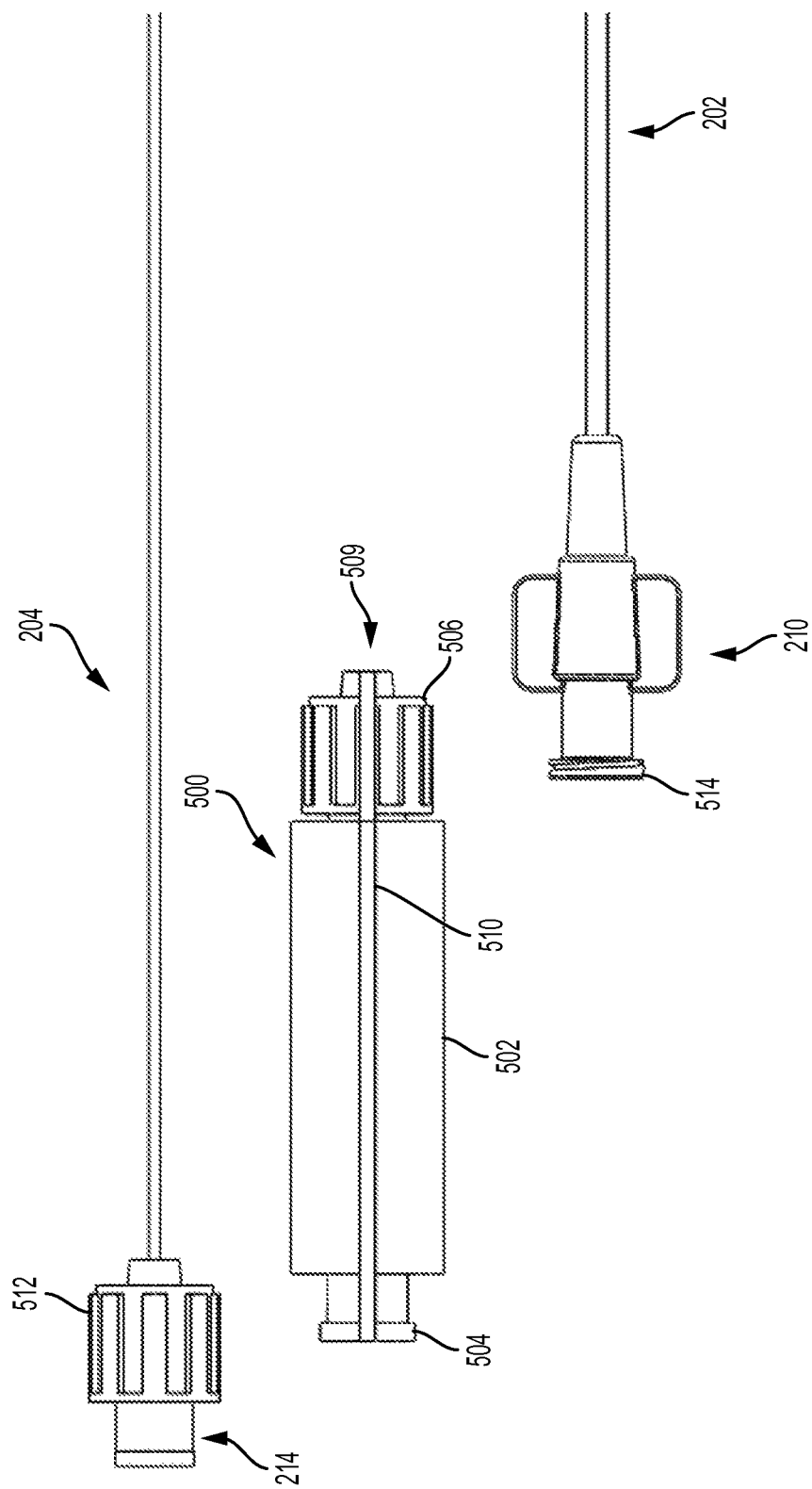

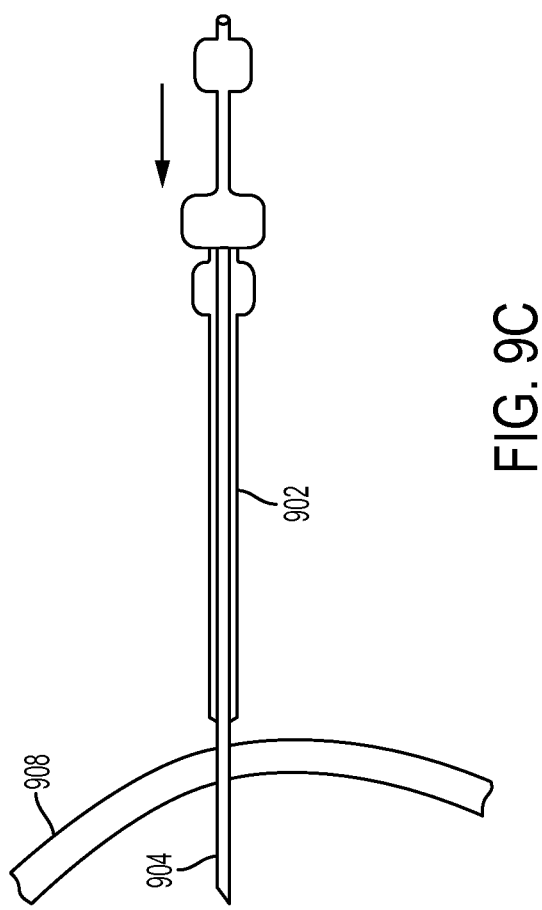

PERICARDIAL ACCESS DEVICES AND METHODS

CROSS-REFERENCE TO RELATED APPLICATIONS

This application claims priority to U.S. Provisional Patent Application Ser. No. 61/946,663, filed on Feb. 28, 2014, which is hereby incorporated by reference herein in its entirety.

FIELD

Described here are devices and methods for gaining access to the pericardial space through the pericardium.

BACKGROUND

It may be desirable to gain access to the internal and external structures of the heart for the treatment of cardiovascular disease. In some cases, the treatment may involve the delivery of one or more devices to the heart. A heart may be accessed in a number of ways. For example, a heart may be accessed for device delivery using an intravascular approach. In such an approach, a device may be advanced from a femoral vein to the vena cava, through which the chambers and valves of the right side of the heart (e.g., right atrium, right ventricle, etc.) may be accessed. The left side of the heart may also be accessed using an intravascular approach through a transseptal procedure. Alternatively, the left atrium and left ventricle may be intravascularly accessed by a retrograde pathway from the aorta.

Intravascular access to the heart may not be ideal in all circumstances, for example, for the delivery of larger devices, and especially if external structures of the heart are targeted. In such circumstances, the heart may also be accessed through an opening or puncture in the pericardium. Approaching the heart through the pericardium may provide direct access to the external (epicardial) surface of the heart. The ability to access the heart via a non-vascular pathway may be useful for a variety of applications, including device or drug delivery, left atrial appendage exclusion, ablation of fibrillating tissue, placement of leads, and the like.

Despite these benefits, puncturing the pericardium without contacting and/or damaging the heart itself may prove challenging. Current methods that attempt to reduce this risk involve grasping and/or suctioning the pericardium prior to puncturing it. But, at times, the presence of epicardial fat and other irregularities may prevent direct access to the pericardium. In some cases, highly trained users may be able to pierce the pericardium without piercing the heart by carefully advancing a needle toward the heart. They may rely on tactile feedback to avoid puncturing the heart and use this tactile feedback to accommodate and/or compensate for the displacement of the heart and pericardium during a beating heart procedure. However, advancing conventional needles to the heart by tactile feedback may be particularly risky for inexperienced users, as these conventional needles may be accidentally advanced into the heart.

Decreasing the diameter of the needle used to access the pericardial space may help to decrease the risk of puncturing the heart. However, reducing the size of the needle presents additional challenges. For example, decreasing the size of a needle tends to increase its flexibility, which may make it more difficult to steer to the pericardium. Additionally, smaller needles may catch on tissue and kink more easily. Furthermore, using a smaller needle to access the heart may prevent the placement of a guide wire large enough to advance a desirable treatment device. Using a needle with a larger diameter may be advantageous, but it presents other concerns. Larger needles may be more rigid and easier to steer, but, as mentioned above, they may present a significant risk of puncturing the heart. Additional methods and devices for accessing the pericardial space are desirable.

BRIEF SUMMARY

Described here are devices, systems, and methods for accessing the pericardial space. In some variations, a device may comprise a first elongate member having a lumen extending therethrough, a second elongate member having a tubular member with a tip configured to pierce tissue, and a locking member releasably connectable to the first and second elongate members. The second elongate member may be slideably positioned within the lumen of the first elongate member, and the locking member may constrain the first elongate member relative to the second elongate member. The inner diameter of the first elongate member may be larger than the outer diameter of the second elongate member. In some variations, the second elongate member may extend distally beyond a distal tip of the first elongate member when the locking member is connected. The first elongate member may comprise a needle, for example, a Tuohy needle or a beveled needle, may be at least about 3.5 inches (8.89 cm) long, and/or may be an 18-gauge needle. The first elongate member may also comprise a hypotube or a polymer sheath. In some variations, the first elongate member may further comprise a luer lock and/or a handle. The distal tip of the first elongate member may comprise a laser-cut pattern. The second elongate member may also comprise a needle, for example, a Tuohy needle or a beveled needle, may be at least about 8 inches (20.32 cm) in length, and/or may be a 21-gauge needle. In some variations, the second elongate member may further comprise a luer lock and/or a handle.

In some devices, the locking member may comprise a first connector configured to releasably connect it to the first elongate member and a second connector configured to releasably connect it to the second elongate member. The connectors may comprise snap-fit closures. In some variations, the first and second connectors may be configured to disconnect from the first and second elongate members when the locking member is rotated. In some variations, the locking member may be removed from the device in situ by displacing it radially relative to the second elongate member. In some variations, the locking member may comprise a hinging mechanism or a connector and a connector peg. In variations with a connector and connector peg, the connector peg may comprise a spring. The locking member may further comprise a body that is between about 1.5 inches (3.81 cm) and about 3 inches (7.62 cm) in length. In some variations, the locking member may comprise a body that is about 2 inches (5.08 cm) in length. The locking member may further comprise a longitudinal slit.

In some variations, the access devices may comprise first and second elongate members each having a lumen and a third elongate member having a tip configured to pierce tissue. The second elongate member may be slideably positioned within the lumen of the first elongate member and the third elongate member may be slideably positioned within the lumen of the second elongate member. The second elongate member may also be releasably connectable to the first elongate member such that the second elongate member may be constrained relative to the first elongate member. In some variations, the second elongate member may extend distally beyond a distal tip of the first elongate member when the second elongate member is releasably connected to the first elongate member. The first elongate member may comprise a needle, for example, a Tuohy needle or a beveled needle, may be at least about 6 inches (15.24 cm) long, and/or may be an 18-gauge needle. The first elongate member may also comprise a hypotube or a polymer sheath. In some variations, the first elongate member may further comprise a luer lock and/or a handle. The distal tip of the first elongate member may comprise a laser-cut pattern. The second elongate member may also comprise a needle, for example, a Tuohy needle or a beveled needle, may be at least about 8 inches (20.32 cm) in length, and/or may be a 20-gauge needle. In some variations, the second elongate member may comprise a hypotube or polymer sheath. Additionally, the second elongate member may further comprise a luer lock and/or a handle. The third elongate member may also comprise a needle, for example, a Tuohy needle or a beveled needle, may be at least about 10 inches (25.40) long, and/or may be a 23-gauge needle. In some variations, the third elongate member may further comprise a luer lock and/or a handle. The access device may be configured such that the inner diameter of the first elongate member is larger than the outer diameter of the second elongate member. In some variations, the inner diameter of the second elongate member may be larger than the outer diameter of the third elongate member. Furthermore, the inner diameter of the second elongate member may be larger than the outer diameter of the third elongate member.

In some variations, the access devices may further comprise a locking member which may be releasably connectable to the second and third elongate members and which may constrain the second elongate member relative to the third elongate member. In variations in which the access device comprises a locking member, the third elongate member may extend distally beyond a distal tip of the second elongate member when the locking member is connected. In some of these variations, the second elongate member may extend distally beyond a distal tip of the first elongate member when the second elongate member is releasably connected to the first elongate member. In some devices, the locking member may comprise a first connector configured to releasably connect it to the second elongate member and a second connector configured to releasably connect it to the third elongate member. The connectors may comprise snap-fit closures. In some variations, the first and second connectors are configured to disconnect from the second and third elongate members when the locking member is rotated. The locking member may be removed from the device in situ by displacing it radially relative to the third elongate member. In some variations, the locking member may comprise a hinging mechanism or a connector and a connector peg. In variations having a connector and a connector peg, the connector peg may comprise a spring. The locking member may further comprise a body that is between about 1.5 inches (3.81 cm) and about 3 inches (7.62 cm) in length. In some variations, the locking member may comprise a body that is about 2 inches (5.08 cm) in length. The locking member may further comprise a longitudinal slit.

The systems described here may comprise an access device and a guide wire sized and configured for use with the access device. The access device may comprise a first elongate member having a lumen, a second elongate member having a lumen and a tip configured to pierce tissue, and a locking member that may be releasably connectable to the first and second elongate members. The second elongate member may be slideably positioned within the lumen of the first elongate member, and the locking member may constrain the first elongate member relative to the second elongate member. The guide wire may be sized and configured for advancement through the lumen of the second elongate member. In some variations, the guide wire may have a diameter of about 0.018 inches (0.457 mm). Furthermore, the inner diameter of the second elongate member may be larger than the diameter of the guide wire. In some variations, the system may further comprise an introducer and in some instances, the introducer may be a 4-French or a 6-French introducer. In some variations, the introducer may be configured to receive a second guide wire, and the second guide wire may have a larger diameter than the first guide wire.

In some variations, the system may comprise first and second elongate members each having a lumen, a third elongate member having a lumen and a tip configured to pierce tissue, a first guide wire, and a second guide wire. The second elongate member may be slideably positioned within the lumen of the first elongate member, and the third elongate member may be slideably positioned within the lumen of the second elongate member. Additionally, the second elongate member may be releasably connectable to the first elongate member to constrain the second elongate member relative to the first elongate member. The first guide wire may be sized and configured for advancement through the lumen of the third elongate member, and the second guide wire may be sized and configured for advancement through the lumen of the first elongate member. In some variations, the diameter of the first guide wire may be about 0.014 inches (0.356 mm). Additionally, the diameter of the first guide wire may be smaller than the diameter of the third elongate member. In some variations, the diameter of the second guide wire may be about 0.035 inches (0.890 mm). Additionally, the diameter of the second guide wire may be smaller than the inner diameter of the first elongate member and larger than the inner diameter of the second elongate member. In some variations, the diameter of the second guide wire may be smaller than the inner diameter of the first elongate member and larger than the inner diameter of the second elongate member.

The methods described here may comprise advancing a distal portion of an access device to the pericardium, disengaging a locking member, and advancing part of the access device to pierce the pericardium. The access device may comprise a first elongate member having a lumen, a second elongate member having a tip configured to pierce tissue, and a locking member. The second elongate member may be slideably positioned within the lumen of the first elongate member and the locking member may constrain the position of the first elongate member relative to the second elongate member. Advancing part of the access device to pierce the pericardium may comprise advancing the second elongate member relative to the first elongate member to pierce the pericardium. The method may further comprise advancing a distal portion of a first guide wire through the second elongate member and into the pericardial space. In some variations, the method may further comprise removing the access device from the pericardial space and advancing an introducer along the first guide wire into the pericardial space. In some instances, the method may also further comprise removing the distal portion of the first guide wire from the pericardial space and advancing a distal portion of a second guide wire through the introducer and into the pericardial space.

In some variations, the access device may comprise first and second elongate members each having a lumen and a third elongate member having a tip configured to pierce tissue. In these variations, the second elongate member may be slideably positioned within the lumen of the first elongate member and may be releasably connectable to the first elongate member to constrain it relative to the first elongate member. Additionally, the third elongate member may be slideably positioned within the lumen of the second elongate member. In some variations, the access device may further comprise a locking member. In variations in which this access device is employed, the method to access the pericardial space may comprise advancing a distal portion of the access device to the pericardium, advancing the third elongate member toward the pericardium relative to the first and second elongate members to pierce the pericardium, advancing a distal portion of a first guide wire through the third elongate member and into the pericardial space, advancing a distal portion of the first elongate member into the pericardial space, advancing a distal portion of the second elongate member into the pericardial space, removing the third elongate member from the pericardial space, removing the second elongate member from the pericardial space, removing the first guide wire from the pericardial space, and advancing a second guide wire through the first elongate member and into the pericardial space. In variations in which an access device comprising a locking member is advanced to the pericardium, the method may further comprise disengaging the locking member.

BRIEF DESCRIPTION OF THE DRAWINGS

FIGS. 5A-5E depict embodiments of locking members suitable for use with the access devices described here.

FIGS. 9A-9E depict an illustrative method of accessing the pericardial space using a variation of the access devices described here.

DETAILED DESCRIPTION

Figure 1:
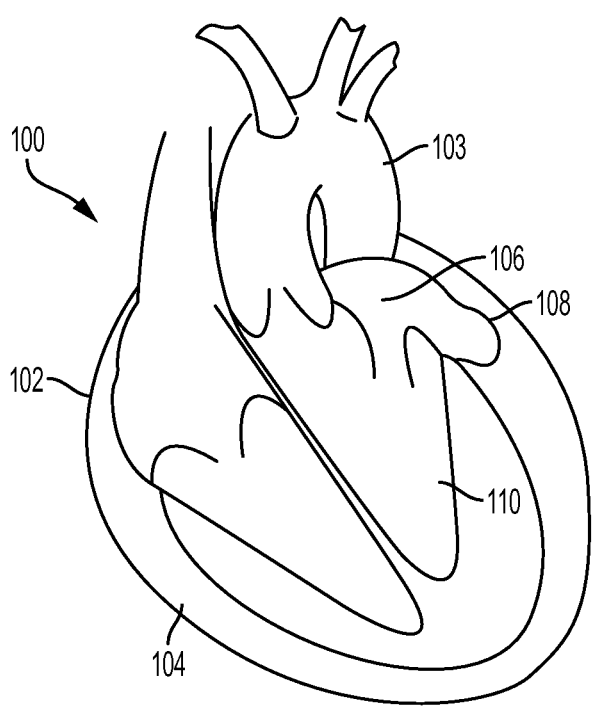
FIG. 1 depicts a typical anatomy of the heart and the pericardium.

Described here are devices and methods for accessing the pericardial space through the pericardium. The pericardium is a tough membrane that surrounds the heart. FIG. 1 depicts a heart (100) enclosed by a pericardium (102). FIG. 1 also depicts various anatomical structures of the heart, including the left atrium (106), left atrial appendage (108), left ventricle (110), and the aortic arch (103). The pericardium (102) may be filled with a fluid that may separate it from the heart. The space between the pericardium (102) and the heart (100) is the pericardial space (104). The distance between the pericardium and the surface of the heart may vary. For example, the pericardium may be about 5 millimeters away from heart in some areas, while the pericardium may directly contact the heart (100) in other areas. While the devices and methods described here are described in reference to puncturing the pericardium to provide access to the heart, it should be understood that these devices and methods may be used to create a puncture in or otherwise facilitate access to any fluid-filled membrane or sac to access the structures therein, e.g., dura mater, peritoneum, amniotic sac, and the like.

Devices

As mentioned above, described here are devices configured to provide access to the pericardial space. Generally, the access devices comprise a plurality of elongate members. The elongate members may each comprise a tubular member such as a needle. At least one of the elongate members may comprise a lumen extending therethrough, and the elongate members may be concentrically arranged (e.g., each elongate member may be positioned within the lumen of another until an outermost elongate member). It should be appreciated that the centers of the elongate members need not be aligned when the elongate members are arranged concentrically. When the elongate members are concentrically arranged, they may be slideable relative to one another. For example, an inner elongate member may be advanced relative to an outer elongate member to puncture tissue, as will be described in more detail below. At times, the relative positions of the elongate members may be temporarily constrained, by, for example, a locking member or a direct connection between two or more of the elongate members. Access devices comprising a plurality of concentrically arranged elongate members may facilitate advancement of the access device toward the pericardium and may further facilitate providing access to the pericardial space, as explained in more detail below.

Figure 2:
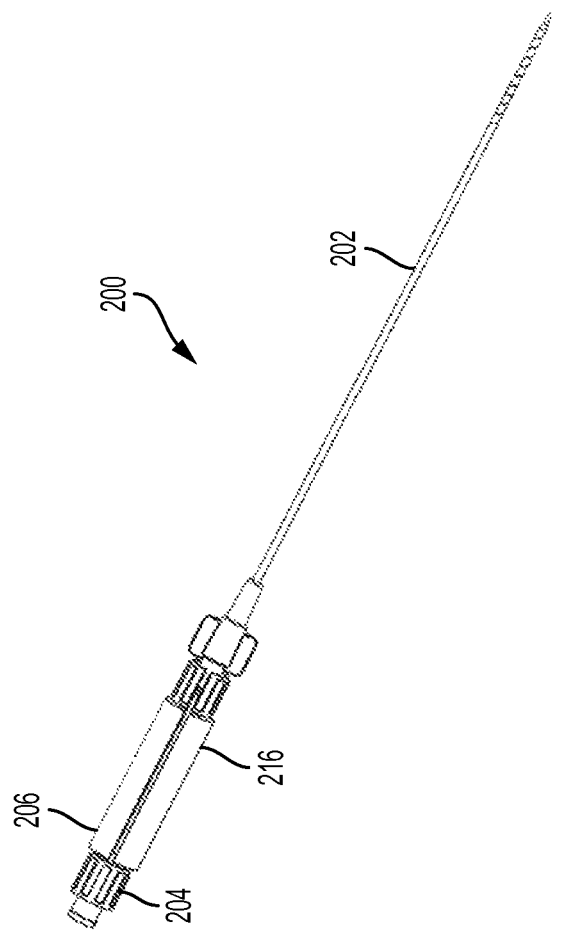
FIG. 2 depicts a perspective view of an embodiment of an access device.
Figure 3A:
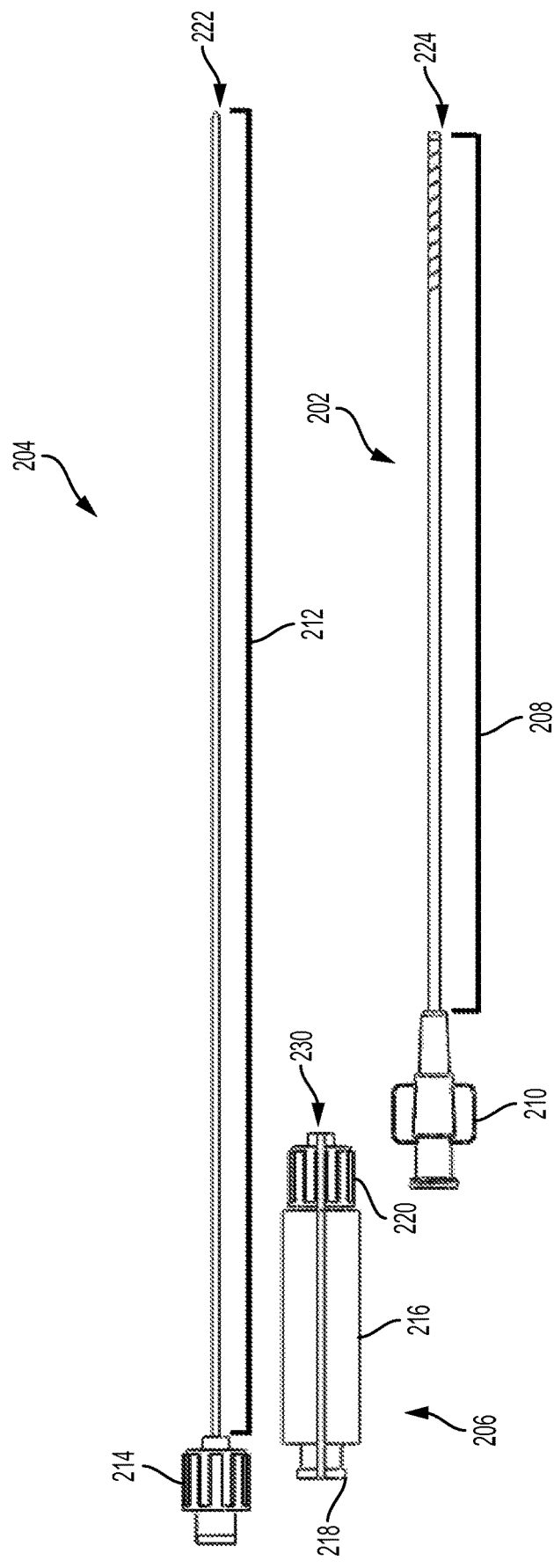
FIGS. 3A and 3B depict an exploded view and a cross-sectional view of the tubular members, respectively, of the access device of FIG. 2.

FIGS. 2 and 3A illustrate a variation of the access devices described here. FIG. 2 shows a perspective view of an access device (200) in an assembled configuration. FIG. 3A shows an exploded view of the access device (200) disassembled to better illustrate its components. As shown there, the access device (200) may comprise a first outer elongate member (202), a second inner elongate member (204), and a locking member (206). The outer elongate member (202) may comprise a lumen (224) extending therethrough, and at least a portion of the inner elongate member (204) may be sized to fit within the lumen (224) of the outer elongate member (202). When in the assembled configuration shown in FIG. 2, the inner (204) and outer (202) elongate members may be concentrically arranged such that a portion of the inner elongate member (204) extends at least partially through the lumen (224) of the outer elongate member (202). The inner elongate member (204) may comprise a distal tip configured to pierce tissue, such that the inner elongate member (204) may be advanced into the tissue to pierce or otherwise puncture the tissue. In some variations, the inner elongate member (204) may also comprise a lumen extending therethrough, but need not. In variations in which the inner elongate member (204) comprises a lumen (222), a guide wire or a fluid may be introduced into the pericardial space through the lumen (222) of the inner elongate member (204), as will be described in more detail below.

As mentioned above, the access device (200) may comprise a locking member (206), which may be configured to releasably constrain the position of the inner elongate member (204) relative to the outer elongate member (202). The locking member (206) may releasably engage the inner elongate member (204) and/or the outer elongate member (202) to limit relative movement between the outer and inner elongate members (202, 204), and may be disengaged to allow for relative movement between the outer and inner elongate members (202, 204). When the locking member (206) is engaged, the locking member (206) may limit relative movement between the inner and outer elongate members (202, 204) in a number of ways. For example, in some variations, the locking member (206) may axially fix the position of the outer elongate member (202) relative to the position of the inner elongate member (204) (e.g., the inner elongate member (204) may be prevented from sliding distally or proximally relative to the outer elongate member (202)). In other variations, the locking member (206) may be configured to limit or otherwise prevent axial advancement of inner elongate member (204) beyond a certain point relative to the outer elongate member (202), but may allow for axial withdrawal of the inner elongate member (204) relative to the outer elongate member (202). The locking member (206) may be configured to prevent or allow rotation of the inner elongate member (204) relative to the outer elongate member (202). Examples of locking members (206) are discussed in more detail below.

When the access device (200) is assembled, the access device (200) may be moveable between a delivery configuration and a piercing configuration. In the delivery configuration, as shown in FIG. 2, the inner elongate member (204) may be positioned to extend at least partially through the lumen (224) of the outer elongate member (202), and the locking member (206) may be used to constrain the relative positioning between the inner and outer elongate members (204, 202). This may allow the inner and outer elongate members (204, 202) to be advanced and manipulated together, for example, through the body and toward the pericardium. The access device (200) may be configured such that when the locking member (206) is engaged to constrain the relative positions of the inner and outer elongate members (204, 202), the distal tips of the inner and outer elongate members (204, 202) may have various configurations. For example, when the locking member (206) is engaged, the distal tip of the inner elongate member (204) may be positioned to extend beyond, be flush with, or be proximal to the distal tip of the outer elongate member (202).

In some instances, the concentric arrangement of the outer and inner elongate members (202, 204) may provide additional stiffness to the access device (200) and may facilitate advancement of the access device (200) through the body. In some variations, the outer elongate member (202) may be stiffer than the inner elongate member (204), and the outer elongate member (202) may reinforce or otherwise limit the bending of the inner elongate member (204) when the inner elongate member (204) is positioned in the lumen (224) of the outer elongate member (202). In some of these variations, the flexibility of the inner elongate member (204) relative to the outer elongate member (202) may result in the inner elongate member (204) being more likely to bend or deflect when the tip of the inner elongate member (204) contacts tissue, which may hinder the ability of a user to advance the inner elongate member (204) toward the pericardium. The increased rigidity provided by the outer elongate member (202) may, however, improve the ability of the access device (200) to push past or through tissue. In other variations, the inner elongate member (204) may be stiffer than the outer elongate member (202) and the inner elongate member (204) may reinforce or otherwise limit the bending of the outer elongate member (202) when the inner elongate member (204) is positioned in the lumen (224) of the outer elongate member (202). In some of these variations, the flexibility of the outer elongate member (202) relative to the inner elongate member (204) may result in the outer elongate member (202) being more likely to bend or deflect when the tip of the outer elongate member (202) contacts tissue, which may hinder the ability of a user to advance the outer elongate member (202) toward the pericardium. The increased rigidity provided by the inner elongate member (204) may, however, improve the ability of the access device (200) to push past or through tissue.

When a distal end of the access device (200) is positioned near an external surface of the pericardium, the access device (200) may be moved from the delivery configuration to the piercing configuration. To move the access device (200) from the delivery configuration to the piercing configuration, the inner elongate member (204) may be advanced through the lumen (224) of the outer elongate member (202) such that the distal tip of the inner elongate member (204) extends past the distal tip of the outer elongate member (202) (in variations where the distal tip of the inner elongate member (204) extends past the distal tip of the outer elongate member (202) in the delivery configuration, the distance between the distal tips of the inner and outer elongate members (204, 202) is increased as the access device is moved from the delivery configuration to the piercing configuration). As the inner elongate member (204) is advanced toward the pericardium, the distal tip of the inner elongate member may puncture the pericardium to position the distal tip of the inner elongate member (204) in the pericardial space. When a locking member (206) is used to constrain the relative position of the inner and outer elongate members (204, 202), the locking member (206) may be disengaged to allow the access device (200) to be moved from the deliver configuration to the piercing configuration.

While the access device (200) is described above as being advanced in the delivery configuration, it should be appreciated that, in some instances, the access device (200) may be placed in the delivery configuration after the outer elongate member (202) has been advanced to position a distal tip of that elongate member near the pericardium. In some of these variations, the outer elongate member (202) may be advanced into the body a certain distance, and the inner elongate member (204) may be advanced through the lumen (224) of the outer elongate member (202) to position the access device (200) in the delivery configuration. In some variations, the locking member (206) may facilitate placement of the access device (200) in the delivery configuration, as will be discussed in more detail below.

As mentioned above, FIG. 3A depicts the access device (200) with the outer elongate member (202), the inner elongate member (204), and the locking member (206) separated. As shown there, the outer elongate member (202) may comprise a tubular member (208) and a handle (210). The lumen (224) of the outer elongate member (202) may extend at least partially through the tubular member (208) and the handle (210). In some variations, the lumen (224) may extend between an inlet in the handle (210) and an outlet in a distal portion of the tubular member (208). The tubular member (208) may comprise a needle (e.g., a Tuohy needle, a beveled needle), a sheath, a hypotube, or any other suitable tubular device. The length and diameter of the tubular member (208) may vary based on anatomical considerations and other variables. In some embodiments, the distal end of the outer elongate member (202) may comprise a laser cut pattern, for example, an interrupted spiral cut, a puzzle piece pattern, a dovetail pattern, etc., which may increase the flexibility of the distal end of the outer elongate member (202). In some variations, this increased flexibility may further protect against lacerating the beating heart when advancing the tubular member (208) into the pericardial space. In some variations, the laser cut pattern may extend proximally from the distal tip of the outer elongate member any suitable distance, for example, about 0.197 inches (5 mm) to about 0.590 inches (15 mm). As used here, "about" means ±2%.

The tubular member (208) and the handle (210) may be assembled in any suitable configuration. In some variations, the outer elongate member (202) may be constructed such that the handle (210) is connected to a proximal portion of the tubular member (208). In some of these embodiments, the tubular member (208) and the handle (210) may be integrally formed. In others of these embodiments, the handle (210) and the tubular member (208) may be constructed separately and attached to each other (e.g., via one or more adhesives, welding, or the like). In some variations, the outer elongate member (202) may be configured to temporarily connect to the locking member (206), the inner elongate member (204), or another device. In some of these variations, the handle (210) may comprise a connector. In these variations, the connector of the handle (210) may be configured to releasably connect to a corresponding connector on a locking member, an inner elongate member, or the like. In other variations, the tubular member (208) may comprise a connector, which may be configured to releasably connect to a corresponding connector on a locking member, an inner elongate member, or the like. The handle (210) may also be configured to facilitate manipulation of the tubular member (208) of the outer elongate member (202). For example, the handle (210) may comprise indentations, ridges, bumps, tabs, or any other structural indication to facilitate placement of the hands of the user on the handle (210).

Returning to FIG. 3A, the inner elongate member (204) may also comprise a tubular member (212) and a handle (214). The tubular member (212) may comprise a needle (e.g., a Tuohy needle, a beveled needle), a sheath, a hypotube, or any other suitable tubular device, such as discussed in more detail below. Generally, the tubular member (212) comprises a distal tip configured to pierce tissue. For example, the distal tip may include one or more sharpened or beveled edges. The length and diameter of the tubular member (212) may vary based on anatomical considerations and other variables. In some embodiments, the distal tip of the inner elongate member (204) may comprise a laser cut pattern, as discussed in greater detail above with respect to the outer elongate member (202). In some variations, the inner elongate member (204) may comprise a lumen (222). In some of these variations, the lumen (222) may extend at least partially through the tubular member (212) and the handle (214). In some variations, the lumen (222) may extend between an inlet in the handle (214) and an outlet in a distal portion of the tubular member (212). It should be appreciated that the inner elongate member (204) and outer elongate member (202) may comprise any combination of tubular members. For example, in some variations, the inner elongate member and outer elongate member may each comprise needles. In other variations, the outer elongate member may comprise a hypotube, and the inner elongate member may comprise a needle. In still other variations, the outer elongate member may comprise a sheath, and the inner elongate member may comprise a needle.

The tubular member (212) and the handle (214) may be assembled in any suitable configuration. In some variations, the inner elongate member (204) may be constructed such that the handle (214) is connected to a proximal portion of the tubular member (212). In some of these embodiments, the tubular member (212) and the handle (214) may be integrally formed. In others of these embodiments, the handle (214) and the tubular member (212) may be constructed separately and attached to each other (e.g., via one or more adhesives, welding, or the like). In some variations, the inner elongate member (204) may be configured to temporarily connect to the locking member (206), the outer elongate member (202), or another device. In some of these variations, the handle (214) may comprise a connector. In these variations, the connector of the handle (214) may be configured to releasably connect to a corresponding connector on a locking member, outer elongate member, or the like. In other variations, the tubular member (212) may comprise a connector, which may be configured to releasably connect to a corresponding connector on a locking member, an outer elongate member, or the like. The handle (214) may also be configured to facilitate manipulation of the tubular member (212) of the inner elongate member (204). For example, the handle (214) may comprise indentations, ridges, bumps, tabs, or any other structural indication to facilitate placement of the hands of the user on the handle (214). Additionally, in some variations, the handle (214) may be configured such that at least a portion of the handle (214) is sized such that it is prevented from entering the lumen (224) of the outer elongate member (202). In these variations, the handle (214) of the inner elongate member (204) may limit advancement of the inner elongate member (204) through the lumen (224) of the outer elongate member (202). In these variations, the inner elongate member (204) may be advanced into the lumen (224) (e.g., through the inlet of the lumen (224) of the outer elongate member (202)) until the handle (214) engages the inlet and prevents further advancement of the inner elongate member (204) relative to the outer elongate member (202).

Figure 3B:
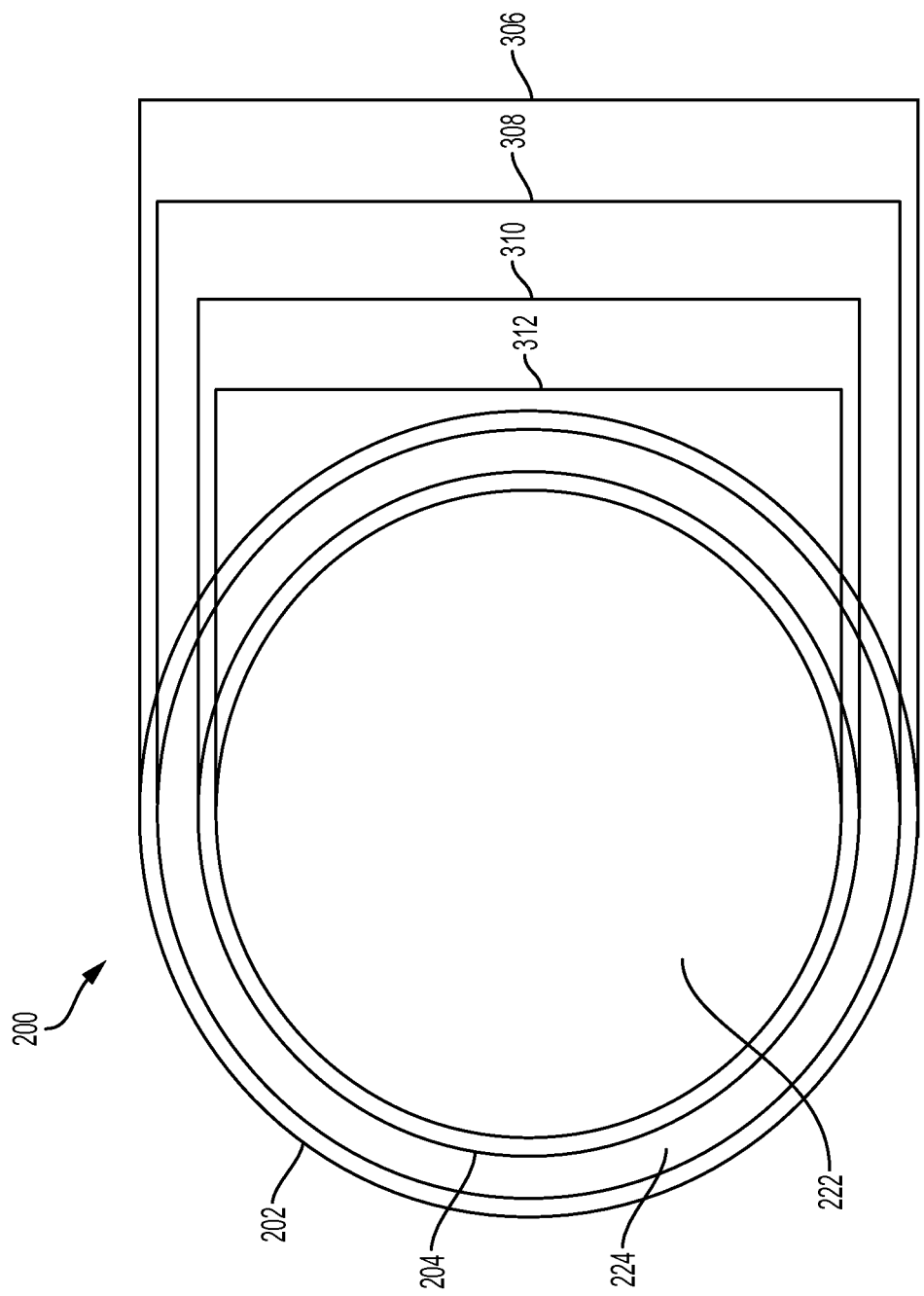

The inner and outer elongate members (202, 204) may have any suitable dimensions. Turning to FIG. 3B, depicted there is a cross-sectional view of the tubular members of the access device (200) with the inner elongate member (204) positioned within the lumen (224) of the outer elongate member (202). As shown there, the tubular member (208) of the outer elongate member (202) may have an outer diameter (306) and an inner diameter (308) (i.e., the diameter of the lumen (224)). Similarly, the tubular member (212) of the inner elongate member (204) may have an outer diameter (310). In variations where the inner elongate member (204) comprises a lumen (222), the tubular member may also have an inner diameter (312) (i.e., the diameter of the lumen (222)).

The outer elongate member (202) may have any suitable inner and outer diameters. In some variations, the inner diameter (308) may be at least about 0.033 inches (0.838 mm). In some variations, the inner diameter (308) may be about 0.033 inches (0.838 mm). In some variations, the inner diameter (308) may be at least about 0.036 inches (0.914 mm). In some variations, the inner diameter may be about 0.036 inches (0.914 mm). In some variations, the outer diameter (306) may be at least about 0.05 inches (1.27 mm), and in some variations, may be about 0.05 inches (1.27 mm).

For example, in some variations, the outer elongate member (202) may comprise an 18-gauge tubular member (e.g., an 18-gauge tube or an 18-gauge needle) having an inner diameter of about 0.036 inches (0.914 mm) and an outer diameter of about 0.05 inches (1.27 mm). Similarly, the inner elongate member (204) may have any suitable inner and outer diameters. In some variations, the inner diameter (312) may be less than or equal to about 0.023 inches (0.584 mm). In some variations, the inner diameter (312) may be about 0.023 inches (0.584 mm). In some variations, the outer diameter (310) may be less than or equal to about 0.0355 inches (0.902 mm), and in some variations, may be about 0.0355 inches (0.902 mm). For example, in some variations, the outer elongate member (202) may comprise a 20-gauge tubular member (e.g., a 20-gauge tube or a 20-gauge needle) having an inner diameter of about 0.023 inches (0.495 mm) and an outer diameter of about 0.0355 inches (0.902 mm). In some variations, the inner diameter (312) may be less than or equal to about 0.0195 inches (0.495 mm). In some variations, the inner diameter (312) may be about 0.0195 inches (0.495 mm). In some variations, the outer diameter (310) may be less than or equal to about 0.032 inches (0.813 mm), and in some variations, may be about 0.032 inches (0.813 mm). For example, in some variations, the outer elongate member (202) may comprise a 21-gauge tubular member (e.g., a 21-gauge tube or a 21-gauge needle) having an inner diameter of about 0.0195 inches (0.495 mm) and an outer diameter of about 0.032 inches (0.813 mm).

As mentioned above, the tubular member (212) of the inner elongate member (204) may be configured to fit and slide within the lumen (224) of the outer elongate member (202). Accordingly, the inner diameter (308) of the outer elongate member (202) may be larger than the outer diameter (310) of the inner elongate member (204). For example, in some variations, the inner diameter (308) of the outer elongate member (202) may be at least about 0.033 inches (0.838 mm), and the outer diameter (310) of the inner elongate member (204) may be less than or equal to about 0.032 inches (0.813 mm). In some of these variations, the inner diameter (308) of the outer elongate member (202) may be about 0.033 inches (0.838 mm) and the outer diameter (310) of the inner elongate member (204) may be about 0.032 inches (0.813 mm). For example, in some variations, the outer elongate member (202) may comprise an 18-gauge tubular member (e.g., an 18-gauge tube or an 18-gauge needle) having an inner diameter of about 0.033 inches (0.838 mm), and the inner elongate member (204) may comprise a 21-gauge tubular member (e.g., a 21-gauge tube or a 21-gauge needle) having an outer diameter of about 0.032 inches (0.813 mm).

In some instances, it may be desirable to minimize the space between the inner diameter (308) of the tubular member (208) of the outer elongate member (202) and the outer diameter (310) of the tubular member (212) of the inner elongate member (204). Reducing the space between the inner diameter (308) and the outer diameter (310) may reduce the likelihood that tissue (e.g., pericardial tissue) becomes caught or otherwise lodged in the space between the inner and outer elongate members, which may damage or sever tissue as the inner and/or outer elongate members are advanced or manipulated. For example, once the inner elongate member (204) has punctured the pericardium and advanced into the pericardial space, the outer elongate member (202) may be advanced along the inner elongate member (204) to increase the size of the access site formed in the pericardium (which may provide for the introduction of a larger guide wire into the pericardial space, as will be discussed in more detail below). Minimizing the space between the two elongate members (202, 204) as described above may decrease the risk that the distal tip of the access device (200) will catch pericardial tissue and create a larger opening than desired when facilitating access to the pericardial space, and may also help ease the transition as the outer elongate member is advanced through an opening in the pericardium. In other instances, minimizing the space between the two elongate members may reduce the likelihood of heart lacerations by the outer elongate member (202) as it is advanced over the inner elongate member (204).

In some embodiments, the inner diameter (308) of the tubular member (208) of the outer elongate member (202) may be less than or equal to about 0.006 inches (0.152 mm) larger than the outer diameter (310) of the tubular member (212) of the inner elongate member (204). In some of these embodiments, the inner diameter (308) of the outer elongate member (202) may be between about 0.003 inches (0.076 mm) and about 0.006 inches (0.152 mm) larger than the outer diameter (310) of the inner elongate member (204). In some embodiments, the inner diameter (308) of the tubular member (208) of the outer elongate member (202) may be less than or equal to about 0.001 inches (0.025 mm) larger than the outer diameter (310) of the tubular member (212) of the inner elongate member (204).

As mentioned above, and as shown in FIG. 3A, the tubular member (212) of the inner elongate member (204) may be longer than the outer elongate member (202) such that when the elongate members (202, 204) are arranged concentrically (e.g., one within another), a distal tip of the inner elongate member (204) may be advanced distally beyond a distal tip of the outer elongate member (202) and may puncture the pericardium to create access to the pericardial space. For example, in some variations, the length of the tubular member (212) of the inner elongate member (204) may be about 2 inches (5.08 cm) longer than the length of the outer elongate member (202). In these variations, the tubular member (212) of the inner elongate member (204) may be advanced through the lumen (224) of the outer elongate member (202) until the handle (214) of the inner elongate member (204) reaches the inlet of the lumen, at which point the distal tip of the inner elongate member (204) may extend about 2 inches (5.08 cm) from the distal tip of the outer elongate member (202). In some variations, the length of the tubular member (212) of the inner elongate member (204) may be between about 1.5 inches (3.81 cm) and about 2.5 inches (6.35 cm) longer than the length of the outer elongate member (202).

It may be beneficial to use the inner elongate member (204) to puncture the pericardium. For example, because the tubular member (212) of the inner elongate member (204) may have a smaller diameter than the tubular member of the outer elongate member (202), it may require less force to puncture the pericardium with the inner elongate member (204), which may reduce the likelihood of accidentally puncturing the heart. Additionally, puncturing the pericardium with a tubular member with a smaller diameter may also reduce the bleeding risk associated with an inadvertent needle stick. Furthermore, the smaller diameter of the tubular member of the inner elongate member (204) may provide it with flexibility that, upon entering the pericardial space, may allow the inner elongate member to be partially deflected away from the heart (as will be described in more detail below), which may decrease the risk of heart lacerations.

When the access devices described here are used to access the pericardial space using a sub-xiphoid approach, the inner and outer elongate members may be sized such that the tubular member of each of the inner and outer elongate members may reach the pericardium from a sub-xiphoid access point. In some variations, the tubular member (212) of the inner elongate member (204) may be at least about 6 inches (15.24 cm) in length. In some of these variations, the inner elongate member (204) may be at least about 8 inches (20.32 cm) in length. In some variations, the tubular member (212) of the inner elongate member (204) may be at least about 8 inches (20.32 cm) in length. In some of these variations, the inner elongate member (204) may be at least about 10 inches (25.40 cm) in length. Similarly, in some variations, the tubular member (208) of the outer elongate member (202) may be at least about 3.5 inches (8.89 cm) in length. In some of these variations, the outer elongate member (202) may be at least about 4 inches (10.16 cm) in length. In some variations, the tubular member (208) of the outer elongate member (202) may be at least about 6 inches (15.24 cm) in length. In some of these variations, the outer elongate member (202) may be at least about 6.5 inches (16.51 cm) in length. The difference in length between the outer and inner elongate members (202, 204) may enable a user to puncture the pericardium with the inner elongate member (204) before the distal tip of the outer elongate member (202) reaches it.

In some instances, it may be desirable to limit the distance that the tip of the inner elongate member (204) extends beyond the tip of the outer elongate member (202) during advancement of the access device (200) through tissue. Limiting this extension of the inner elongate member (204) may reduce the likelihood that the inner elongate member (204) will be damaged (e.g., by kinking) if the tip of inner elongate member (204) catches on tissue during advancement. In some variations, the inner elongate member (204) and the outer elongate member (202) may be advanced with the distal tip of the inner elongate member (204) flush with the distal tip of the outer elongate member (202). In other variations, the inner elongate member (204) and the outer elongate member (202) may be advanced with the distal tip of the inner elongate member (204) proximal to the distal tip of the outer elongate member (202). As mentioned above, a locking member (206) may be configured to maintain this relative positioning during advancement of the access device (200).

In other variations, it may be desirable for the tip of the inner elongate member (204) to extend slightly beyond the tip of the outer elongate member (202) during advancement of the access device. In these variations, the smaller outer diameter of the tubular member (212) of inner elongate member (204) may encounter less resistance when being advancing through tissue relative to the outer elongate member (202), which may facilitate advancement of the access device (200). Additionally, by limiting the extension of the distal tip of the inner elongate member (204), the outer elongate member (202) may reinforce the distal tip of the inner elongate member (204) (e.g., to help minimize bending or kinking of the inner elongate member (204)) and may help facilitate advancement of the access device (200). Accordingly, the distal tip of the inner elongate member (204) may extend any suitable distance beyond the distal tip of the outer elongate member (202) during advancement of the access device (200). In some embodiments, the distal tip of the inner elongate member (204) may extend beyond the distal tip of the outer elongate member (202) by a distance less than about 0.3 inches (7.62 mm). In some of these variations, the distal tip of the inner elongate member (204) may extend beyond the distal tip of the outer elongate member (202) by a distance less than or equal to about 0.2 inches (5.08 mm). In some variations, the distal tip of the inner elongate member (204) may extend beyond the distal tip of the outer elongate member (202) by a distance of about 0.1 inches (2.54 mm) to about 0.2 inches (5.08 mm). As mentioned above, a locking member (206) may be configured to maintain this relative positioning during advancement of the access device (200).

The distal tips of the inner and outer elongate members (204, 202) may be configured to facilitate the formation of and/or enlargement of a tissue opening. For example, in some variations, the tips of each of the inner and outer elongate members (204, 202) have a bevel or edge configured to pierce tissue. In some of these variations, the inner elongate member (204) has a beveled tip, and the outer elongate member (202) has a beveled tip. In these variations, the angle of the bevel of the inner elongate member (204) may be the same as or may be different from the angle of the bevel of the outer elongate member (202). In others of these variations, the tips of one or both of the inner and outer elongate members (204, 202) have a circumferential or semi-circular cutting edge. In these variations, the circumferential or semi-circular cutting edge may be configured such that the tubular member is beveled between the inner diameter of the tubular member and the outer diameter of the tubular member.

Figure 4A:
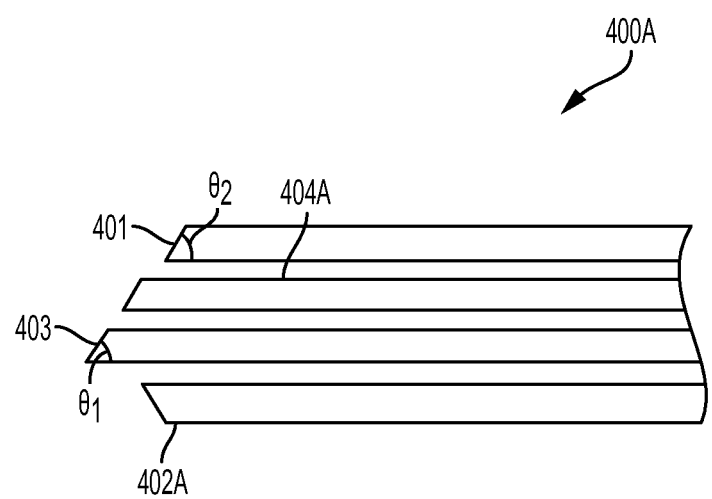
FIGS. 4A-4D depict longitudinal cross-sectional views of distal ends of variations of the access devices described here.
Figure 4B:
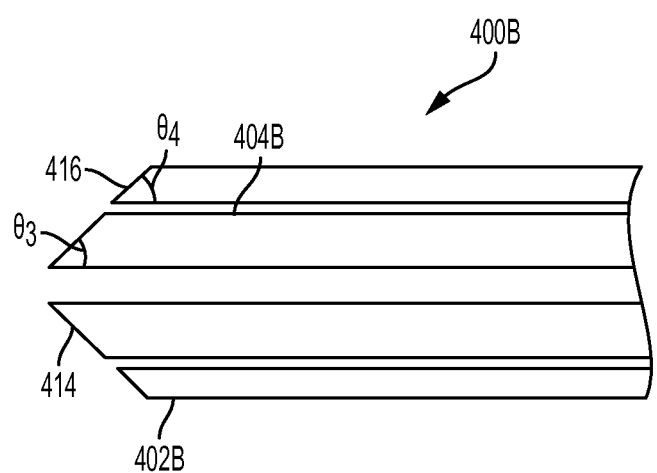

For example, FIG. 4A illustrates a variation of the access device (400A) where the tubular member of the inner elongate member (404A) has a beveled distal tip (403) and the tubular member of the outer elongate member (402A) has a distal tip with a circumferential or semi-circular cutting edge (401). In some variations, the bevel angle ($\theta_1$) of the beveled distal tip (403) may be the same as the bevel angle ($\theta_2$) of the circumferential or semi-circular cutting edge (401), although it should be appreciated that in other instances, the bevel angles ($\theta_1$, $\theta_2$) may be different. In other variations, the tubular members of the inner and outer elongate members may each include a circumferential or semi-circular cutting edge. FIG. 4B depicts yet another a variation of an access device (400B) where the tubular member of the inner elongate member (404B) has a distal tip with a first circumferential or semi-circular cutting edge (414), and the tubular member of the outer elongate member (402B) has a distal tip with a second circumferential or semi-circular cutting edge (416). In some variations, the bevel angle ($\theta_3$) of the first circumferential or semi-circular cutting edge (414) may be the same as the bevel angle ($\theta_4$) of the second circumferential or semi-circular cutting edge (416), although it should be appreciated that, in other instances, the bevel angles ($\theta_3$, $\theta_4$) may be different. In some variations, the distal tips of the outer and inner elongate members (404B, 402B) may be machined together, while the outer and inner elongate members (404B, 402B) are concentrically arranged to create a smooth transition between the inner and outer elongate members (404B, 402B).

Figure 4C:
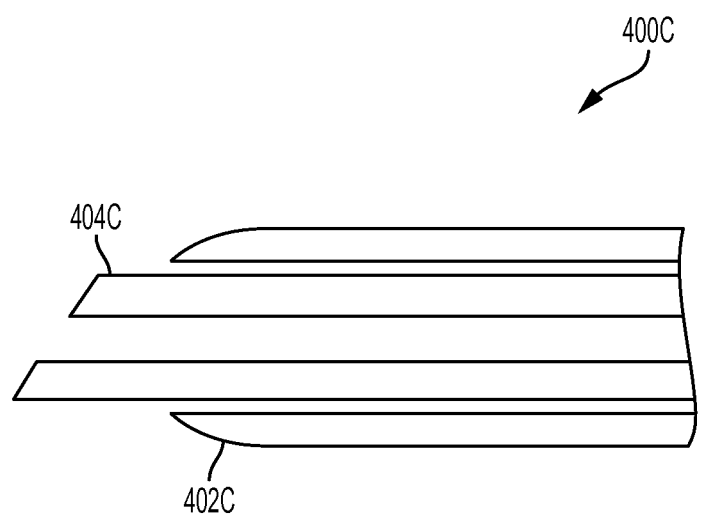
Figure 4D:
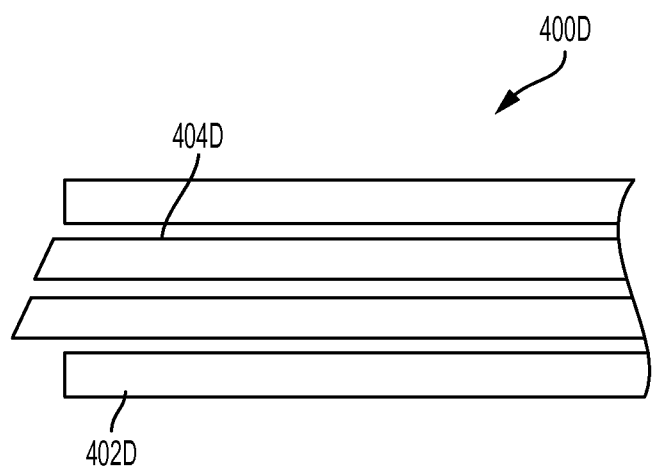

In other variations, the distal tip of the outer elongate member may be blunt. In some of these variations, the distal tip of the outer elongate member may be rounded. For example, FIG. 4C depicts another variation of an access device (400C) in which the tubular member of the outer elongate member (402C) has a rounded distal tip. The rounded portion of the distal tip of the outer elongate member (402C) may comprise any radius of curvature and may facilitate expansion of a tissue opening when the outer elongate member (402C) is advanced along the inner elongate member (404C). FIG. 4D illustrates another embodiment of an access device (400D) in which the tubular member of the outer elongate member (402D) has a flat distal tip (e.g., has a distal surface perpendicular to the longitudinal axis of the tubular member). While the inner elongate member (404C, 404D) is shown in FIGS. 4C and 4D as having a beveled distal tip, it should be appreciated that, in these variations, the inner elongate member (404C, 404D) may be configured with any suitable tissue-piercing tip (e.g., a circumferential or semi-circular cutting edge or the like).

Turning back to FIG. 3A, as mentioned above, the access device (200) may comprise a locking member (206) configured to releasably constrain the relative movement of the inner and outer elongate members (202, 204). In some embodiments, the locking member (206) may temporarily fix the position of the outer elongate member (202) in relation to the position of the inner elongate member (204). In other embodiments, the locking member (206) may be configured to limit the relative movement between the inner elongate member (204) and the outer elongate member (202). For example, in some variations, the locking member (206) may be positioned to limit the amount that the inner elongate member (204) may be advanced into the lumen (224) of the outer elongate member (202), as will be described in more detail below.

Generally, the locking member (206) may comprise a body (216) that is configured to be temporarily connected to one or both of the inner elongate member (204) and the outer elongate member (202). The body (216) may be made from any suitable material (e.g., one or more foams, polymers, plastics, metals, combinations thereof, and the like), and may have any suitable cross-sectional shape (e.g., circular, square, oval, triangular, hexagonal, or the like). In some variations, the body (216) may be configured to fit at least partially around one or more portions of the inner and/or outer elongate members. For example, in the variation of the locking member (206) shown in FIGS. 2 and 3A, the locking member (206) may comprise a lumen (230) extending through its body (216). In these variations, the lumen (230) may be sized and configured such that the tubular member (212) of the inner elongate member (204) may be positioned within the lumen (230). Accordingly, when the inner elongate member (204) and the outer elongate member (202) are concentrically arranged, the tubular member (212) of the inner elongate member (204) may be positioned through the lumen (230) of the locking member (206) to position the body (216) between the handle (210) of the outer elongate member (202) and the handle (214) of the inner elongate member (204), such as shown in FIG. 2. When the body (216) of the locking member (206) is positioned between the handles of the elongate members, the body (216) may act to maintain a minimum space between the handles of the inner and outer elongate members. For example, the tubular member (212) of the inner elongate member (204) may be advanced through the lumen (224) of the outer elongate member (202) until a distal end of the locking member (206) contacts the handle (210) of the outer elongate member (202) and a proximal end of the locking member (206) contacts the handle (214) of the inner elongate member (204). At this point, the locking member (206) may prevent further advancement of the inner elongate member (204) relative to the outer elongate member (202).

In variations where the locking member (206) comprises a lumen (230), the tubular member (212) of the inner elongate member (204) may be inserted into and removed from the lumen (230) in any suitable manner. In some variations, the locking member (206) may be connected to and/or removed from the inner elongate member (204) by axially sliding the locking member (206) relative to the tubular member (212). Additionally or alternatively, the locking member (206) may be configured to allow the locking member (206) to be radially connected to and/or disconnected from the tubular member (212). For example, in some variations, the locking member (206) may comprise a slit or a channel extending from an external surface of the body (216) to the lumen (230), which may be configured to allow the tubular member (212) to pass through the slit or channel to allow the locking member (206) to be radially connected to or disconnected from the inner elongate member (204). In some variations, the slit or channel may temporarily expand (e.g., the slit may expand into a channel, or a channel may expand into a larger channel) to accommodate the tubular member (212), and in some instances, may be configured to return to its original configuration when the tubular member (212) has passed therethrough (e.g., once the tubular member (212) has been positioned in the lumen (230) or once the tubular member (212) has been released from the locking members. In other variations, the locking member (206) may be configured to have one or more frangible portions that may be broken to allow the locking member (206) to be radially disconnected from the inner elongate member (204). In some variations, one or more frangible portions may be configured to break the locking member (206) into two or more separate pieces. In other variations, a frangible portion of the locking member (206) may be configured to break to form a slit or channel between the lumen (230) and an external surface of the body (216).

In some variations, the locking members described here may be configured to temporarily fix the locking member relative to one or both of the elongate members. In variations where the locking member comprises a lumen (e.g., the lumen (230) of the locking member (206) shown in FIGS. 2 and 3A), the lumen may be configured to form a frictional hold with the tubular member (212) of the inner elongate member (204) when the tubular member (212) is positioned in the lumen. In some variations, the diameter of the lumen may be smaller than the outer diameter of the tubular member (212), such that the lumen expands to accommodate the tubular member (212). The lumen may be biased toward its unexpanded configuration, which may in turn frictionally engage and hold the tubular member (212). In these variations, in order to move the tubular member (212) relative to the locking member (206), a user may apply a force to the inner elongate member (204) and/or the locking member (206) that is large enough to overcome the frictional engagement between the lumen of the locking member (206) and the tubular member (212). Additionally or alternatively, the interior surface of the lumen of the locking member (206) may be textured and/or include a textured lining to increase the frictional forces between the lumen of the locking member (206) and the tubular member (212) of the inner elongate member (204).

Additionally or alternatively, in some variations, the locking members described here may comprise one or more connectors configured to releasably connect the locking member to one or more of the inner and outer elongate members. For example, in the variation of the access device (200) shown in FIGS. 2 and 3A, the locking member (206) may comprise a proximal connector (218) and a distal connector (220). Generally, the proximal connector (218) may be configured to connect the locking member (206) to a portion of the inner elongate member (204) (e.g., to the handle (214) of the inner elongate member (204)), and the distal connector (218) may be configured to connect the locking member (206) to the outer elongate member (202) (e.g., to the handle (210) of the outer elongate member (202)). When the proximal connector (218) is connected to the inner elongate member (204) and the distal connector (220) is connected to the outer elongate member (202), the locking member (206) may prevent relative axial movement between the inner elongate member (204) and the outer elongate member (202).

While the locking member (206) is shown in FIGS. 2 and 3A as having two connectors (e.g., a proximal connector (218) and distal connector (220)), it should be appreciated that, in some instances, the locking member (206) may include only one connector and in other instances may not comprise any connector. For example, in some variations, the locking member (206) may comprise only a proximal connector (218) configured to connect the locking member (206) to a portion of the inner elongate member (204). In these variations, the locking member (206) may act as a stop to limit the movement of the inner elongate member (204) distally relative to the outer elongate member (202) (e.g., the inner elongate member (204) and locking member (206) may be advanced together until a distal portion of the locking member (206) engages a proximal portion of the outer elongate member (202) and prevents further distal movement of the inner elongate member (204)), but may allow the inner elongate member (204) and the locking member (206) to be freely withdrawn relative to the outer elongate member (202).

In other variations, the locking member (206) may comprise only a distal connector (218) configured to connect the locking member (206) to a portion of the outer elongate member (202). In these variations, the locking member (206) may act as a stop to limit the movement of the inner elongate member (204) distally relative to the outer elongate member (202) (e.g., the inner elongate member (204) may be advanced relative to the outer elongate member (202) and the locking member (206) until the handle (214) or another portion of the inner elongate member (204) engages a proximal portion of the locking member (206) and prevents further distal movement of the inner elongate member (204)). In some of these variations, the locking member (206) may comprise a lumen (230) configured to frictionally hold the inner elongate member (204), such that the positions of the inner elongate member (204) and outer elongate member (202) are temporarily fixed relative to each other. In other variations, the inner elongate member (204) may be freely withdrawn relative to the locking member (206) and the outer elongate member (202).

In variations where the locking members described here comprise one or more connectors, the connectors may be any suitable connector. In some variations, the connectors may be a luer lock connector or a luer slip/slip-tip connector. For example, FIG. 5A shows one such variation of a locking member (500). As shown there, the locking member (500) may comprise a body (502), a proximal luer lock connector (504), and a distal luer lock connector (506). While shown in FIG. 5A as having both a proximal luer lock connector (504) and a distal luer lock connector (506), it should be appreciated that, in some instances, the locking member (500) may include only a proximal luer lock connector (504) or may include only a distal luer lock connector (506). In some variations, the body (502) of the locking member (500) may comprise a lumen (509) extending therethrough, such as described in more detail above. In some of these variations, the locking member (500) may further comprise a longitudinal channel (e.g., channel (510) as shown in FIG. 5A) or a slit that may facilitate radial connection or removal of the locking member (500) from the inner elongate member. In other variations, the locking member (500) may comprise one or more frangible portions to facilitate removal of the locking member (500).

In variations that include a proximal luer lock connector (504), the proximal luer lock connector (504) may be configured to releasably connect to a counterpart luer lock connector on the inner elongate member (e.g., by rotating the locking member (500) relative to the inner elongate member). For example, FIG. 5A shows a variation of the inner elongate member (204) described above with respect to FIGS. 2 and 3A, in which the handle (214) of the inner elongate member (204) comprises a luer lock connector (512). The luer lock connector (512) of the inner elongate member (204) and the proximal luer lock connector (504) of the locking member may be a male fitting and a female fitting, respectively, or may be a female fitting and a male fitting, respectively. Similarly, in variations that include a distal luer lock connector (506), the distal luer lock connector (506) may be configured to releasably connect to a counterpart luer lock connector on the outer elongate member (e.g., by rotating the locking member (500) relative to the outer elongate member). For example, FIG. 5A shows a variation of the outer elongate member (202) described above with respect to FIGS. 2 and 3A, in which the handle (210) of the outer elongate member (202) comprises a luer lock connector (514). The luer lock connector (514) of the outer elongate member (202) and the proximal luer lock connector (506) of the locking member may be a male fitting and a female fitting, respectively, or may be a female fitting and a male fitting, respectively.

In variations where the inner elongate member (204) and the outer elongate member (202) each include a luer lock connector, the luer lock connector (512) of the inner elongate member (204) may be configured to releasably connect to the luer lock connector (514) of the outer elongate member (202). For example, the luer lock connector (512) of the inner elongate member (204) and the luer lock connector (514) of the outer elongate member (202) may be a male fitting and a female fitting, respectively, or may be a female fitting and a male fitting, respectively. This may allow the inner elongate member (204) to be connected to the outer elongate member (202) after the locking member (500) is disconnected from the access device. For example, in some instances, the locking member (500) may be connected to both the inner elongate member (204) and the outer elongate member (202). Specifically, the tubular member (212) of the inner elongate member (204) may be advanced through the lumen (224) of the outer elongate member (202), and the locking member (500) may be positioned between the handles of the inner and outer elongate members (e.g., by advancing the tubular member (212) of the inner elongate member (204) through a lumen (509), by moving the tubular member (212) of the inner elongate member (204) radially through a slit or channel of the locking member, or the like). The proximal luer lock connector (504) may be connected to the luer lock connector (512) of the inner elongate member (204), and the distal luer lock connector (506) may be connected to the luer lock connector (514) of the outer elongate member (202) to hold the access device in a delivery configuration, such as one or more of the delivery configurations described above. The access device may be advanced and/or manipulated in the delivery configuration, and the locking member (500) may be disconnected from the inner and outer elongate members to allow the inner elongate member (204) to be advanced relative to the outer elongate member (202). In some variations, the inner elongate member (204) may be advanced until the luer lock connecter (512) of the inner elongate member (204) reaches the luer lock connector (514) of the outer elongate member (202) to position the access device in a piercing configuration as described above. At this point, the luer lock connecter (512) of the inner elongate member (204) may be connected to the luer lock connector (514) of the outer elongate member (202) to temporarily hold the access device in the piercing configuration. While the connectors described in relation to FIG. 5A are depicted as luer lock connectors, it should be appreciated that the connectors described there may alternatively be luer slip/slip-tip connectors.

Figure 5B:
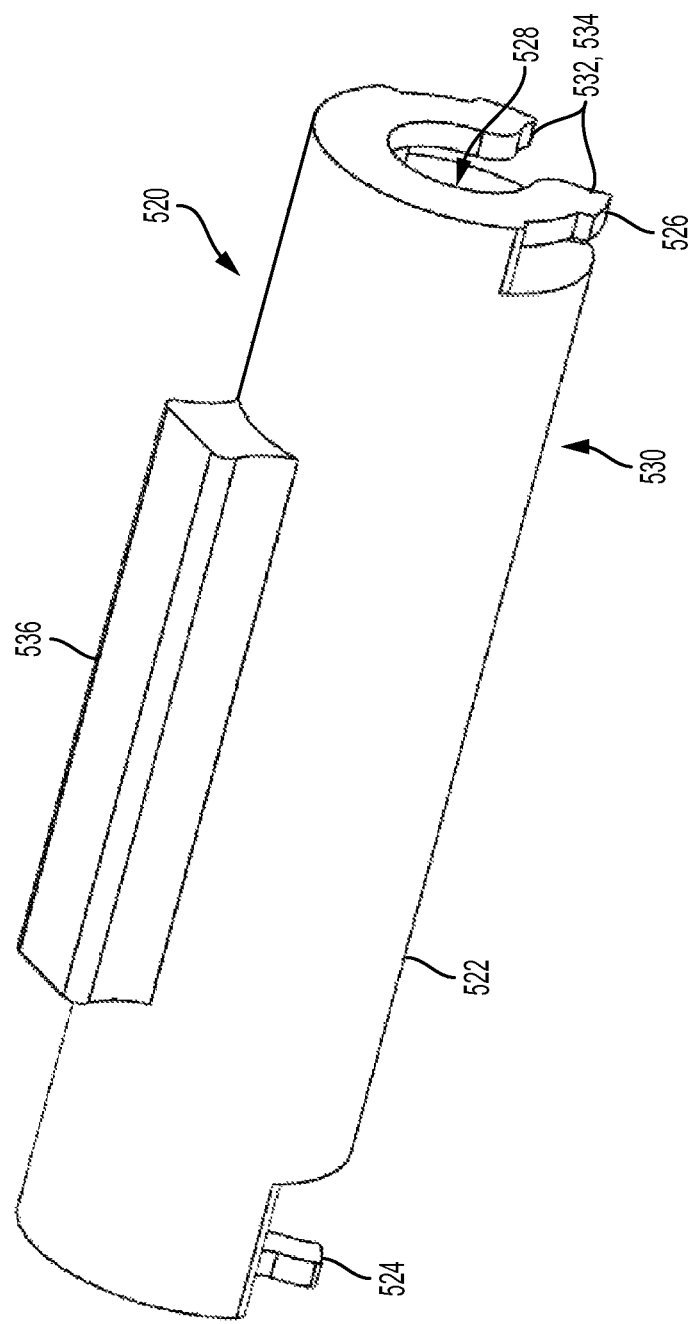

In some variations of the locking members described here, the locking member may include one or more snap-fit connectors. For example, FIG. 5B shows a variation of a locking member (520) comprising a body (522) and snap-fit connectors (524, 526). In some variations, the locking member (520) may comprise a lumen (528) extending therethrough, such as described in more detail above. In some of these variations, the locking member (520) may further comprise a longitudinal channel (e.g., channel (530) as shown in FIG. 5B) or a slit that may facilitate radial connection or removal of the locking member (520) from the inner elongate member, such as described in more detail above. Additionally, the locking member (520) may further comprise a handle (536) to facilitate grasping of the locking member (520) during connection or removal of the locking member (520). The locking member (520) is shown in FIG. 5B as having a proximal snap-fit connector (524) and a distal snap-fit connector (526), although it should be appreciated that the locking member (520) need not have both proximal and distal snap-fit connectors. In some variations, the locking member (520) comprises a proximal snap-fit connector (524) but not a distal snap-fit connector. In some of these variations, the locking member (520) may comprise a distal connecter that may be a luer lock connector, a luer slip/slip-tip connector, or the like. In others of these variations, the locking member (520) may not have a distal connector. In some variations, the locking member (520) comprises a distal snap-fit connector (526) but not a proximal snap-fit connector. In some of these variations, the locking member (520) may comprise a proximal connecter that may be a luer lock connector, a luer slip/slip-tip connector, or the like. In others of these variations, the locking member (520) may not have a proximal connector.

Each snap-fit connector (524, 526) may comprise a pair of arms (532, 534). The arms (532, 534) may be configured to at least partially surround a portion of the inner or outer elongate member to grip the inner or outer elongate member. For example, in some variations where the locking member (520) comprises a proximal snap-fit connector (524), the arms (532, 534) of the proximal snap-fit connector (524) may be configured to at least partially surround the handle (214) of the inner elongate member (204) and to grip the handle (214). Similarly, in some variations where the locking member (520) comprises a distal snap-fit connector (526), the arms (532, 534) of the distal snap-fit connector (526) may be configured to at least partially surround the handle (210) of the outer elongate member (202) and to grip the handle (210). Similarly, the snap-fit connectors may be removed from the access device by pulling the locking member (520) radially away from the inner and outer elongate members such that the arms (532, 534) are temporarily flexed to release the securement with the inner and/or outer elongate members.

Figure 5C:
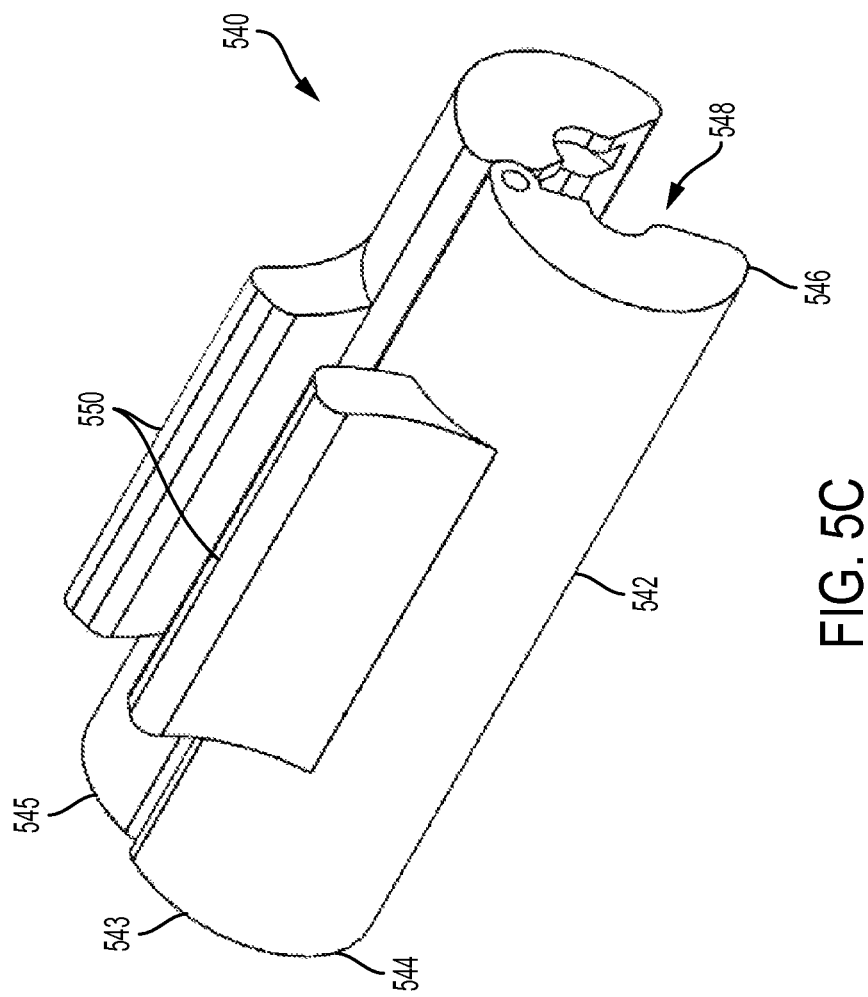

In still other variations, the locking members described here may comprise a hinged clip connector. For example, FIG. 5C depicts another embodiment of a locking member (540) as described here. As shown there, the locking member (540) comprises a clip (542) having a proximal connector portion (544) and a distal connector portion (546). The clip (542) may have a first jaw (543) and a second jaw (545) that may rotate relative to each other via a hinging mechanism. In some variations, the first jaw (543) and the second jaw (545) may be formed separately and pivotably connected to each other (e.g., via a pin joint or the like), while in other variations the first jaw (543) and second jaw (545) may be formed integrally and may rotate via deflection of material connecting the first and second jaws (e.g., via a living hinge). The first jaw (543) and the second jaw (545) define a lumen (548) extending therethrough, and the first and second jaws may be rotated relative to each other to increase the size of the lumen (548), which may facilitate disconnection of the locking member (540) from the access device. Conversely, rotation of the first jaw (543) toward the second jaw (545) may cause one or more portions of the access device to be clamped by the clip (542). For example, a proximal portion of the clip (542) may form a proximal connector (544), which may be configured to clip to a portion of the inner elongate member (204) (e.g., the handle (214) of the inner elongate member) when the first jaw (543) is rotated toward the second jaw (545). Similarly, a distal portion of the clip (542) may form a distal connector (546), which may be configured to clip to a portion of the outer elongate member (202) (e.g., the handle (210) of the outer elongate member) when the first jaw (543) is rotated toward the second jaw (545). In some variations, each of the first jaw (543) and the second jaw (545) may comprise a handle (550), such that the handles (550) may be squeezed together, to rotate the first jaw (543) away from the second jaw (545) (which may in turn release the clip (542) from the access device). It should be appreciated that, in some instances, the locking member may comprise two clips, wherein a first clip forms a proximal connector, and a second clip forms a distal connector. In these variations, the clips may be individually actuated to connect or disconnect the clips from the inner or outer elongate members.

As mentioned above, the inner elongate member and outer elongate member may be moveable between a delivery configuration and a piercing configuration. The locking members described above may be used to maintain the access device in the delivery configuration or to prevent the access device from being moved from the delivery configuration to the piercing configuration. For example, when the locking member comprises proximal and distal connectors, the access device may be held in the delivery configuration when the proximal connector is connected to the inner elongate member, and the distal connector is connected to the outer elongate member. In other variations (e.g., variations where the locking member includes only one connector or does not include any connectors), the locking member may prevent the access device from being moved between the delivery configuration and the piercing configuration. In these variations, the inner elongate member may be advanced through the outer elongate member until the locking member engages both the inner and outer elongate members and prevents further advancement of the inner elongate member. The access device may be configured such that the access device is in the delivery configuration when the locking member engages both the inner and outer elongate members, and thus the locking member may prevent further advancement of the inner elongate member toward the piercing configuration. To maintain the access device in the delivery configuration or to prevent advancement of the inner elongate member past the delivery configuration, the locking member may have any suitable length. For example, in some variations the locking member may be between about 1.5 inches (3.81 cm) and about 3 inches (7.62 cm). In some of these variations, the locking member may be about 2 inches (5.08 cm) in length.

Figure 5D:
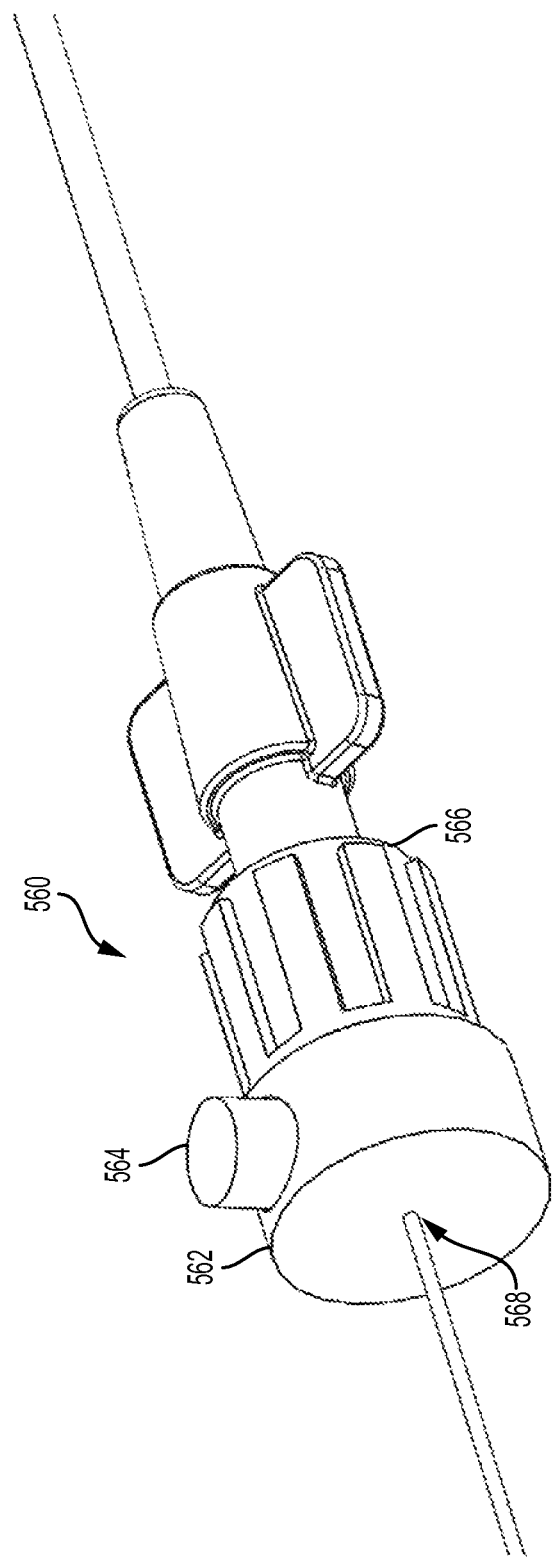
Figure 5E:
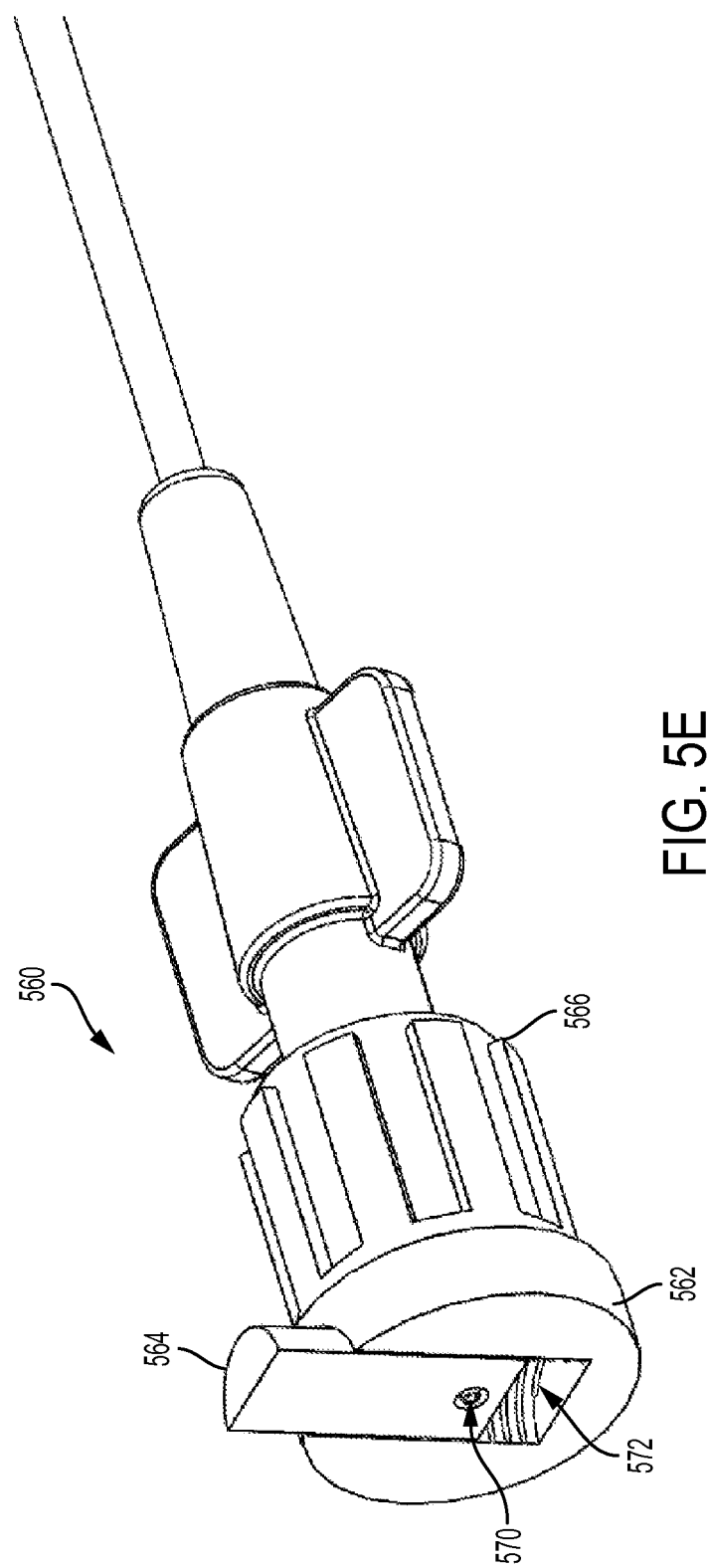

FIGS. 5D and 5E illustrate yet another variation of a locking member (560) suitable for use with the access devices described here. As shown there, the locking member (560) may comprise a cylindrical body (562) with a lumen (568) extending therethrough and a connector peg (564). In some variations, the locking member (560) may comprise a distal connector (566). In these variations, the distal connector (566) may be configured to releasably connect the locking member (560) to the outer elongate member (e.g., to a corresponding connector on the handle of the outer elongate member). The connector (566) may be any suitable connector, such as a luer lock, a luer slip/slip-tip connector, a snap-fit connector, a clip, or the like. In other variations, the locking member (560) may be integrally formed with or otherwise permanently connected to the handle of the outer elongate member.

The connector peg (564) may be configured to releasably fix the locking member (560) relative to the inner elongate member. For example, the connector peg (564) may comprise a lumen (570) extending through connector peg (564), and may be moveable within the cylindrical body (562) between a first position in which the lumen (570) of the connector peg (564) is aligned with the lumen (568) of the cylindrical body (562) and a second position in which the lumen (570) of the connector peg (564) is misaligned with the lumen (568) of the cylindrical body (562). In some variations, the locking member (560) may comprise a spring (572) positioned and configured to bias the connector peg (564) away from the first position.

To connect the locking member (560) to the inner elongate member, the connector peg (564) may be moved to the first position (e.g., by pushing the connector peg (564) to compress the spring (572)). When the lumen (570) of the connector peg (564) is aligned with the lumen (568) of the cylindrical body (562), the tubular member of the inner elongate member may be advanced through the lumens 568, 570). When force holding the connector peg (564) in its first position is removed, the spring (572) may push the connector peg (564) away from the first position, which in turn may cause the connector peg (564) to press against the portion of the inner elongate member positioned in the lumen (570) of the connector peg (564). This may cause a frictional engagement between the connector peg (564) and the inner elongate member, which may in turn resist advancement or withdrawal of the inner elongate member through the lumen (568) of the cylindrical body (562). The connector peg (564) may again be moved to the first position to allow the inner elongate member to slide relative to the outer elongate member.

In the embodiment depicted in FIGS. 5D and 5E, the locking member (560) may be engaged and disengaged to connect the locking member (560) to the inner elongate member along different portions of the inner elongate member. Thus, it may be desirable to provide a user with an indication that the access device is in a particular configuration (e.g., a delivery configuration as described above). Accordingly, in some variations, the inner elongate member may comprise one or more markings configured to indicate the relative positioning between the inner and outer elongate members. For example, the tubular member of the inner elongate member may comprise a first marking, wherein the first marking is positioned such that when the marking reaches a proximal inlet of the lumen (568) of the cylindrical body (562), the access device is positioned in the delivery configuration. In some variations, the tubular marking may comprise a second marking, which may indicate that the distal tip of the inner elongate member has reached a certain distance beyond the distal tip of the outer elongate member when the second marking reaches the inlet of the lumen (568) of the cylindrical body (562). The markings may be colored markings on the tubular member, notches in the tubular member, or the like.

Figure 6:
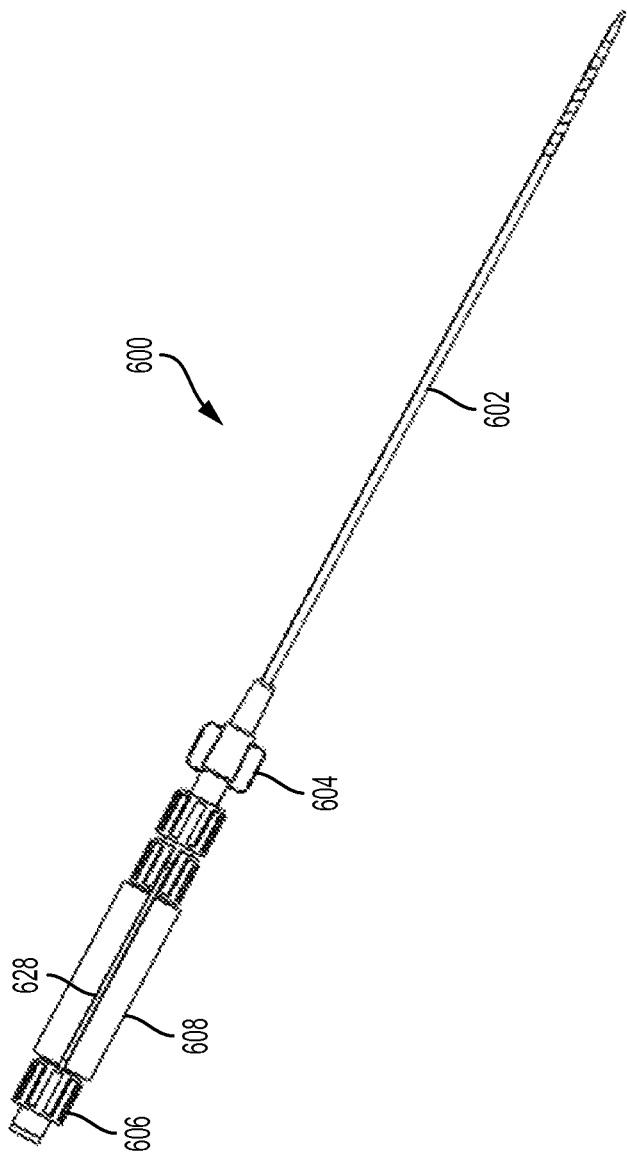
FIG. 6 depicts a perspective view of an embodiment of an access device.
Figure 7A:
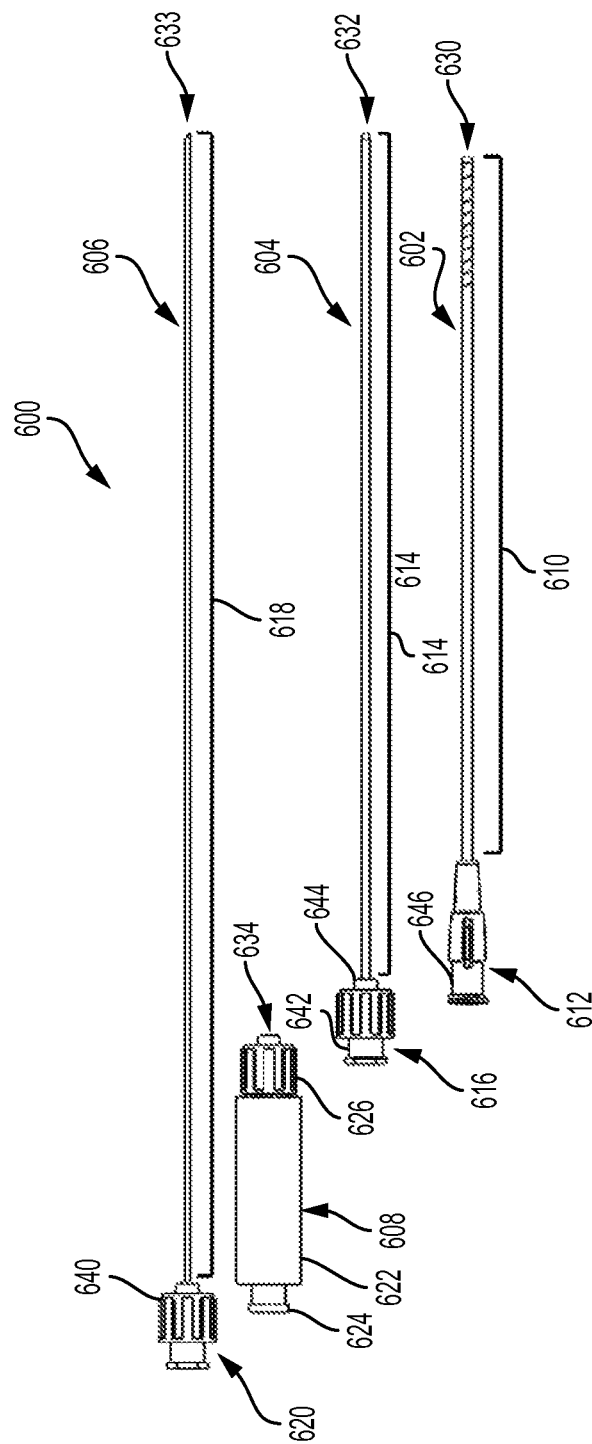
FIGS. 7A and 7B depict an exploded view and a cross-sectional view of the tubular members, respectively, of the access device of FIG. 6.
Figure 7B:
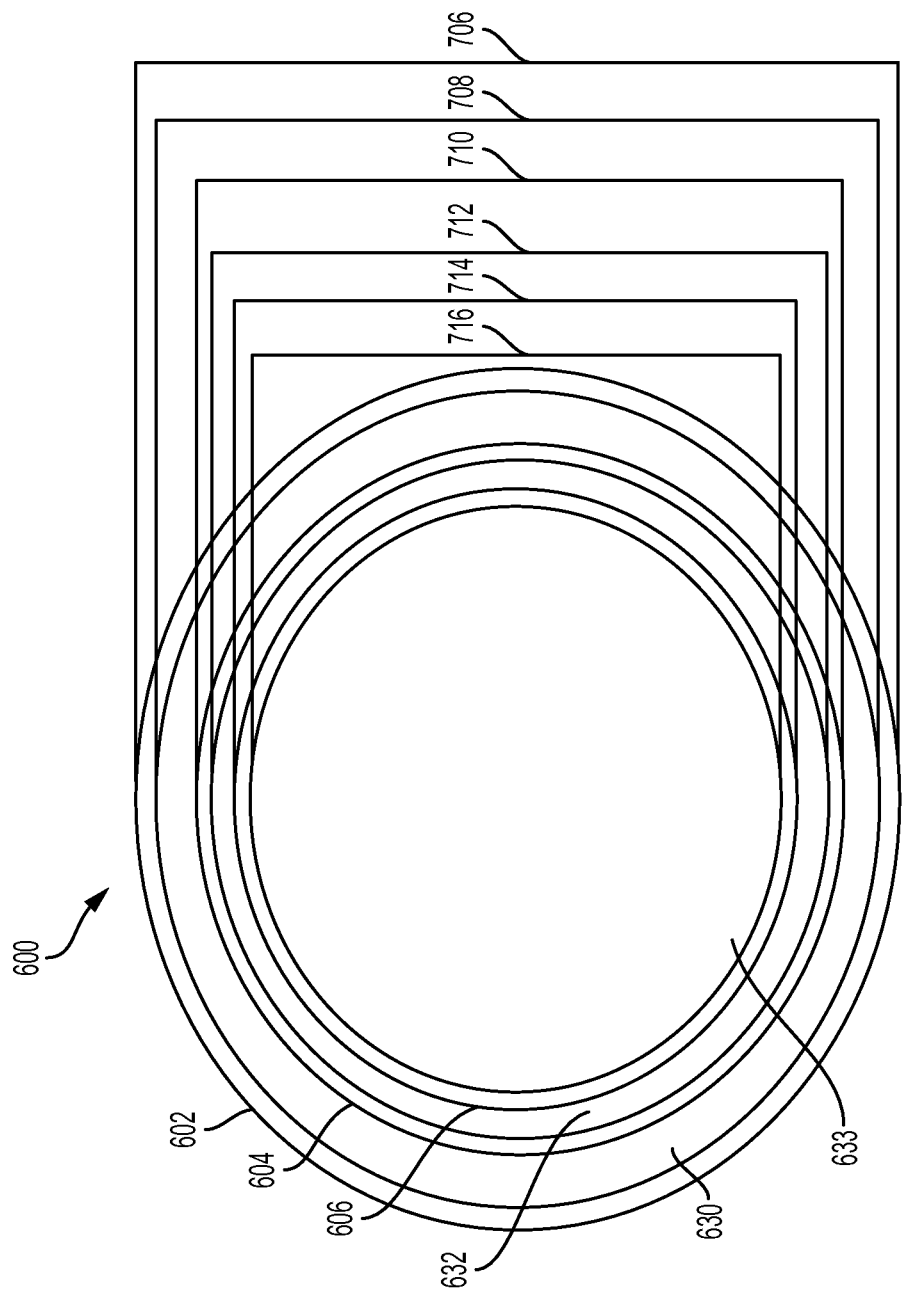

FIGS. 6 and 7A-7B depict another embodiment of the access devices described here. FIG. 6 depicts a perspective view of an access device (600) in an assembled configuration. FIG. 7A shows an exploded view of the access device (600) disassembled to better illustrate its components. As shown there, the access device (600) may comprise a first outer elongate member (602), a second intermediate elongate member (604), and a third inner elongate member (606). The outer elongate member (602) may comprise a lumen (630) extending therethrough, and at least a portion of the intermediate elongate member (604) may be sized to fit within the lumen (630) of the outer elongate member (602). The intermediate elongate member (604) may comprise a lumen (632) extending therethrough, and at least a portion of the inner elongate member (606) may be sized to fit within the lumen (632) of the intermediate elongate member (604). When in the assembled configuration shown in FIG. 6, the inner (606), intermediate (604), and outer (602) elongate members may be concentrically arranged such that a portion of the inner elongate member (606) extends at least partially through the lumen (632) of the intermediate elongate member (604), and a portion of the intermediate elongate member (604) extends at least partially through the lumen (630) of the outer elongate member (602). The inner elongate member (606) may comprise a distal tip configured to pierce tissue, such that the inner elongate member (606) may be advanced into tissue to pierce or otherwise puncture the tissue. In some variations, the inner elongate member (606) may also comprise a lumen extending therethrough, but need not. In variations in which the inner elongate member (204) comprises a lumen, a guide wire or a fluid may be introduced into the pericardial space through the lumen of the inner elongate member (606), as will be described in more detail below.

Generally, the intermediate elongate member (604) may be temporarily connected to the outer elongate member (602) to fix the position of the intermediate elongate member (604) relative to the outer elongate member (602). In some variations, the intermediate elongate member (604) may be configured to releasably connect to the outer elongate member (602). For example, the intermediate elongate member (604) may comprise a connector configured to releasably connect to a corresponding connector on the outer elongate member (602). Additionally or alternatively, the access device (600) may comprise a locking member (not shown), such as those described above, which may be configured to releasably connect the intermediate elongate member (604) to the outer elongate member (602).

Optionally, the access device (600) may further comprise a locking member (608) generally configured to releasably constrain the position of the inner elongate member (606) relative to the intermediate elongate member (604) and/or the outer elongate member (602). The locking member (608) may releasably engage the inner elongate member (606), the intermediate elongate member (604), and/or the outer elongate member (602) to limit relative movement between the inner elongate member (606) and the outer and/or intermediate elongate members (602, 604), and may be disengaged to allow for relative movement between the inner elongate member (606) and the outer and intermediate elongate members (602, 604). When the locking member (608) is engaged, the locking member (608) may limit relative movement between the inner elongate member (606) and the outer and/or intermediate elongate members (602, 604) in a number of ways. For example, in some variations, the locking member (608) may axially fix the position of the inner elongate member (606) relative to the position of the intermediate elongate member (604) (e.g., the inner elongate member (606) may be prevented from sliding distally or proximally relative to the intermediate elongate member (604)) or may axially fix the position of the inner elongate member (606) relative to the position of the outer elongate member (602) (e.g., the inner elongate member (606) may be prevented from sliding distally or proximally relative to the outer elongate member (602)). In other variations, the locking member (608) may be configured to limit or otherwise prevent axial advancement of inner elongate member (606) beyond a certain point relative to the intermediate and/or outer elongate member (604, 602), but may allow for axial withdrawal of the inner elongate member (606) relative to the intermediate and/or outer elongate member (604, 602).

When the access device (600) is assembled, it may be moveable between a delivery configuration and a piercing configuration. In the delivery configuration, the inner elongate member (606), the intermediate elongate member (604), and the outer elongate member (602) may be concentrically arranged and may be further positioned to achieve a desired relative orientation between the tips of the three elongate members. For example, in some variations, the distal tip of the intermediate elongate member (604) may be positioned to extend beyond the distal tip of the outer elongate member (602) while the access device (600) is in the delivery configuration. In other variations, the distal tip of the intermediate elongate member (604) may be positioned to be flush with the distal tip of the outer elongate member (602) or may be positioned proximally of the distal tip of the outer elongate member (602) while the access device (600) is in the delivery configuration.

Additionally, in some variations, the distal tip of the inner elongate member (606) may be positioned to extend beyond the distal tips of both the intermediate elongate member (604) and the outer elongate member (602) when the access device is positioned in the delivery configuration. In some of these variations, it may be desirable to limit the distance that the inner elongate member (606) extends beyond the intermediate elongate member (604), as will be described in more detail below. In other variations, the distal tip of the inner elongate member (606) may be positioned to be flush with one or both of the distal tips of the intermediate elongate member (604) and the outer elongate member (602) while the access device (600) is in the delivery configuration. In still other variations, the distal tip of the inner elongate member (606) may be positioned to be flush with one or both of the distal tips of the intermediate elongate member (604) and the outer elongate member (602) while the access device (600) is in the delivery configuration. In some instances, the outer, intermediate, and inner elongate members (602, 604, 606) may be temporarily fixed in the delivery configuration (e.g., via one or more locking members and/or direct connections between elongate members, as will be discussed in more detail below), which may allow the elongate members to be advanced and manipulated together toward the pericardium.

Similar to the embodiments of the access device (200) previously described, in some instances, the concentric arrangement of the outer, intermediate, and inner elongate members (602, 604, 606) may provide additional stiffness to the access device (600) and may facilitate advancement of the access device (600) through the body. For example, in some variations, the intermediate elongate member (604) may be stiffer than the inner elongate member (606), and the intermediate elongate member (604) may reinforce or otherwise limit bending of the inner elongate member (606) when the inner elongate member (606) is positioned in the lumen (632) of the intermediate elongate member (604). In other variations, however, the intermediate elongate member (604) may be more flexible than the inner elongate member (606) (e.g., when the inner elongate member is used to fill space between the inner elongate member (606) and the outer elongate member (602), as described in more detail below).

Similarly, in some variations, the outer elongate member (602) may be stiffer than the inner elongate member (606). The outer elongate member (602) may reinforce or otherwise limit bending of the inner elongate member (606) and/or intermediate elongate member (604) when the inner elongate member (606) and the intermediate elongate member (604) are positioned in the lumen (630) of the outer elongate member (602). In some of these variations, the outer elongate member (602) may also be stiffer than the intermediate elongate member (604). In other variations, the intermediate elongate member (604) may be stiffer than both the outer elongate member (602) and the inner elongate member (606). This variation may provide utility in instances where it is desirable to provide support to both a flexible inner elongate member (606) during advancement of the inner elongate member (606) toward the pericardium and a flexible outer elongate member (602) (e.g., a flexible tube) during advancement of the outer elongate member (602) to and through the pericardium.

When a distal end of the access device (600) is positioned near an external surface of the pericardium, the access device (600) may be moved from the delivery configuration to the piercing configuration. To move the access device (600) from the delivery configuration to the piercing configuration, the inner elongate member (606) may be advanced through the lumen (632) of the intermediate elongate member (604) to advance the inner elongate member (606) relative to the intermediate elongate member (604) and the outer elongate member (602). As the inner elongate member (606) is advanced, the distal tip of the inner elongate member (606) may be positioned to extend past the distal tips of the outer elongate member (602) and the intermediate elongate member (604). In variations where the distal tip of the inner elongate member (606) extends past the distal tips of the outer elongate member (602) and the intermediate elongate member (604) in the delivery configuration, the distance between the distal tip of the inner elongate member (606) and the tips of the intermediate and outer elongate members (604, 602) may be increased as the access device is moved from the delivery configuration to the piercing configuration. As the inner elongate member (606) is advanced toward the pericardium, the distal tip of the inner elongate member may puncture the pericardium to position the distal tip of the inner elongate member (606) in the pericardial space. When a locking member (608) is used to constrain the position of the inner elongate member (606)

relative to the intermediate and/or outer elongate members (604, 602), the locking member (608) may be disengaged to allow the access device (600) to be moved from the delivery configuration to the piercing configuration.

While the access device (600) is described above as being advanced in the delivery configuration, it should be appreciated that, in some instances, the access device (600) may be placed in the delivery configuration after the intermediate and/or outer elongate members (604, 602) have been advanced to a position near the pericardium. In some of these variations, the outer elongate member (602) may be advanced into the body a certain distance, the intermediate elongate member (604) may be advanced through the lumen (630) of the outer elongate member (604), and the inner elongate member (606) may be advanced through the lumen (632) of the intermediate elongate member (604) to position the access device (600) in the delivery configuration. In some variations, the intermediate elongate member (604) may be connected to the outer elongate member (602), and/or the locking member (608) may be connected to the access device to facilitate placement of the access device (600) in the delivery configuration, as will be discussed in more detail below. In other instances, the intermediate elongate member (604) and the outer elongate member (602) may be advanced together into the body, and the inner elongate member may then be advanced through the lumen (632) of the intermediate elongate member (604).

Turning to FIG. 7A, the access device (600) is depicted with the outer, intermediate, and inner elongate members (602, 604, 606) and the locking member (608) separated. As shown there, the outer elongate member (602) may comprise a tubular member (610) and a handle (612). The lumen (630) of the outer elongate member (602) may extend at least partially through the tubular member (610) and the handle (612). In some variations, the lumen (630) may extend between an inlet in the handle (612) and an outlet in a distal portion of the tubular member (610). The tubular member (610) may comprise a needle (e.g., a Tuohy needle, a beveled needle), a sheath, a hypotube, or any other suitable tubular device. The length and diameter of the tubular member (610) may vary based on anatomical considerations and other variables. In some embodiments, the distal end of the outer elongate member (602) may comprise a laser cut pattern, such as those discussed in more detail above.

The tubular member (610) and the handle (612) may be assembled in any suitable configuration. In some variations, the outer elongate member (602) may be constructed such that the handle (612) is connected to a proximal portion of the tubular member (610). In some of these embodiments, the tubular member (610) and the handle (612) may be integrally formed. In others of these embodiments, the handle (612) and the tubular member (610) may be constructed separately and attached to each other (e.g., via one or more adhesives, welding, or the like). In some variations, the outer elongate member (602) may be configured to temporarily connect to the locking member (608), the inner elongate member (606), or another device. In some of these variations, the handle (612) may comprise a connector. In these variations, the connector of the handle (612) may be configured to releasably connect to a corresponding connector on a locking member, the intermediate elongate member, or the like. In other variations, the tubular member (610) may comprise a connector, which may be configured to releasably connect to a corresponding connector on a locking member, the inner elongate member, or the like. The handle (612) may also be configured to facilitate manipulation of the tubular member (610) of the outer elongate member (602). For example, the handle (612) may comprise indentations, ridges, bumps, tabs or any other structural indication to facilitate placement of the hands of the user on the handle (612).

The intermediate elongate member (604) may also comprise a tubular member (614) and a handle (616). The tubular member (614) may be any of the variety of tubular members described above in relation to the outer elongate member (602) (e.g., a needle, sheath, hypotube, or the like). Furthermore, the length and diameter of the tubular member (614) may vary depending on anatomical considerations and other variables, such as discussed in more detail below. In some embodiments, the distal tip of the intermediate elongate member (604) may comprise a laser cut pattern, such as discussed in more detail above. The tubular member (614) and the handle (616) may be assembled in any suitable configuration. In some variations, the intermediate elongate member (604) may be constructed such that the handle (616) is connected to a proximal portion of the tubular member (614). In some of these embodiments, the tubular member (614) and the handle (616) may be integrally formed. In others of these embodiments, the handle (616) and the tubular member (614) may be constructed separately and attached to each other (e.g., via one or more adhesives, welding, or the like).

In some variations, the intermediate elongate member (604) may be configured to temporarily connect to the locking member (608), the inner elongate member (606), the outer elongate member (602), or another device. In these variations, the connector of the handle (616) may be configured to releasably connect to a corresponding connector on a locking member, the inner elongate member, the outer elongate member, or the like. In other variations, the tubular member (614) may comprise a connector, which may be configured to releasably connect to a corresponding connector on a locking member, the inner elongate member, or the like. In some variations, the intermediate elongate member (604) may comprise a first connector configured to releasably connect to a corresponding connector on the outer elongate member (602), and may comprise a second connector configured to releasably connect to a corresponding connector on the inner elongate member (606) and/or the locking member (608). The handle (616) may also be configured to facilitate manipulation of the tubular member (614) of the intermediate elongate member (604). For example, the handle (616) may comprise indentations, ridges, bumps, tabs, or any other structural indication to facilitate placement of the hands of the user on the handle (616). Additionally, in some variations, the handle (616) may be configured such that at least a portion of the handle (616) is sized such that it is prevented from entering the lumen (630) of the outer elongate member (602). In these variations, the handle (616) of the intermediate elongate member (604) may limit advancement of the intermediate elongate member (604) through the lumen (630) of the outer elongate member (602). In these variations, the intermediate elongate member (604) may be advanced into the lumen (630) (e.g., through the inlet of the lumen (630)) of the outer elongate member (602) until the handle (616) engages the inlet and prevents further advancement of the intermediate elongate member (604) relative to the outer elongate member (602).

The inner elongate member (606) may also comprise a tubular member (618) and a handle (620). The tubular member (618) may comprise a needle (e.g., a Tuohy needle, a beveled needle), a sheath, a hypotube, or any other suitable tubular device, such as discussed in more detail below.

Generally, the tubular member (618) comprises a distal tip configured to pierce tissue. For example, the distal tip may include one or more sharpened or beveled edges. The length and diameter of the tubular member (618) may vary based on anatomical considerations and other variables. In some embodiments, the distal tip of the inner elongate member (618) may comprise a laser cut pattern, as discussed in greater detail above. In some variations, the inner elongate member (606) may comprise a lumen (633). In some of these variations, the lumen (633) may extend at least partially through the tubular member (618) and the handle (620). In some variations, the lumen (633) may extend between an inlet in the handle (620) and an outlet in a distal portion of the tubular member (618).

The tubular member (618) and the handle (620) may be assembled in any suitable configuration and manner, such as described in more detail above with respect to the inner elongate member (204) of access device (200) in FIGS. 2 and 3A. In some of these variations, the handle (620) may comprise a connector. In these variations, the connector of the handle (620) may be configured to releasably connect to a corresponding connector on a locking member, the intermediate elongate member, the outer elongate member, or the like. In other variations, the tubular member (618) may comprise a connector, which may be configured to releasably connect to a corresponding connector on a locking member, the intermediate elongate member, the outer elongate member, or the like. Additionally, in some variations the handle (620) may be configured such that at least a portion of the handle (620) is sized such that it is prevented from entering the lumen (630) of the outer elongate member (602). In these variations, the handle (620) of the inner elongate member (606) may limit advancement of the inner elongate member (606) through the lumen (632) of the intermediate elongate member (604). In these variations, the inner elongate member (606) may be advanced into the lumen (632) (e.g., through the inlet of the lumen (632)) of the intermediate elongate member (604) until the handle (620) engages the inlet and prevents further advancement of the inner elongate member (606) relative to the intermediate elongate member (604).

The outer, intermediate, and inner elongate members (602, 604, 606) may comprise any combination of tubular members. In some variations, each of the outer, intermediate, and inner elongate members (602, 604, 606) may comprise needles. In another variation, the outer elongate member (602) may comprise a flexible sheath (e.g., a polymer sheath), and the intermediate and inner elongate members (604, 606) may each comprise a needle. In yet another variation, the outer elongate member (602) may comprise a flexible sheath, the intermediate elongate member (604) may comprise a hypotube (e.g., a stainless steel tube), and the inner elongate member (606) may comprise a needle. In another embodiment, the outer elongate member (602) may comprise a hypotube, and the intermediate and inner elongate members (604, 606) may each comprise a needle. In a variation, the outer and intermediate elongate members (602, 604) may each comprise a hypotube, and the inner elongate member (606) may comprise a needle. In still another variation, the outer elongate member (602) may comprise a hypotube, the intermediate elongate member (604) may comprise a flexible sheath, and the inner elongate member (606) may comprise a needle. It should be appreciated that still other combinations of elongate members may be utilized.

The outer, intermediate, and inner elongate members (602, 604, 606) may have any suitable dimensions. For example, FIG. 7B depicts a cross-sectional view of the tubular members of the access device (600) with the inner elongate member (606) positioned within the lumen (632) of the intermediate elongate member (604), and the intermediate elongate member (604) positioned within the lumen (630) of the outer elongate member (602). As shown there, the tubular member (610) of the outer elongate member (602) may have an outer diameter (706) and an inner diameter (708) (i.e., the diameter of lumen (630)). The tubular member (614) of the intermediate elongate member (604) may have an outer diameter (710) and an inner diameter (712) (i.e., the diameter of the lumen (632)). The tubular member (618) of the inner elongate member (606) may have an outer diameter (714). In variations where the inner elongate member (606) comprises a lumen (633), the elongate member may have an inner diameter (716) (i.e., the diameter of the lumen (633)).

The outer elongate member (602) may have any suitable inner and outer diameters. In some variations, the inner diameter (708) may be at least about 0.038 inches (0.965 mm). In some variations, the inner diameter (708) may be about 0.038 inches (0.965 mm). In some variations, the outer diameter (706) may be at least about 0.05 inches (1.27 mm), and in some variations may be about 0.05 inches (1.27 mm). For example, in some variations, the outer elongate member (602) may comprise a thin-wall, 18-gauge tubular member (e.g., an 18-gauge tube or an 18-gauge needle) having an inner diameter of about 0.038 inches (0.965 mm) and an outer diameter of about 0.05 inches (1.27 mm).

Similarly, the intermediate elongate member (604) may have any suitable inner and outer diameters. In some variations, the inner diameter (712) may be at least about 0.0255 inches (0.648 mm). In some variations, the inner diameter (712) may be about 0.0255 inches (0.648 mm). In some variations, the outer diameter (710) may be at least about 0.0355 inches (0.902 mm), and in some variations, may be about 0.0355 inches (0.902 mm). For example, in some variations the intermediate elongate member (604) may comprise a thin-wall, 20-gauge tubular member (e.g., a 20-gauge tube or a 20-gauge needle) having an inner diameter of about 0.0255 inches (0.648 mm) and an outer diameter of about 0.0355 inches (0.902 mm).

Additionally, the inner elongate member (606) may have any suitable inner and outer diameters. In some variations, the inner diameter (716) may be less than or equal to about 0.017 inches (0.432 mm). In some variations, the inner diameter (716) may be about 0.017 inches (0.432 mm). In some variations, the outer diameter (714) may be less than or equal to about 0.025 inches (0.635 mm), and in some variations, may be about 0.025 inches (0.635 mm). For example, in some variations, the inner elongate member (606) may comprise a thin-wall, 23-gauge tubular member (e.g., a 23-gauge tube or a 23-gauge needle) having an inner diameter of about 0.017 inches (0.432 mm) and an outer diameter of about 0.025 inches (0.635 mm).

Generally, the inner diameter (708) of the tubular member (610) of the outer elongate member (602) may be larger than the outer diameter (710) of the tubular member (614) of the intermediate elongate member (604), which may allow the tubular member (614) of the intermediate elongate member (604) to be slideably received in the lumen (630). Similarly, the inner diameter (712) of the tubular member (614) of the intermediate elongate member (604) may be larger than the outer diameter (714) of the tubular member (618) of the inner elongate member (606), which may allow the tubular member (618) of the inner elongate member (606) to be slideably received in the lumen (632) of the intermediate elongate member (606). For example, the tubular member (610) of the outer elongate member (602) may comprise a thin-wall, 18-gauge tubular member (e.g., an 18-gauge tube or an 18-gauge needle) having an outer diameter of about 0.05 inches (1.27 mm) and an inner diameter of about 0.038 inches (0.965 mm), the tubular member (614) of the intermediate elongate member (604) may comprise a thin-wall 20-gauge needle (e.g., a 20-gauge tube or a 20-gauge needle) having an outer diameter of about 0.0355 inches (0.902 mm) and an inner diameter of about 0.0255 inches (0.648 mm), and the tubular member (618) of the inner elongate member (606) may comprise a thin-wall, 23-gauge tubular member (e.g., a 23-gauge tube or a 23-gauge needle) having an outer diameter of about 0.025 inches (0.635 mm) and an inner diameter of about 0.017 inches (0.432 mm).

In another variation, the outer elongate member (602) may comprise a 6-French flexible introducer sheath having an outer diameter of about 0.079 inches (2.07 mm) and an inner diameter of about 0.062 inches (1.57 mm). In some of these variations, the intermediate elongate member (604) may comprise a combination of a thin-wall, 18-gauge tubular member (e.g., an 18-gauge tube or an 18-gauge needle) having an outer diameter of about 0.05 inches (1.27 mm) and an inner diameter of about 0.038 inches (0.965 mm) and a thin-wall, 20-gauge tubular member (e.g., a 20-gauge tube or a 20-gauge needle) having an outer diameter of about 0.0355 inches (0.902 mm) and an inner diameter of about 0.0255 inches (0.648 mm). In these variations, the 18-gauge tubular member and the 20-gauge needle may each be connected to the handle of the intermediate elongate member (604). In some of these variations, the inner elongate member (606) may comprise a thin-wall 23-gauge tubular member (e.g., a 23-gauge tube or a 23-gauge needle) having an outer diameter of about 0.025 inches (0.635 mm) and an inner diameter of about 0.017 inches (0.432 mm).

In another variation, the outer elongate member (602) may comprise a 5 French flexible introducer sheath having an outer diameter of about 0.066 inches (1.67 mm) and an inner diameter of about 0.042 inches (1.067 mm). In some of these variations, the intermediate elongate member (604) may comprise a thin-wall, 20-gauge tubular member (e.g., a 20-gauge tube or a 20-gauge needle) having an outer diameter of about 0.0355 inches (0.902 mm) and an inner diameter of about 0.0255 inches (0.648 mm). In these variations, the 20-gauge tubular member may be connected to the handle of the intermediate elongate member (604). In some of these variations, the inner elongate member (606) may comprise a thin-wall 23-gauge needle (e.g., a 23-gauge tube or a 23-gauge needle) having an outer diameter of about 0.025 inches (0.635 mm) and an inner diameter of about 0.017 inches (0.432 mm).

In some instances, it may be desirable to minimize the space between adjacent elongate members. The presence of the intermediate elongate member (604) may allow for a smaller inner elongate member (606) (which may reduce the likelihood of damaging the heart while puncturing the pericardium) and a larger outer elongate member (602) (which may allow for placement of a larger guide wire through the outer elongate member (602), as will be discussed in more detail below), but may reduce the risk that tissue is caught between the elongate members during advancement of the access device (600). To help reduce the likelihood that tissue is caught between the outer and intermediate elongate members, it may be desirable to reduce the space between the inner diameter (708) of the tubular member (610) of the outer elongate member (602) and the outer diameter (710) of the tubular member (614) of the intermediate elongate member (604). Similarly, it may be desirable to minimize the space between the inner diameter (712) of the tubular member (614) of the intermediate elongate member (604) and the outer diameter (714) of the tubular member (618) of the inner elongate member (606).

Accordingly, in some variations, the inner diameter (708) of the tubular member (610) of the outer elongate member (602) may be less than or equal to about 0.006 inches (0.152 mm) larger than the outer diameter (710) of the tubular member (614) of the intermediate elongate member (604), may be between about 0.003 inches (0.076 mm) and about 0.006 inches (0.152 mm) larger than the outer diameter (710) of the tubular member (614) of the intermediate elongate member (604), or may be less than or equal to about 0.001 inches (0.025 mm) larger than the outer diameter (710) of the tubular member (614) of the intermediate elongate member (604). In any of the above variations, the inner diameter (712) of the tubular member (614) of the intermediate elongate member (604) may be less than or equal to about 0.006 inches (0.152 mm) larger than the outer diameter (714) of the tubular member (618) of the inner elongate member (606), may be between about 0.003 inches (0.076 mm) and about 0.006 inches (0.152 mm) larger than the outer diameter (714) of the tubular member (618) of the inner elongate member (606), or may be less than or equal to about 0.001 inches (0.025 mm) larger than the outer diameter (714) of the tubular member (618) of the inner elongate member (606). In these variations, the inner elongate member (606) may still be slideable within the intermediate elongate member (604), and the intermediate elongate member (604) may be slideable within the outer elongate member (602).

The design of the distal tips of the elongate members may facilitate the device's transition through the pericardium. When the distal tip of the inner elongate member (606) punctures tissue, it may create an opening in the tissue large enough to accommodate a device of the same diameter as the inner elongate member (606). The inner elongate member (606) may, however, have a diameter that is smaller than other devices that may be used to complete a procedure, like, for example, a guide wire. After puncturing the tissue with the inner elongate member (606), the intermediate and outer elongate members (604,602) may be advanced to enlarge the opening in the tissue. Maintaining small radial distances between the three elongate members (602, 604, 606) when they are arranged concentrically may also help to ease the transition through tissue.

As mentioned above, and as shown in FIG. 7A, the tubular member (618) of the inner elongate member (606) may be longer than the intermediate elongate member (604), such that when the inner elongate member (606) and the intermediate elongate member (604) are arranged concentrically, the distal tip of the inner elongate member (606) may be advanced distally beyond the distal tip of the intermediate elongate member (604). Additionally, the tubular member (618) of the inner elongate member (606) may be longer than the outer elongate member (602), such that when the inner elongate member (606), the intermediate elongate member (604), and outer elongate member (602) are arranged concentrically, the distal tip of the inner elongate member (606) may be advanced distally beyond the distal tip of the outer elongate member (602). For example, in some variations, the length of the tubular member (618) of the inner elongate member (606) may be at least about 1 inch (2.54 cm) longer than the lengths of the intermediate elongate member (604) and the outer elongate member (602). In some of these variations, the length of the tubular member (618) of the inner elongate member (606) may be at least about 2 inches (5.08 cm) longer than the lengths of the intermediate elongate member (604) and the outer elongate member (602). Additionally, in some variations, the length of the tubular member (614) of the intermediate elongate member (604) may be approximately equal to the length of the outer elongate member (602), such that when the tubular member (614) of the intermediate elongate member (604) is advanced into the lumen (630) of the outer elongate member (602), the distal tip of the intermediate elongate member (604) may be flush with the distal tip of the outer elongate member (602). In other variations, the length of the tubular member (614) of the intermediate elongate member (604) may be longer than the length of the outer elongate member (602), such that when the tubular member (614) of the intermediate elongate member (604) is advanced into the lumen (630) of the outer elongate member (602), the distal tip of the intermediate elongate member (604) may be positioned distally of the distal tip of the outer elongate member (602).

When the access devices described here are used to access the pericardial space using a sub-xiphoid approach, the inner, intermediate, and outer elongate members may be sized such that the tubular member of each of the inner, intermediate, and outer elongate members may reach the pericardium from a sub-xiphoid access point. In some variations, the tubular member (610) of the outer elongate member (602) may be at least about 5.5 inches (13.97 cm) in length. In some variations, the outer elongate member (602) may be at least about 6 inches (15.24 cm) in length. In some variations, the length of the tubular member (610) of the outer elongate member (602) may be at least about 5.9 inches (14.99 cm). In some of these variations, the outer elongate member (602) may be at least about 6.5 inches (16.51 cm) in length. Additionally or alternatively, the tubular member (614) of the intermediate elongate member (604) may be at least about 7 inches (17.78 cm) in length, and in some variations may be about 7.3 inches (18.54 cm) in length. In some of these variations, the intermediate elongate member (604) may be at least about 8 inches (20.32 cm) in length. Additionally or alternatively, the tubular member (618) of the inner elongate member (606) may be at least about 9.5 inches (24.13 cm) in length. In some variations, the inner elongate member (606) may be at least about 10 inches (25.4 cm) in length. In some variations, the tubular member (618) of the inner elongate member (606) may be about 10 inches (25.4 cm) in length. In some of these variations, the inner elongate member (606) may be at least about 11.5 inches (29.2 cm) in length. The varied lengths of the inner, intermediate, and outer elongate members (602, 604, 606) may allow a user to puncture the pericardium with the inner elongate member (606) by advancing the distal tip of the inner elongate member (606) past the distal tips of the outer and intermediate elongate members (602, 604).

In some variations, it may be desirable to limit the distance that the tip of the inner elongate member (606) extends beyond the distal tip of intermediate elongate member (604) when the access device is in the delivery configuration. Similarly, it may be desirable to limit the distance that the distal tip of intermediate elongate member (604) extends beyond the distal tip of the outer elongate member (606). Limiting the extension of the inner elongate member (606) relative to the intermediate elongate member (604) may reduce the likelihood that the inner elongate member (606) is damaged if the inner elongate member (606) catches on tissue during advancement, while limiting the extension of the intermediate elongate member (604) relative to the outer elongate member (602) may reduce the likelihood that the inner elongate member (606) and/or intermediate elongate member (604) are damaged if either of these members catch on tissue during advancement. For example, as mentioned above, in some variations the distal tips of each of the outer, intermediate, and inner elongate members (602, 604, 606) may be flush when positioned in the delivery configuration. A locking member (608) and/or one or more connectors may maintain the relative positioning of the outer, intermediate, and inner elongate members (602, 604, 606).

In other variations, it may be desirable for the distal tip of the inner elongate member (606) to extend slightly beyond the tip of the intermediate elongate member (604). In these variations, the smaller outer diameter of the tubular member (618) of the inner elongate member (606) may encounter less resistance when advancing through tissue relative to the intermediate elongate member (604), which may facilitate advancement of the access device (600). Additionally, by limiting the extension of the distal tip of the inner elongate member (606), the intermediate elongate member (604) may reinforce the distal tip of the inner elongate member (606) (e.g., to help minimize bending or kinking of the inner elongate member (606) as discussed above) and may help facilitate advancement of the access device (600). In some embodiments, the distal tip of the inner elongate member (606) may extend beyond the distal tip of the intermediate elongate member (604) by a distance less than about 0.4 inches (10.16 mm) when the access device is in the delivery configuration. In some embodiments, the distal tip of the inner elongate member (606) may extend beyond the distal tip of the intermediate elongate member (604) by a distance less than or equal to about 0.3 inches (7.62 mm) when the access device is in the delivery configuration. In some of these variations, the distal tip of the inner elongate member (606) may extend beyond the distal tip of the intermediate elongate member (604) by a distance less than about 0.2 inches (5.08 mm). In some variations, the distal tip of the inner elongate member (606) may extend beyond the distal tip of the intermediate elongate member (604) by a distance about 0.1 inches (2.54 mm) to about 0.2 inches (5.08 mm).

In some variations where the distal tip of inner elongate member (606) extends beyond the distal tip of the intermediate elongate member (604) in the delivery configuration, the distal tip of the intermediate elongate member (604) may be flush with the distal tip of the outer elongate member (602). In other variations, the distal tip of the intermediate elongate member (604) may extend beyond the distal tip of the outer elongate member (602) when the access device (600) is in a delivery configuration. In some embodiments, the distal tip of the intermediate elongate member (604) may extend beyond the distal tip of the outer elongate member (602) by a distance less than about 0.3 inches (7.62 mm). In some of these variations, the distal tip of the intermediate elongate member (604) may extend beyond the distal tip of the outer elongate member (602) by a distance less than about 0.2 inches (5.08 mm). In some variations, the distal tip of the intermediate elongate member (604) may extend beyond the distal tip of the outer elongate member (602) by a distance of about 0.05 inches (1.27 mm) to about 0.2 inches (5.08 mm). As mentioned above, a locking member (608) and/or one or more connectors may be configured to maintain this relative positioning when the access device (600) is in the delivery configuration. In some embodiments, the distance between the distal tips of the intermediate and inner elongate members (604, 606) may be the same as the distance between the distal tips of the outer and intermediate elongate members (602, 604). In other embodiments, the distance between the distal tips of the intermediate and inner elongate members (604, 606) may be greater than the distance between the distal tips of the outer and intermediate elongate members (602, 604), or vice versa. It should also be appreciated that in some variations, the distal tip of the inner elongate member (606) may be proximal to the distal tips of one or both of the outer elongate member (602) and intermediate elongate member (604), and in some variations, the distal tip of the intermediate elongate member (604) may be proximal to the distal tip of the outer elongate member (602).

The distal tips of the outer, intermediate, and inner elongate members (602, 604, 606) may be configured to facilitate the formation of and/or enlargement of a tissue opening. For example, in some variations, the tips of each of the outer, intermediate, and inner elongate members (602, 604, 606) may have a bevel or edge configured to pierce tissue. In some of these variations, each of the outer, intermediate, and inner elongate members (602, 604, 606) may have a beveled tip. In these variations, the angles of the bevels of the tips of the outer, intermediate, and inner elongate members (602, 604, 606) may be the same or may be different. In other variations, the distal tips of one or more of the outer, intermediate, and inner elongate members (602, 604, 606) may have a circumferential or semi-circular cutting edge, such as discussed above.

Figure 8A:
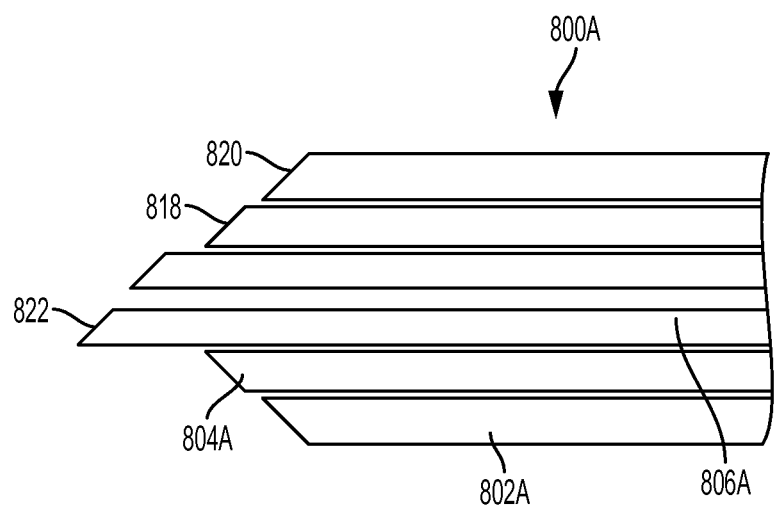
FIGS. 8A-8D depict longitudinal cross-sectional views of distal ends of variations of the access devices described here.
Figure 8B:
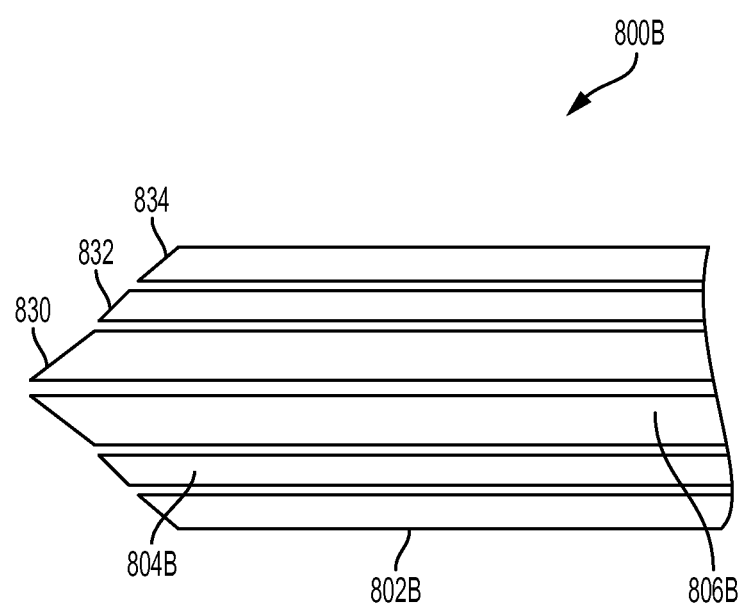

For example, FIG. 8A illustrates a variation of an access device (800A) in which the outer elongate member (802A) has a circumferential or semi-circular cutting edge (820), the intermediate elongate member (804A) has a circumferential or semi-circular cutting edge (818), and the inner elongate member (806A) has a beveled edge (822). In some of these variations, the bevel angle of the beveled edge (822) may be the same as the bevel angle of the cutting edges (818, 820), which may provide an even thickness transition between the elongate members. In other variations, some of these bevel angles may be different from each other. FIG. 8B shows another variation of an access device (800B) in which each of the inner, intermediate, and elongate members (806B, 804B, 802B) comprise a circumferential or semi-circular cutting edge (labeled as 830, 832, and 834, respectively). In some variations, the bevel angles of each of the circumferential or semi-circular cutting edges (830, 832, 834) may be the same. For example, the circumferential or semi-circular cutting edges (830, 832, 834) may be machined together while the outer, intermediate, and inner elongate members (802B, 804B, 806B) are concentrically arranged to create a smooth transition between the outer, intermediate, and inner elongate members (802B, 804B, 806B).

Figure 8C:
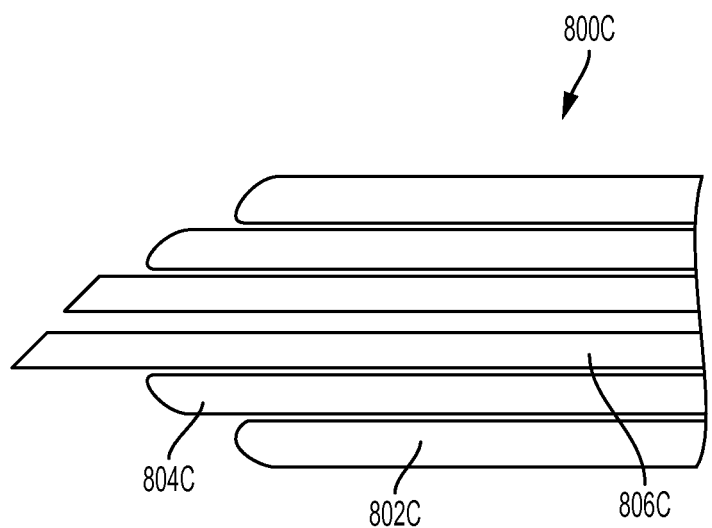
Figure 8D:
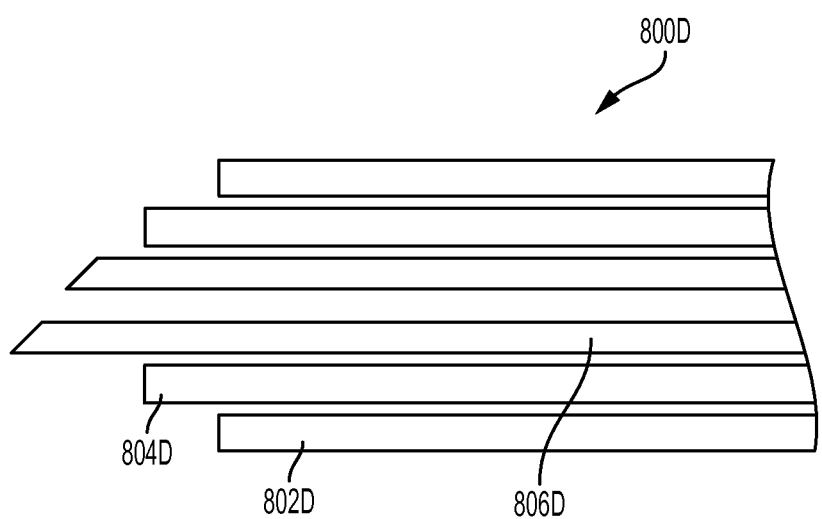

In other variations, distal tips of the intermediate and/or outer elongate members may be blunt. For example, FIG. 8C depicts a variation of an access device (800C) in which the outer and intermediate elongate members (802C, 804C) each have distal tips that are rounded. The rounded portions of each of distal tips of the outer and intermediate elongate member (802C, 804C) may comprise any suitable radius of curvature (the tips of the intermediate and outer elongate members may have the same radius of curvature or different radii of curvature) and may facilitate expansion of a tissue opening when the outer and intermediate elongate members (802C, 804C) are advanced along the inner elongate member (806C). FIG. 8D illustrates another embodiment of an access device (800D) in which the tubular members of each of the outer and intermediate elongate members (802D, 804D) have flat distal tips (e.g., distal surfaces substantially perpendicular to the longitudinal axis of the tubular members). While the inner elongate member (806C, 806D) is shown in FIGS. 8C and 8D as having a beveled distal tip, it should be appreciated that, in these variations, the inner elongate member (806C, 806D) may be configured with any suitable tissue-piercing tip (e.g., a circumferential or semi-circular cutting edge or the like).

Turning back to FIG. 7A, as mentioned above, the access device (600) may comprise a locking member (608) configured to releasably constrain the relative movement of two or more of the elongate members. In some embodiments, the locking member (608) may temporarily constrain the position of the inner elongate member (606) in relation to the position of the intermediate elongate member (604). In other embodiments, the locking member (608) may temporarily constrain the position of the intermediate elongate member (604) in relation to the outer elongate member (602). In some embodiments, the locking member (608) may temporarily fix the position of the inner elongate member (606) in relation to the position of the intermediate elongate member (604) and/or the outer elongate member (602). In other embodiments, the locking member (608) may be configured to limit the relative movement between the inner elongate member (606) and the intermediate elongate member (604) and/or the outer elongate member (602). For example, in some variations, the locking member (608) may be positioned to limit the amount that the inner elongate member (606) may be advanced into the lumen (632) of the intermediate elongate member (604).

While shown in FIG. 7A as having one locking member (608), it should be appreciated that, in some instances, the access device may comprise two locking members. For example, in some variations, the access device (600) may comprise a first locking member configured to constrain relative movement between the intermediate elongate member (604) and the inner elongate member (606), and a second locking member configured to constrain relative movement between the intermediate elongate member (604) and the outer elongate member (602). In other variations, the access device may comprise a first locking member configured to constrain relative movement between the outer elongate member (602) and the inner elongate member (606) and a second locking member configured to constrain relative movement between the outer elongate member (602) and the intermediate elongate member (604).

Any of the locking members described above with respect to FIGS. 2, 3A, and 5A-5E may be used with the access devices described above with respect to FIGS. 6 and 7A. For example, in the variation of the access device (600) shown in FIGS. 6A, 6B, and 7A, the access device (600) may comprise a locking member (608) configured to releasably connect the inner elongate member (606) relative to the intermediate elongate member (604). As shown there, the locking member (608) may comprise a body (622) and a lumen (634) extending through the body (622). The body (622) may have any suitable cross-sectional shape, for example, circular, square, oval, triangular, or hexagonal. In some variations, the locking member (608) may comprise a slit or channel (e.g., channel (628) depicted in FIG. 6) extending from an external surface of the body (622) to the lumen (634), which may allow for radial connection or removal of the locking member (608), as discussed in more detail above. The locking member (608) may be placed around the inner elongate member (606) (e.g., with the tubular member (618) of the inner elongate member (606) extending through the lumen (634) of the locking member (608)) to position the locking member (608) between the handle (620) of the inner elongate member (606) and the handle (616) of the intermediate elongate member (604).

This may allow the locking member (608) to act as a spacer, which may limit the ability of the tubular member (618) of the inner elongate member (606) to be advanced into the lumen (632) of the intermediate elongate member (604), such as discussed in more detail above.

The locking member (608) may be configured to releasably fix to one or both of the inner elongate member (606) and the intermediate elongate member (604). In some variations, the access device (600) may comprise the locking member (560) described above with respect to FIGS. 5D and 5E. In some variations, the lumen (634) of the locking member (608) may form a frictional hold with the tubular member (618) of the inner elongate member (606) when the tubular member (618) is positioned in the lumen (634), such as described in more detail above. Additionally or alternatively, the locking member (608) may comprise one or more connectors. For example, in the variation shown in FIG. 7A, the locking member (608) may comprise a proximal connector (624) and a distal connector (626). The proximal connector (624) may be configured to releasably connect to the inner elongate member (606) (e.g., may releasably connect to a counterpart connector (640) on the handle (620) of the inner elongate member (606)). Similarly, the distal connector (626) may be configured to releasably connect to the intermediate elongate member (604) (e.g., to a counterpart proximal connector (642) of the handle (616) of the intermediate elongate member (604)). Each of the proximal connector (624) and distal connector (626) (as well as the counterpart connectors (640) and (642) of the inner and intermediate elongate members (606, 604) in variations that include these connectors), may be any suitable connectors as discussed above, such as, for example, luer lock connectors, luer slip/slip-tip connectors, snap-fit connectors, hinged-clip connectors, or the like.

In variations where the locking member (608) connects to counterpart connectors (640, 642) on the inner elongate member (606) and intermediate elongate member (642), respectively, the connectors (640, 642) may releasably connect to each other to fix the inner elongate member (606) relative to the intermediate elongate member (604) after the locking member is removed, such as discussed in more detail above. For example, in some variations, the connector (640) of the inner elongate member (606) may comprise a male luer lock connector and the connector (642) of the intermediate elongate member (604) may comprise a female luer lock, or vice versa, such that the inner elongate member (606) may connect to the intermediate elongate member (604). In these variations, the proximal connector (624) of the locking member (608) may comprise a female luer lock connector and the distal connector (626) of the locking member (608) may comprise a male luer lock, or vice versa, to allow connection of the locking member (608) to the inner and intermediate elongate members (606, 604).

While shown in FIGS. 6 and 7A as having both proximal and distal connectors, it should be appreciated that, in some instances, the locking member (608) may include only one connector and in other instances may not comprise any connector. For example, in some variations, the locking member (608) may comprise only a proximal connector (624) configured to connect the locking member (608) to a portion of the inner elongate member (606). For example, the locking member (608) may releasably connect to a counterpart connector (640) on the handle (620) of the inner elongate member (606). In these variations, the locking member (608) may act as a stop to limit the movement of the inner elongate member (606) distally relative to the intermediate elongate member (604). For example, the inner elongate member (606) and the locking member (608) may be advanced together until a distal portion of the locking member (608) engages a proximal portion of the intermediate elongate member (604) and prevents further distal movement of the inner elongate member (606). In these variations, the inner elongate member (606) and the locking member (608) may still be freely withdrawn relative to the intermediate elongate member (604).

In other variations, the locking member (608) may comprise only a distal connector (626) configured to connect the locking member (608) to a portion of the intermediate elongate member (604). In these variations, the locking member (608) may act as a stop to limit the movement of the inner elongate member (606) distally relative to the intermediate elongate member (604) (e.g., the inner elongate member (606) may be advanced relative to the intermediate elongate member (604) and the locking member (608) until the handle (620) or another portion of the inner elongate member (606) engages a proximal portion of the locking member (608) and prevents further distal movement of the inner elongate member (606)). In some of these variations, the locking member (608) may comprise a lumen (634) configured to frictionally hold the inner elongate member (606), such that the positions of the inner elongate member (606) and intermediate elongate member (604) are temporarily fixed relative to each other. In other variations, the inner elongate member (606) may be freely withdrawn relative to the locking member (608) and the intermediate elongate member (604).

In some variations where the locking member (608) fixes the inner and intermediate elongate members or otherwise constrains relative movement therebetween, the intermediate and outer elongate members may be releasably fixed to each other. For example, in some variations the intermediate elongate member may comprise a connector configured to releasably connect to a connector of the outer elongate member. For example, in the variation shown in FIG. 7A, the handle (616) of the intermediate elongate member (604) may comprise a distal connector (644). In these variations, the distal connector (644) may releasably connect to a corresponding connector (646) on the handle (612) of the outer elongate member. In these variations, the connectors (644, 646) may directly connect the intermediate and outer elongate members (604, 602). In some variations, a locking member may be configured to connect the intermediate elongate member (604) to the outer elongate member (602), and may be configured in any manner as discussed above. It should be appreciated that all of the connectors employed may be compatible such that the locking members may be interchangeable and all three elongate members may be connectable. In some embodiments, depending on the type of connectors utilized, additional connectors may be added to any component to create compatibility.

Systems and Kits

Any of the access devices described above may be used as part of a system or a kit for accessing the pericardial space. Generally, such a system or kit may comprise an access device and at least one guide wire configured for advancement through the access device. A system or a kit comprising an access device having an inner and an outer elongate member, such as one of the variations of the access device (200) depicted in FIGS. 2 and 3A, may further comprise a first guide wire. In some instances, the kit may also comprise a polymer sheath or introducer and/or a second guide wire. In other variations, a system or a kit may comprise an access device with three elongate members, such as one of the variations of the access device (600)

described above with respect to FIGS. 6 and 7A, and may further comprise a first guide wire. In some of these variations, the system or kit may comprise a second guide wire. The guide wires may be used to facilitate access to and/or advancement of devices into the pericardial space, as discussed in more detail below.

As mentioned above, the systems and kits described here may comprise an access device having two elongate members. Specifically, the access device may comprise an inner elongate member and an outer elongate member, where a tubular member of the inner elongate member is slideably positioned in a lumen of the outer elongate member. In some variations, the access device may further comprise a locking member configured to fix or constrain the position of the inner elongate member relative to the outer elongate member. The inner elongate member, outer elongate member, and locking member may be configured in any suitable manner as described above with respect to FIGS. 2 and 3A.

Additionally, the system may comprise one or more guide wires. In some variations, the system may comprise a first guide wire configured to fit within the outer elongate member. In these systems, the first guide wire may be advanced through the outer elongate member when the inner elongate member has been removed from the lumen of the outer elongate member, as will be discussed in more detail below. In variations where the inner elongate member comprises a lumen extending through the inner elongate member, the system may further comprise a second guide wire. In these variations, the second guide wire may be sized to fit within the lumen of the inner elongate member (e.g., the diameter of the second guide wire may be less than the inner diameter of the tubular member of the inner elongate member), while the first guide wire may be larger than the tubular member of the of the inner elongate member (e.g., the diameter of the first guide wire may be larger than the inner diameter of the lumen of the inner elongate member and less than the inner diameter of the lumen of the outer elongate member).

In one variation of the systems and kits described here, the access device may comprise an outer elongate member having an 18-gauge tubular member having an inner diameter of about 0.033 inches (0.838 mm), and the inner elongate member may comprise a 21-gauge tubular member (such as a needle) having an inner diameter of about 0.0195 inches (0.495 mm) and an outer diameter of about 0.032 inches (0.813 mm). In some variations, the system may comprise a guide wire having a diameter less than or equal to about 0.033 inches (0.838 mm). In other variations, the system may comprise a first guide wire having a diameter between about 0.02 inches (0.508 mm) and about 0.03 inches (0.762 mm) and a second guide wire having a diameter less than about 0.195 inches (0.495 mm) (e.g., between about 0.014 inches (0.356 mm) and about 0.018 inches (0.457 mm)). In some variations, the system may comprise a first guide wire having a diameter less than or equal to about 0.035 inches (0.889 mm) and a second guide wire having a diameter smaller than the diameter of the first guide wire, which may be less than or equal to about 0.018 inches (0.457 mm).

In some instances, the systems and kits described here may additionally comprise a polymer sheath or an introducer that may be used with the access devices described here. The introducer or polymer sheath may be any suitable size, for example, it may be a 4-French, a 5-French, or a 6-French sheath. The polymer sheath or introducer may comprise a dilator portion, but need not. The dilator portion may be a portion of the polymer sheath or introducer configured to enlarge and/or expand an opening in tissue. For example, in some embodiments, the dilator portion may comprise ramped or angled surfaces. In some variations, the systems and kits here may comprise an access device, an introducer, and at least one guide wire. For example, the systems or kits may comprise an access device comprising an outer elongate member with an 18-gauge tubular member and an inner elongate member with a 21-gauge tubular member, an introducer or polymer sheath, and at least a first guide wire having a diameter of about 0.018 inches (0.457 mm). In some variations, the systems or kits may also comprise a second guide wire having a diameter of about 0.035 inches (0.889 mm).

The systems above may be packaged as a kit. In some variations, the access device may be packaged in a delivery configuration (which may be one of the delivery configurations described above), with the locking member connecting and holding the inner elongate member and the outer elongate member in the delivery configuration. For example, when in the delivery configuration, the distal tip of the inner elongate member may slightly extend from the distal tip of the outer elongate member, such as discussed in more detail above. In variations where the system comprises an introducer or polymer sheath and one or more guide wires, the access device may be packaged together with or separately from the introducer and guide wires. In variations where the kit comprises a guide wire sized to fit within a lumen of the inner elongate member, the system may be packaged with the guide wire positioned at least partially within the lumen of the inner elongate member.

In other variations, the system may comprise an access device having three elongate members. Specifically, the access device may comprise an inner elongate member, an intermediate elongate member, and an outer elongate member, where a tubular member of the inner elongate member is positioned within a lumen of the intermediate elongate member and a tubular member of the intermediate elongate member is positioned within a lumen of the outer tubular member. In some variations, the access device may comprise a first locking member fixing or constraining the inner elongate member relative to the intermediate elongate member. In some of these variations, the intermediate elongate member and the outer elongate member may be directly connected. In other variations, the access device may comprise a second locking member fixing or constraining the outer elongate member relative to the inner elongate member. The inner elongate member, intermediate elongate member, outer elongate member, and locking member may be configured in any suitable manner as described above with respect to FIGS. 6 and 7A.

Additionally, the system may comprise one or more guide wires. In some variations, the system may comprise a first guide wire configured to fit within the outer elongate member. In these systems, the first guide wire may be advanced through the outer elongate member when the inner elongate member and the intermediate elongate member have been removed from the lumen of the outer elongate member, as will be discussed in more detail below. In variations where the inner elongate member comprises a lumen extending through the inner elongate member, the system may further comprise a second guide wire. In these variations, the second guide wire may be sized to fit within the lumen of the inner elongate member (e.g., the diameter of the second guide wire may be less than the inner diameter of the tubular member of the inner elongate member), while the first guide wire may be larger than the lumen of the of the inner elongate member (e.g., the diameter of the first guide wire may be larger than the inner diameter of the tubular member of the inner elongate member and less than the inner diameter of the tubular member of the outer elongate member). In some of these variations, the first guide wire may be larger than the lumen of the intermediate elongate member, while in other variations the first guide wire may be smaller than the lumen of the intermediate elongate member.

In one variation of the systems and kits described here, the access device may comprise an outer elongate member having a thin-wall 18-gauge tubular member having an inner diameter of about 0.038 inches (0.965 mm), an intermediate elongate member having a thin-wall 20-gauge tubular member having an inner diameter of about 0.0255 inches (0.648 mm) and an outer diameter of about 0.0355 inches (0.902 mm), and an inner elongate member having a thin-wall 23-gauge tubular member (such as a needle) having an inner diameter of about 0.017 inches (0.438 mm) and an outer diameter of about 0.025 inches (0.635 mm). In some variations, the system may comprise a guide wire having a diameter less than or equal to about 0.038 inches (0.965 mm) (e.g., between about 0.02 inches (0.508 mm) and about 0.03 inches (0.762 mm)). In some variations, the system may comprise a guide wire having a diameter of about 0.035 inches (0.889 mm). In some of these variations, the guide wire may be configured to fit within the lumen of the outer elongate member but not the lumen of the intermediate elongate member (e.g., the guide wire may have a diameter between about 0.026 inches (0.660 mm) and about 0.037 inches (0.940 mm)). In other variations, the system may comprise a first guide wire having a diameter between about 0.02 inches (0.508 mm) and about 0.037 inches (0.940 mm) and a second guide wire having a diameter less than about 0.0125 inches (0.318 mm). In some variations, the system may comprise a second guide wire having a diameter of about 0.014 inches (0.355 mm).

The systems above may be packaged as a kit. In some variations, the access device may be packaged in a delivery configuration (which may be one of the delivery configurations described above). For example, the access device may be packaged with a first locking member connecting the inner elongate member to the intermediate elongate member, and with the intermediate elongate member connected to the outer elongate member to hold the access device in a delivery configuration. In other variations, the access device may be packaged with a first locking member connecting the inner elongate member to the intermediate elongate member and a second locking member connecting the intermediate elongate member to the outer elongate member to hold the access device in a delivery configuration. For example, when in the delivery configuration, the distal tip of the inner elongate member may extend slightly beyond the distal tip of the intermediate elongate member, which in turn may extend slightly beyond the distal tip of the outer elongate member, such as discussed in more detail above. In variations where the system comprises one or more guide wires, the access device may be packaged together with or separately from the guide wires. In variations where the kit comprises a guide wire sized to fit within a lumen of the inner elongate member, the system may be packaged with the guide wire positioned at least partially within the lumen of the inner elongate member.

Methods

The access devices and systems described above may be used to pierce the pericardium and gain access to the pericardial space, or to pierce any fluid-filled membrane or sac to access the structures therein, e.g., dura mater, peritoneum, amniotic sac, and the like. Generally, the methods described here may comprise advancing an access device to the pericardium and advancing an inner elongate member relative to an outer elongate member to pierce the pericardium. In some variations, the method may comprise disengaging a locking member prior to advancing the inner elongate member. The access devices may be used in combination with an introducer or polymer sheath and/or one or more guide wires. Generally, methods described here utilizing one or more guide wires comprise advancing an access device to the pericardium, advancing an inner elongate member relative to one or more outer and/or intermediate elongate members to pierce the pericardium, advancing a first guide wire through the inner elongate member into the pericardial space, removing one or more of the elongate members from the pericardial space and, if desired, replacing the first guide wire with a second guide wire. Once a guide wire is placed in the pericardial space, one or more additional devices may be advanced over the guide wire to perform one or more treatment operations in the pericardial space.

Figure 9A:
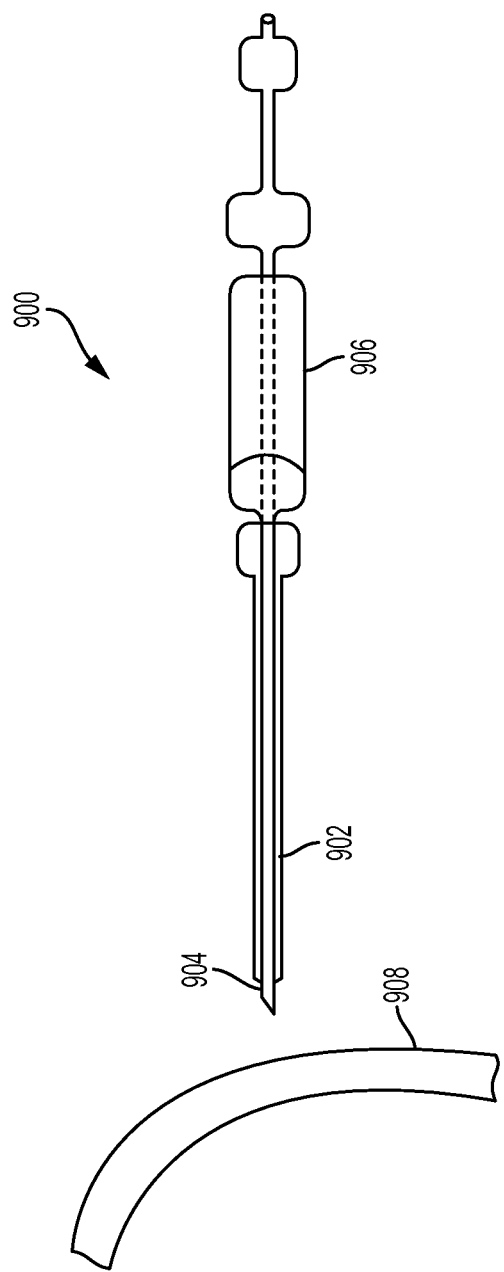

FIGS. 9A-9E depict illustrious methods by which an access device (900) having a first outer elongate member (902) and a second inner elongate member (904) positioned at least partially within the lumen of the outer elongate member (902) may be used to access the pericardial space of a patient. Generally, the access device (900) may be advanced through an entry site in the body (which may be a sub-xiphoid access site), and to a position in which a distal end of the access device (900) is at the external surface of the pericardium (908), as shown in FIG. 9A. The access device (900) may be visualized while it is advanced, for example, using fluoroscopy, ultrasound, or the like, so that the positioning of the access device (900) relative to the pericardium, heart, and/or other cardiac structures may be discerned.

The access device (900) may be placed in a delivery configuration when the access device (900) is positioned as shown in FIG. 9A. The delivery configuration may be any of the delivery configurations described above with respect to the variations of the access device (200) of FIGS. 2 and 3A. For example, in some variations, the distal tip of the inner elongate member (904) may extend slightly beyond the outer elongate member (906) when in the delivery configuration, such as described in more detail above. A locking member (906) (which may be any of the locking members described above) may hold the access device (900) in the delivery configuration or may facilitate placement of the access device (900) in the delivery configuration.

In some variations, the access device (900) may be advanced into the body and positioned at the pericardium (908) while in the delivery configuration. In these variations, the outer elongate member (902) and the inner elongate member (904) may be advanced and manipulated together. In some instances, a locking member (906) may hold the outer elongate member (902) relative to the inner elongate member (904) (e.g., in the delivery configuration) during advancement of the access device. The locking member (906) may constrain movement of the inner elongate member (904) during advancement of the access device (e.g., the locking member (906) may prevent advancement of the inner elongate member (904) past the delivery configuration). In other instances, the inner and outer elongate members may be advanced sequentially. For example, the outer elongate member (902) may be advanced into the body to position a distal tip of the outer elongate member (904) at an external surface of the pericardium. After the outer elongate member (902) has been positioned, a portion of the inner elongate member (904) may be advanced through a lumen of the outer elongate member (902) to place the access device (900) in the delivery configuration. In some of these variations, the locking member (906) may help place and/or hold the access device in the delivery configuration (e.g., by preventing the inner elongate member (904) from being advanced past the delivery configuration toward a piercing configuration). For example, the locking member (906) may be connected to the outer elongate member (904) when the inner elongate member (902) is advanced through the outer elongate member (904). In other instances, the locking member (906) may be connected to the inner elongate member (902) when the inner elongate member (902) is advanced through the outer elongate member (904). In still other instances, the locking member (906) may be positioned around a tubular member of the inner elongate member and positioned between the handles of each of the inner and outer elongate members during advancement of the inner elongate member.

Figure 9B:
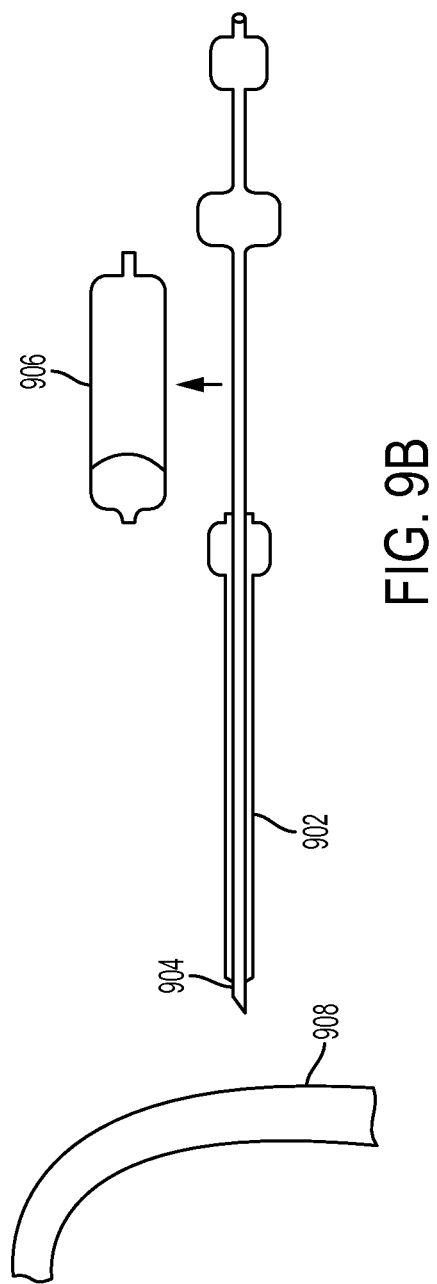

After the access device (900) has been positioned as depicted in FIG. 9A, the access device (900) may be moved from a delivery configuration to a piercing configuration. In variations where a locking member (906) is engaged or is otherwise connected to one or both of the inner and outer elongate members, the locking member (906) may be disengaged from the inner and outer elongate members, such as shown in FIG. 9B. In some variations, the locking member (906) may be radially disengaged from the access device (900), such as discussed in more detail above. With the locking member (906) disengaged, the inner elongate member (904) may be advanced relative to the outer elongate member (902) to move the access device (900) to a piercing configuration, as shown in FIG. 9C. As the inner elongate member (902) is advanced relative to the outer elongate member (902), a distal tip of the inner elongate member (902) (which may be configured to pierce tissue, for example, it may be sharpened) may puncture the pericardium (908) to enter the pericardial space. In some variations, the inner elongate member (904) may be connected to the outer elongate member (902) when the access device is positioned in the piercing configuration (e.g., a connector on a handle of the inner elongate member (904) may releasably connect to a handle of the outer elongate member (902)).

Figure 9D:
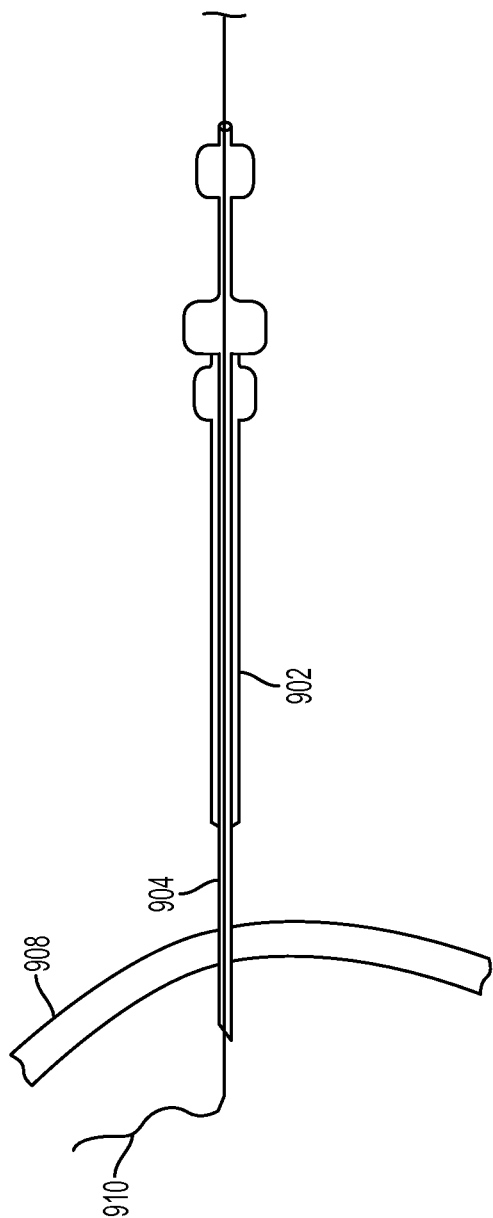

In some variations, a first guide wire (910) may be advanced through a lumen of the inner elongate member (904) to position a distal portion of the first guide wire (910) in the pericardial space, as shown in FIG. 9D. In some instances, the first guide wire (910) may be used to confirm that the inner elongate member has entered the pericardial space. As the first guide wire (910) is advanced into the pericardial space, it may wrap around the heart or otherwise be constrained within the pericardium, which may be confirmed using indirect visualization (e.g., via fluoroscopy). In some variations, placement of the first guide wire may prevent or reduce the risk of heart lacerations or puncture as portions of the access device are advanced and manipulated. Additionally or alternatively, a fluid or gas (e.g., carbon dioxide) may be introduced into the pericardial space to lift the pericardium away from the heart. In some variations, the access device may be removed from the body, leaving the first guide wire (910) in place in the pericardial space, and one or more devices may be advanced over the first guide wire (910).

Additionally or alternatively, one or more dilators may be used to replace the first guide wire (910) with a larger guide wire, over which one or more devices may be advanced. For example, an introducer or polymer sheath may be advanced over the first guide wire (910) (i.e., the guide wire (910) may be at least partially slideably disposed within a lumen of the introducer or polymer sheath) and into the pericardial space after the access device has been removed from the body. The first guide wire (910) may then be withdrawn from the body through the introducer, and at least a distal portion of a second, larger guide wire may be advanced through the introducer or polymer sheath into the pericardial space. In some instances, it may be beneficial to remove the first guide wire and replace it with a larger, second guide wire so that larger devices may access the pericardial space.

Figure 9E:
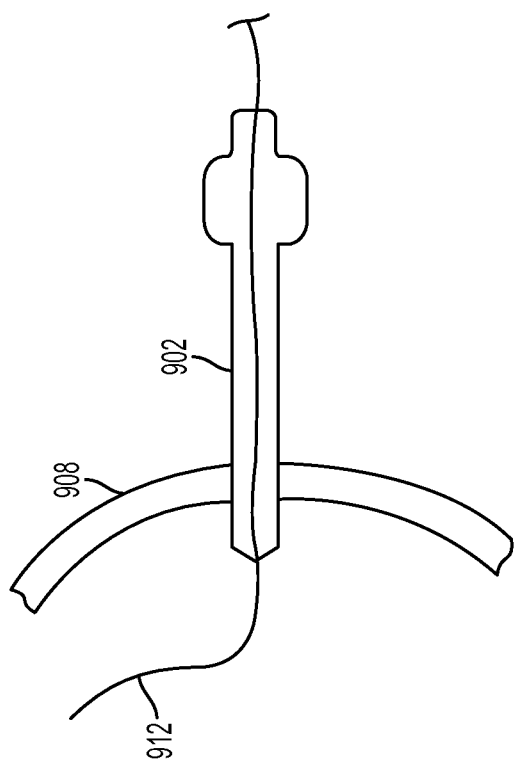

In some variations, a guide wire may be advanced through a lumen of the outer elongate member (902) to position a distal portion of it in the pericardial space. For example, once the inner elongate member (904) has pierced the pericardium (908), the outer elongate member (902) may be advanced over the inner elongate member (904) to position a distal tip of the outer elongate member (902) in the pericardial space. When the outer elongate member (902) is positioned in the pericardial space, the inner elongate member (904) may be removed from the outer elongate member (902), and a guide wire (912) may be advanced through a lumen of the outer elongate member (902), such as shown in FIG. 9E. In variations where a first guide wire (910) is advanced through the inner elongate member (904), the first guide wire (910) may also be removed prior to advancement of the guide wire (912). Removing the inner elongate member (904) may allow the advancement of a guide wire (912) that has a larger diameter than one that could be placed through the inner elongate member. The outer elongate member (902) may be removed from the body, leaving the guide wire (912) in place within the pericardial space. In some instances, one or more devices may be advanced over the guide wire (912). Additionally or alternatively, one or more dilators may be used to replace the guide wire (912) with a larger guide wire, over which one or more devices may be advanced. It should be appreciated that any of the variations of the access device (200) described above with respect to FIGS. 2 and 3A-3B may be used in these methods.

Figure 10A:
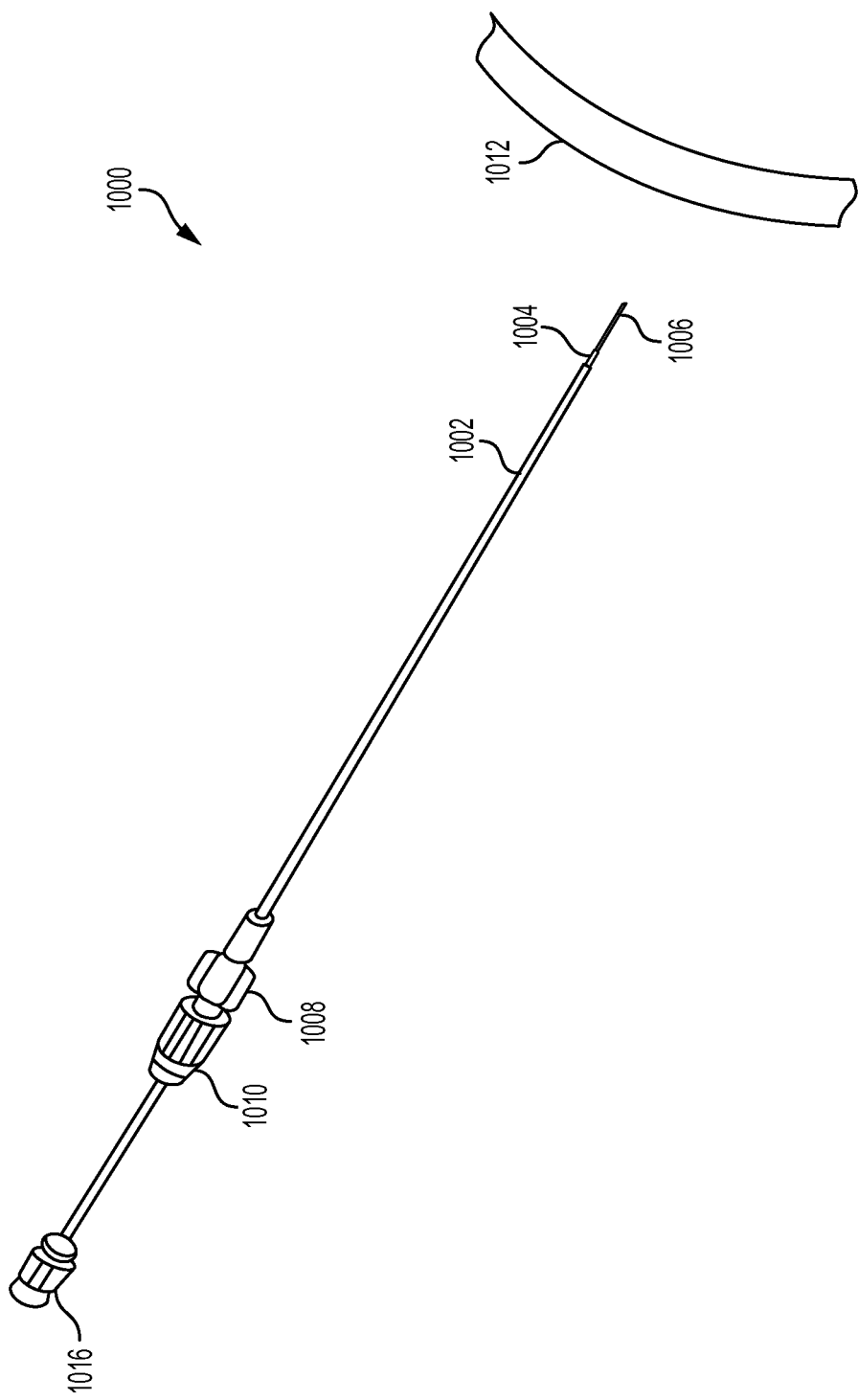
FIGS. 10A-10E depict another illustrative method of accessing the pericardial space using a variation of the access devices described here.

FIGS. 10A-10E illustrate a method of accessing the pericardial space using an access device (1000) having a first outer elongate member (1002), a second intermediate elongate member (1004), and a third inner elongate member (1006). A tubular member of the inner elongate member (1006) may be arranged in a lumen of the intermediate elongate member (1004), and a tubular member of the intermediate elongate member (1004) may be arranged in a lumen of the outer tubular member (1002). The access device (1000) may be advanced through an entry site in the body (e.g., a sub-xiphoid access site), to position a distal end of the access device at the external surface of the pericardium (1012), as shown in FIG. 10A. Specifically, the access device (1000) may be placed in a delivery configuration when the access device (1000) is positioned at the pericardium (1012). The delivery configuration may be any of the delivery configurations described above with respect to the variations of the access device (600) described above in FIGS. 6 and 7A-7B. For example, in some variations, when the access device (1000) is positioned in the delivery configuration, the distal tip of the inner elongate member (1006) may extend slightly beyond the distal tip of the intermediate elongate member (1004), which in turn may extend slightly beyond the distal tip of the outer elongate member (1002), such as discussed in more detail above.

Figure 10B:
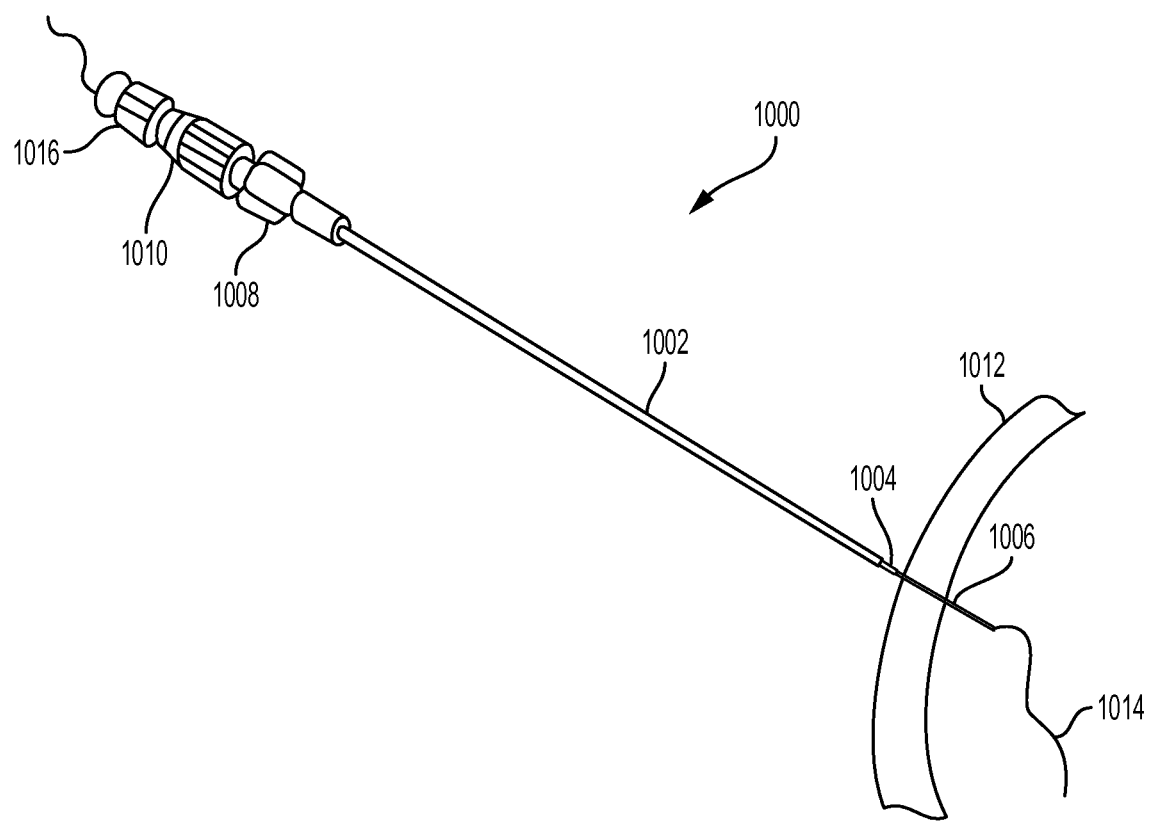
Figure 10C:
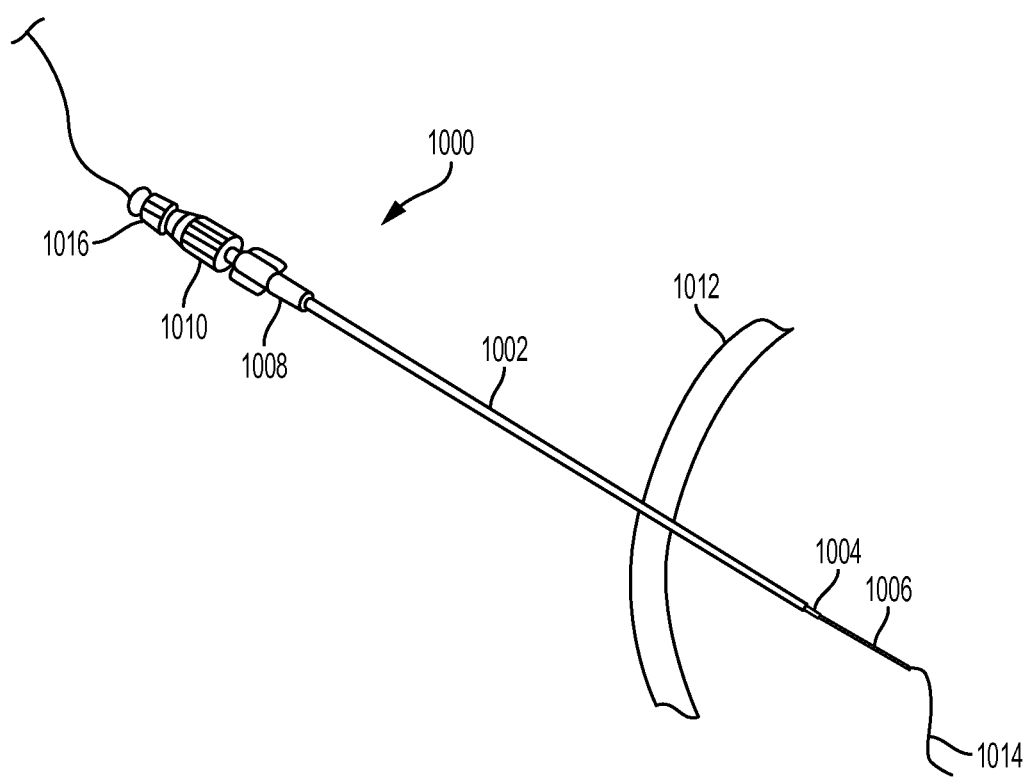
Figure 10D:
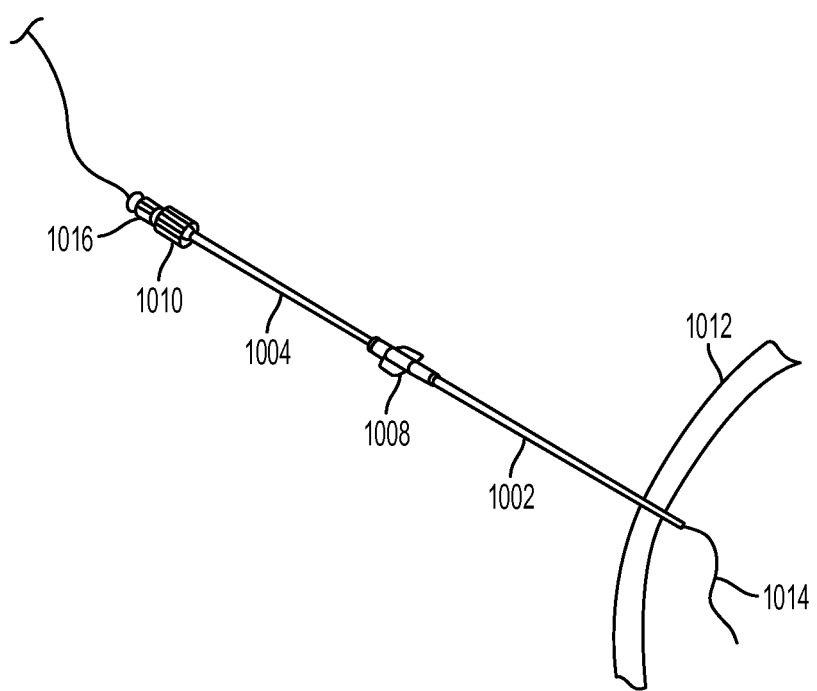
Figure 10E:
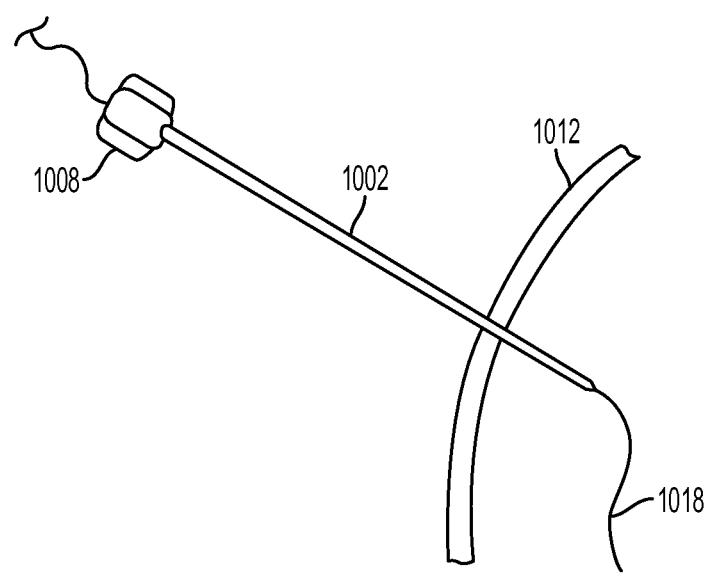
Figure 11A:
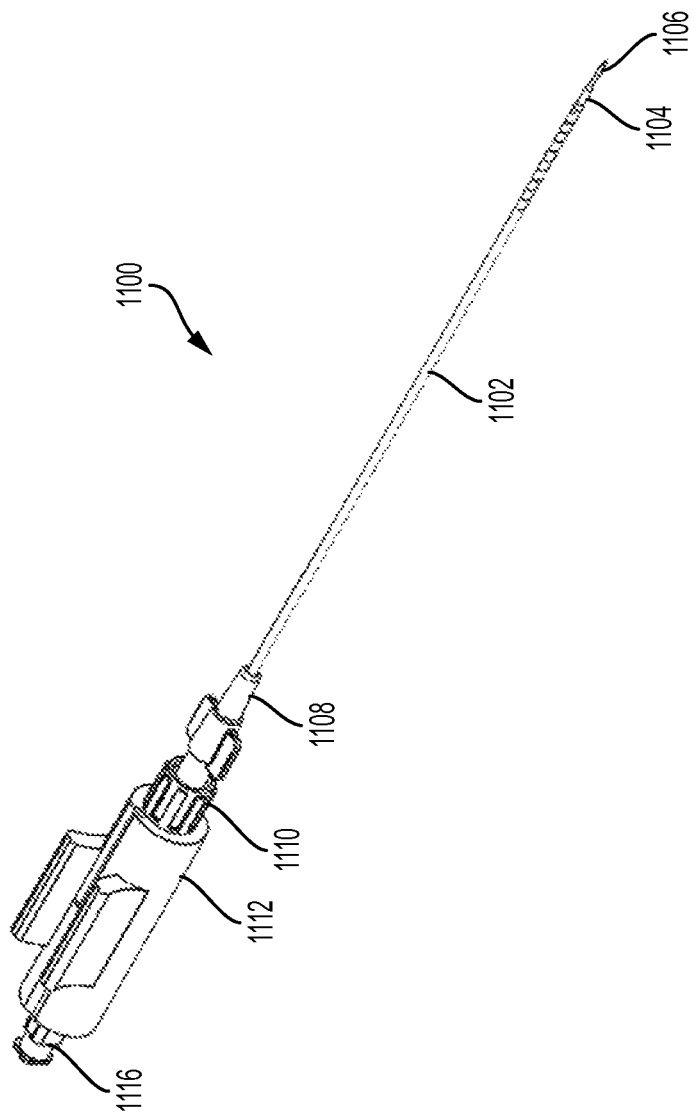
FIGS. 11A and 11B depict a variation of an illustrative method of accessing the pericardial space using the access devices described here.
Figure 11B:
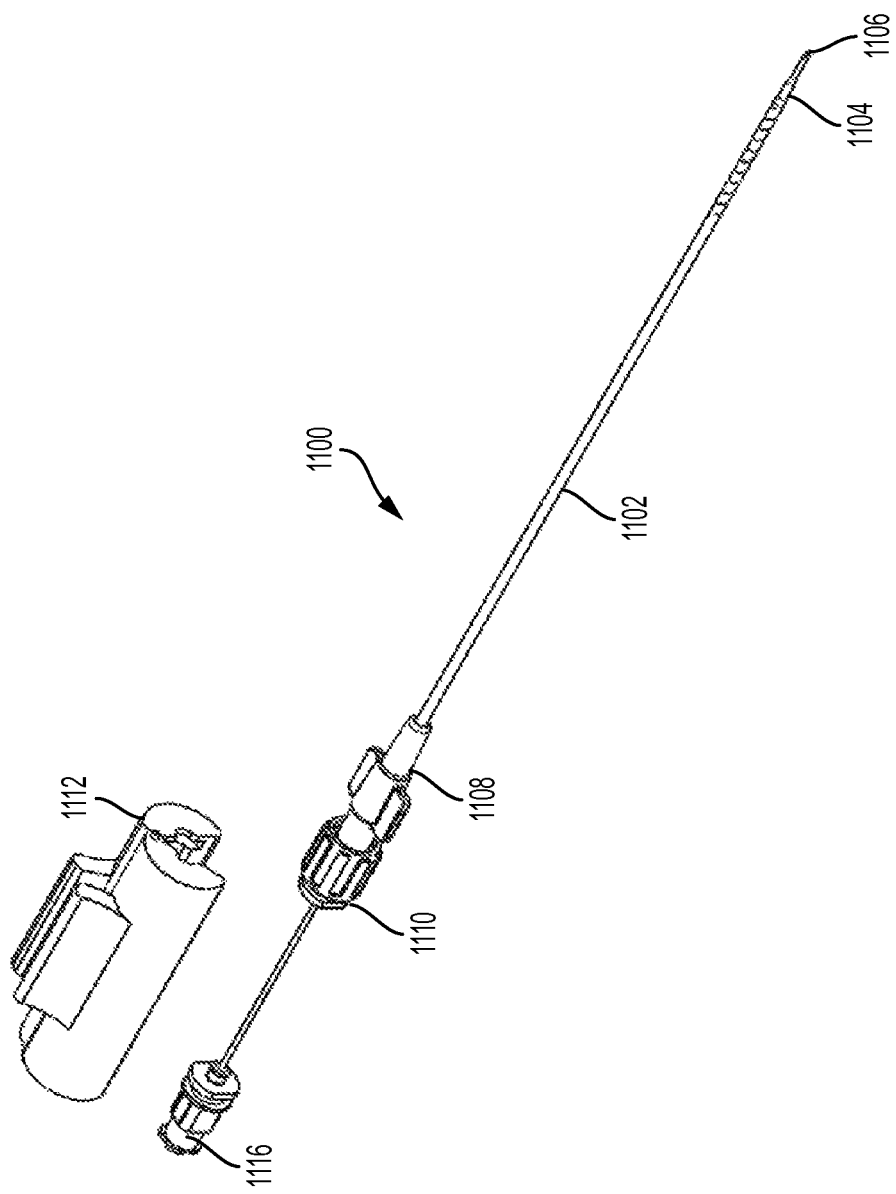

In some variations, the access device (1000) may be advanced into the body and positioned at the pericardium (1012) while in the delivery configuration. In these variations, the inner, intermediate, and outer elongate members may be advanced and manipulated together. In some variations, one or more locking members or connectors may hold the access device in the delivery configuration. For example, FIGS. 11A and 11B show a variation of the method described with respect to FIGS. 10A-10E, in which the access device (1100) may be held in a delivery configuration using a locking member (1112). The locking member (1112) may be any suitable locking member, for example, any of the locking members described above, and may be used as described above. For example, in some variations, the locking member (1112) may releasably fix or otherwise constrain the movement of the inner elongate member (1106) relative to the intermediate elongate member (1104) during at least a portion of a procedure, for example, during advancement to the pericardium. If desired, the locking member (1112) may be disengaged or otherwise removed from the access device (1100) at any point during a procedure, for example, when the distal tip of the inner elongate member (1104) reaches an external surface of the pericardium or after the inner, intermediate, and/or outer elongate members (1106, 1104, 1102) puncture the pericardium. In some variations, the locking member (1108) may be radially disengaged from the access device (1100), such as discussed in more detail above. In some instances, the locking member (1112) may remain in place or otherwise engaged with the access device (1100) throughout the procedure.

In some variations, the access device (1100) may comprise a second locking member configured to releasably fix or otherwise constrain the relative positions of the intermediate elongate member (1104) and the outer elongate member (1102), such as described above. In some instances, the intermediate elongate member (1104) may comprise a connector (1110) releasably connected to a connector (1108) of the outer elongate member (1102). In still other variations, a locking member may be configured to releasably fix or constrain the intermediate elongate member (1104) relative to the outer elongate member (1102), and a connector (1116) of the inner elongate member (1106) may releasably connect to a connector (1110) of the intermediate elongate member (1104) to releasably fix the inner elongate member (1106) relative to the intermediate elongate member (1104).

Turning back to FIGS. 10A-10E, in some variations, some or all of the elongate members may be advanced sequentially. For example, in some variations, the outer elongate member (1002) may first be advanced into the body to position a distal tip of the outer elongate member (1002) at an external surface of the pericardium. In some of these variations, a tubular member of the intermediate elongate member (1004) may then be advanced into a lumen of the outer elongate member (1002), and a tubular member of the inner elongate member (1006) may then be advanced into a lumen of the intermediate elongate member (1004) to position the access device in the delivery configuration. In other variations, the tubular member of inner elongate member (1006) may be advanced into the lumen of the intermediate elongate member (1004), and the tubular members of the inner and intermediate elongate members (1006, 1004) may be advanced together into the lumen of the outer elongate member. In variations that include locking members and/or connectors to hold the access device in the delivery configuration, these members may be used to releasably fix the access device in the delivery configuration and/or facilitate placement of the access device in the delivery configuration, such as discussed above.

After the access device (1000) has been positioned as depicted in FIG. 10A, the access device (1000) may be moved from a delivery configuration to a piercing configuration. In variations where a locking member is engaged or is otherwise connected to one or both of the inner and intermediate elongate members, the locking member may be disengaged from the inner and intermediate elongate members. The inner elongate member (1006) may be advanced relative to the intermediate elongate member (1004) and the outer elongate member (1002) to move the access device (1000) to a piercing configuration, as depicted in FIG. 10B. As the inner elongate member (1006) is advanced relative to the outer elongate member (1002) and the intermediate elongate member (1004), a distal tip of the inner elongate member (1002) (which may be configured to pierce tissue) may puncture the pericardium (1012) to enter the pericardial space. In some variations, the inner elongate member (1006) may be advanced until the handle (1016) of the inner elongate member (1006) reaches the handle (1010) of the intermediate elongate member (1004). In some of these variations, the inner elongate member (1006) may be connected to the intermediate elongate member (1004) when the access device is positioned in the piercing configuration (e.g., a connector on a handle (1008) of the inner elongate member (1006) may releasably connect to a handle (1010) of the intermediate elongate member (1004)). In some instances, all three of the elongate members (inner, intermediate, outer) (1006, 1004, 1002) may be attached when the access device (1000) is in the piercing configuration (e.g., a connector on the handle (1016) of the inner elongate member (1006) may be attached to a connector on the handle (1010) of the intermediate elongate member (1004), which may be attached to a connector on the handle (1008) of the outer elongate member (1002). In some variations, the inner elongate member (1006) may extend at least about 2 inches (5.08 cm) from the distal tip of the intermediate elongate member (1004).

In some variations, a first guide wire (1014) may be advanced through a lumen of the inner elongate member (1006) to position a distal portion of the first guide wire (1014) in the pericardial space, as shown in FIG. 10B. In some instances, the first guide wire (1014) may be used to confirm that the inner elongate member has entered the pericardial space. As the first guide wire (1014) is advanced into the pericardial space, it may wrap around the heart or otherwise be constrained within the pericardium, which may be confirmed using indirect visualization (e.g., via fluoroscopy). In some variations, placement of the first guide wire may prevent or reduce the risk of heart lacerations or puncture as portions of the access device are advanced and manipulated. Additionally or alternatively, a fluid or gas (e.g., carbon dioxide) may be introduced into the pericardial space to lift the pericardium away from the heart. In some variations, the access device may be removed from the body, leaving the first guide wire (1014) in place in the pericardial space. In some instances, one or more devices may be advanced over the first guide wire (1014). Additionally or alternatively, one or more dilators may be used to replace the first guide wire (1014) with a larger guide wire, over which one or more devices may be advanced.

In some variations, once the inner elongate member (1006) has pierced the pericardium (1012), the outer elongate member (1002) and/or intermediate elongate member (1004) may be advanced over inner elongate member (1006). The inner elongate member (1006) may act as a guide in advancing the outer and/or intermediate elongate members (1004, 1002) and/or may help provide a smooth transition for the outer and intermediate elongate members through the pericardium and into the pericardial space. In some variations, the outer elongate member (1002) and the intermediate elongate member (1004) may be advanced over the inner elongate member to position the distal tips of the intermediate and outer elongate members (1004, 1002) in the pericardial space, as shown in FIG. 10C. The inner and outer elongate members may be advanced simultaneously, or sequentially. When the outer elongate member (1002) is positioned in the pericardial space, the inner elongate member (1006) and intermediate elongate member (1004) may be removed from the outer elongate member (1002), as shown in FIG. 10D, and a guide wire (1018) may be advanced through a lumen of the outer elongate member (1002) to position the guide wire (1018) in the pericardial space, such as shown in FIG. 10E. In variations where a first guide wire (1014) is advanced through the inner elongate member (1006), the first guide wire (1014) may also be removed prior to advancement of the guide wire (1018). Removing the inner elongate member (1006) and the intermediate elongate member (1004) may allow the guide wire (1018) to have a larger diameter than could be placed through the inner elongate member or the intermediate elongate member. The outer elongate member (1002) may be removed from the body, leaving the guide wire (1018) in place within the pericardial space. In some instances, one or more devices may be advanced over the guide wire (1018). Additionally or alternatively, one or more dilators may be used to replace the guide wire (1018) with a larger guide wire, over which one or more devices may be advanced. It should be appreciated that any of the variations of the access device (600) described above with respect to FIGS. 6-8 may be used in these methods.

Although the foregoing invention has, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination. The description of certain elements or characteristics with respect to a specific figure are not intended to be limiting or nor should they be interpreted to suggest that the element cannot be used in combination with any of the other described elements.

The invention claimed is:

1. A method of accessing a pericardial space between a pericardium and a heart, the method comprising:
    advancing a distal portion of an access device in a delivery configuration to the pericardium, wherein the access device comprises:
        a first elongate member comprising a lumen therethrough, wherein a first connector is coupled to the first elongate member; and
        a second elongate member comprising a lumen therethrough and a sharpened distal tip, the second elongate member at least partially slideably positioned within the lumen of the first elongate member, wherein a second connector is coupled to the second elongate member,
        wherein the first elongate member is stiffer than the second elongate member, and wherein the first and second connectors releasably couple the first and second elongate members via a releasably coupling locking member, and when the locking member is coupled, the first and second connectors, fix the relative positions of the first and second elongate members, and wherein, in the delivery configuration, the first and second connectors are engaged and the sharpened distal tip of the second elongate member extends distally beyond a distal tip of the first elongate member;
    disengaging the first and second connectors by decoupling the locking member;
    after disengaging the first and second connectors, advancing the second elongate member so that the sharpened distal tip of the second elongate member extends to pierce the pericardium and enter the pericardial space; and
    advancing a distal portion of a first guide wire through the lumen of the second elongate member and into the pericardial space.

2. The method of claim 1, further comprising removing the access device from the pericardial space and advancing an introducer along the first guide wire into the pericardial space.

3. The method of claim 2, wherein the introducer is a 4-French or a 6-French introducer.

4. The method of claim 2, further comprising removing the distal portion of the first guide wire from the pericardial space and advancing a distal portion of a second guide wire through the introducer into the pericardial space.

5. The method of claim 4, wherein the second guide wire has a larger diameter than the first guide wire.

6. The method of claim 1, wherein advancing a distal portion of an access device to the pericardium comprises advancing a distal portion of an access device using a sub-xiphoid approach.

7. The method of claim 1, wherein the first and second elongate members comprise needles.

8. The method of claim 1, wherein decoupling the locking member comprises rotating the locking member relative to the first and second elongate members.

9. The method of claim 1, wherein the locking member comprises a body that is about 2 inches in length.

10. The method of claim 1, wherein the locking member comprises a longitudinal slit.

11. The method of claim 1, wherein the locking member comprises a connector configured to releasably connect to the first connector and a connector configured to releasably connect to the second connector.

12. The method of claim 1, wherein a distal tip of the first elongate member comprises a laser-cut pattern.

13. The method of claim 1, wherein a diameter of the first guide wire is about 0.018 inches.

14. The method of claim 1, wherein in the delivery configuration, the distal tip of the second elongate member extends beyond the distal tip of the first elongate member by a distance between 0.1 and 0.2 inches.

15. The method of claim 1, wherein the locking member is coupled during advancement of the access device to constrain the first and second elongate members in the delivery configuration.

* * * * *